United States Patent
Jaenisch et al.

(10) Patent No.: US 12,053,465 B2
(45) Date of Patent: Aug. 6, 2024

(54) KCC2 EXPRESSION ENHANCING COMPOUNDS AND USES THEREOF

(71) Applicant: Whitehead Institute for Biomedical Research, Cambridge, MA (US)

(72) Inventors: Rudolf Jaenisch, Brookline, MA (US); Xin Tang, Quincy, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 17/713,880

(22) Filed: Apr. 5, 2022

(65) Prior Publication Data

US 2022/0378782 A1    Dec. 1, 2022

Related U.S. Application Data

(62) Division of application No. 16/615,676, filed as application No. PCT/US2018/033912 on May 22, 2018, now Pat. No. 11,331,313.

(60) Provisional application No. 62/509,652, filed on May 22, 2017.

(51) Int. Cl.
| A61K 31/496 | (2006.01) |
| A61K 31/05 | (2006.01) |
| A61K 31/404 | (2006.01) |
| A61K 31/4525 | (2006.01) |
| A61K 31/47 | (2006.01) |
| A61K 31/4709 | (2006.01) |
| A61K 31/519 | (2006.01) |
| A61P 25/28 | (2006.01) |

(52) U.S. Cl.
CPC ............ *A61K 31/496* (2013.01); *A61K 31/05* (2013.01); *A61K 31/404* (2013.01); *A61K 31/4525* (2013.01); *A61K 31/47* (2013.01); *A61K 31/4709* (2013.01); *A61K 31/519* (2013.01); *A61P 25/28* (2018.01)

(58) Field of Classification Search
CPC .... A61K 31/496; A61K 31/05; A61K 31/404; A61K 31/4525; A61K 31/47; A61K 31/4709; A61K 31/519; A61P 25/28; C07D 231/56; C07D 401/12; C07D 409/12
See application file for complete search history.

(56) References Cited

U.S. PATENT DOCUMENTS

| 6,057,117 A | 5/2000 | Harrison et al. |
| 6,153,618 A | 11/2000 | Schultz et al. |
| 6,417,185 B1 | 7/2002 | Goff et al. |
| 6,608,063 B2 | 8/2003 | Nuss et al. |
| 6,780,625 B2 | 8/2004 | Eldar-Finkelman |
| 6,949,544 B2 | 9/2005 | Bethiel et al. |
| 7,045,519 B2 | 5/2006 | Nuss et al. |
| 7,256,190 B2 | 8/2007 | Cochran et al. |
| 7,304,071 B2 | 12/2007 | Cochran et al. |
| 7,361,763 B2 | 4/2008 | Arnold et al. |
| 7,446,199 B2 | 11/2008 | Aronov et al. |
| 7,452,993 B2 | 11/2008 | Arnold et al. |
| 7,514,445 B2 | 4/2009 | Freyne et al. |
| 7,795,279 B2 | 9/2010 | Ballentine et al. |
| 7,872,129 B2 | 1/2011 | Forster et al. |
| 7,994,127 B2 | 8/2011 | Sur et al. |
| 8,993,615 B2 | 3/2015 | Zack et al. |
| 9,539,259 B2 | 1/2017 | Zack et al. |
| 11,331,313 B2 | 5/2022 | Jaenisch et al. |
| 2001/0034051 A1 | 10/2001 | Nuss et al. |
| 2002/0147146 A1 | 10/2002 | Eldar-Finkelman |
| 2002/0156087 A1 | 10/2002 | Nuss et al. |
| 2003/0008866 A1 | 1/2003 | Nuss et al. |
| 2003/0087922 A1 | 5/2003 | Bethiel et al. |
| 2004/0034037 A1 | 2/2004 | Harbeson et al. |
| 2004/0106615 A1 | 6/2004 | Cochran et al. |
| 2005/0004125 A1 | 1/2005 | Freyne et al. |

(Continued)

FOREIGN PATENT DOCUMENTS

| WO | WO 2001/070729 A1 | 9/2001 |
| WO | WO 2002/020495 A2 | 3/2002 |

(Continued)

OTHER PUBLICATIONS

International Search Report and Written Opinion, mailed Sep. 27, 2018, in connection with Application No. PCT/US2018/033912.

(Continued)

*Primary Examiner* — Rei Tsang Shiao

(74) *Attorney, Agent, or Firm* — Wolf, Greenfield & Sacks, P.C.

(57) ABSTRACT

Potassium chloride cotransporter-2 (KCC2) plays a critical role in brain function, and deficiency in KCC2 has been linked to neurological diseases, psychiatric disorders, and central nervous system injuries. In particular, Rett syndrome (RTT), a severe neurodevelopmental disorder caused by mutations in the X-linked gene Methyl CpG binding Protein 2 (MECP2), has been linked to deficits in KCC2. The disclosure reports the use of CRISPR/Cas9 genome-editing technology to generate stem cell-derived, genetically defined KCC2 reporter human neurons for large-scale compound screening. This screening platform has been utilized to identify a number of small molecule compounds that are capable of enhancing KCC2 expression in both wild-type and RTT neurons, as well as organotypical brain slices cultured from wild-type mice. These first-in class compounds may be applied as a novel therapeutic approach to restore the impaired balance between excitation and inhibition observed in neurological diseases, psychiatric disorders, and central nervous system injuries.

18 Claims, 49 Drawing Sheets

Specification includes a Sequence Listing.

(56) References Cited

U.S. PATENT DOCUMENTS

| | | |
|---|---|---|
| 2005/0004152 A1 | 1/2005 | Cochran et al. |
| 2005/0054663 A1 | 3/2005 | Bennett et al. |
| 2005/0124637 A1 | 6/2005 | Cheng et al. |
| 2005/0137201 A1 | 6/2005 | Aronov et al. |
| 2005/0171171 A1 | 8/2005 | Mehta et al. |
| 2006/0281771 A1 | 12/2006 | Baumann et al. |
| 2006/0281788 A1 | 12/2006 | Baumann et al. |
| 2007/0197591 A1 | 8/2007 | Boom et al. |
| 2008/0139472 A1 | 6/2008 | Lauterborn et al. |
| 2008/0207594 A1 | 8/2008 | Mussmann et al. |
| 2009/0054358 A1 | 2/2009 | Small et al. |
| 2009/0118278 A1 | 5/2009 | Forster et al. |
| 2009/0142337 A1 | 6/2009 | Squires |
| 2013/0156764 A1 | 6/2013 | Levis et al. |
| 2014/0107141 A1 | 4/2014 | Wagner et al. |
| 2015/0119327 A1 | 4/2015 | Muotri et al. |
| 2017/0014421 A1 | 1/2017 | Boulenguez et al. |

FOREIGN PATENT DOCUMENTS

| | | |
|---|---|---|
| WO | WO 2003/037347 A1 | 5/2003 |
| WO | WO 2004/018455 A1 | 3/2004 |
| WO | WO 2008/139161 A1 | 11/2008 |
| WO | WO 2012/004217 A1 | 1/2012 |
| WO | WO 2014/017659 A1 | 1/2014 |

OTHER PUBLICATIONS

International Preliminary Report on Patentability, mailed Dec. 5, 2019, in connection with Application No. PCT/US2018/033912.

[No Author Listed], Paliperidone. PubChem CID No. 115237. Aug. 8, 2005. Retrieved from https://pubchem.ncbi.nlm.nih.gov/compound/115237 on Aug. 18, 2021. 63 pages.

[No Author Listed], Valinomycin. PubChem CID No. 3000706. Aug. 1, 2005. Retrieved from https://pubchem.ncbi.nlm.nih.gov/compound/3000706 on Aug. 18, 2021. 34 pages.

Arion et al., Altered expression of regulators of the cortical chloride transporters NKCC1 and KCC2 in schizophrenia. Arch Gen Psychiatry. 2011;68(1):21-31. doi:10.1001/archgenpsychiatry.2010.114.

Banerjee et al., Jointly reduced inhibition and excitation underlies circuit-wide changes in cortical processing in Rett syndrome. Proc Natl Acad Sci U S A. 2016;113(46):E7287-E7296. doi:10.1073/pnas.1615330113.

Baur et al., Therapeutic potential of resveratrol: the in vivo evidence. Nat Rev Drug Discov. 2006;5(6):493-506. doi:10.1038/nrd2060.

Ben-Ari, NKCC1 Chloride Importer Antagonists Attenuate Many Neurological and Psychiatric Disorders. Trends Neurosci. 2017;40(9):536-554. doi:10.1016/j.tins.2017.07.001.

Boulenguez et al., Down-regulation of the potassium-chloride cotransporter KCC2 contributes to spasticity after spinal cord injury. Nat Med. 2010;16(3):302-307. doi:10.1038/nm.2107.

Brazel et al., The FLT3 tyrosine kinase receptor inhibits neural stem/progenitor cell proliferation and collaborates with NGF to promote neuronal survival. Mol Cell Neurosci. 2001;18(4):381-393. doi:10.1006/mcne.2001.1033.

Chahrour et al., MeCP2, a key contributor to neurological disease, activates and represses transcription. Science. 2008;320(5880):1224-1229. doi:10.1126/science.1153252.

Chao et al., Dysfunction in GABA signalling mediates autism-like stereotypies and Rett syndrome phenotypes. Nature. 2010;468(7321):263-269. doi:10.1038/nature09582.

Chao et al., MeCP2 controls excitatory synaptic strength by regulating glutamatergic synapse number. Neuron. 2007;56(1):58-65. doi:10.1016/j.neuron.2007.08.018.

Chapleau et al., Dendritic spine pathologies in hippocampal pyramidal neurons from Rett syndrome brain and after expression of Rett-associated MECP2 mutations. Neurobiol Dis. 2009;35(2):219-233. doi:10.1016/j.nbd.2009.05.001.

Dani et al., Intact long-term potentiation but reduced connectivity between neocortical layer 5 pyramidal neurons in a mouse model of Rett syndrome. J Neurosci. 2009;29(36):11263-11270. doi:10.1523/JNEUROSCI.1019-09.2009.

Dani et al., Reduced cortical activity due to a shift in the balance between excitation and inhibition in a mouse model of Rett syndrome. Proc Natl Acad Sci U S A. 2005;102(35):12560-12565. doi:10.1073/pnas.0506071102.

Deidda et al., Reversing excitatory GABAAR signaling restores synaptic plasticity and memory in a mouse model of Down syndrome. Nat Med. 2015;21(4):318-326. doi:10.1038/nm.3827.

Delpire et al., The KCC3 cotransporter as a therapeutic target for peripheral neuropathy. Expert Opin Ther Targets. 2017;21(2):113-116. doi:10.1080/14728222.2017.1275569.

Duarte et al., Abnormal expression of cerebrospinal fluid cation chloride cotransporters in patients with Rett syndrome. PLoS One. 2013;8(7):e68851. Published Jul. 19, 2013. doi:10.1371/journal.pone.0068851.

Dzhala et al., NKCC1 transporter facilitates seizures in the developing brain. Nat Med. 2005;11(11):1205-1213. doi:10.1038/nm1301.

Eldar-Finkelman et al., GSK-3 Inhibitors: Preclinical and Clinical Focus on CNS. Front Mol Neurosci. 2011;4:32. Published Oct. 31, 2011. doi:10.3389/fnmol.2011.00032.

Gagnon et al., Chloride extrusion enhancers as novel therapeutics for neurological diseases. Nat Med. 2013;19(11):1524-1528. doi:10.1038/nm.3356.

Gauvain et al., The neuronal K-Cl cotransporter KCC2 influences postsynaptic AMPA receptor content and lateral diffusion in dendritic spines [published correction appears in Proc Natl Acad Sci U S A. Oct. 6, 2015;112(40):E5554]. Proc Natl Acad Sci U S A. 2011;108(37):15474-15479. doi:10.1073/pnas.1107893108.

Guida et al., Resveratrol via sirtuin-1 downregulates RE1-silencing transcription factor (REST) expression preventing PCB-95-induced neuronal cell death. Toxicol Appl Pharmacol. 2015;288(3):387-398. doi:10.1016/j.taap.2015.08.010.

Henderson et al., Reversal of disease-related pathologies in the fragile X mouse model by selective activation of GABAB receptors with arbaclofen. Sci Transl Med. 2012;4(152):152ra128. doi:10.1126/scitranslmed.3004218.

Hyde et al., Expression of GABA signaling molecules KCC2, NKCC1, and GAD1 in cortical development and schizophrenia. J Neurosci. 2011;31(30):11088-11095. doi:10.1523/JNEUROSCI.1234-11.2011.

Jaenisch et al., Downregulation of potassium chloride cotransporter KCC2 after transient focal cerebral ischemia. Stroke. 2010;41(3):e151-e159. doi:10.1161/STROKEAHA.109.570424.

Johnson et al., 7,8-dihydroxyflavone exhibits therapeutic efficacy in a mouse model of Rett syndrome. J Appl Physiol (1985). Mar. 2012;112(5):704-10. doi: 10.1152/japplphysiol.01361.2011. Epub Dec. 22, 2011.

Kahle et al., Genetically encoded impairment of neuronal KCC2 cotransporter function in human idiopathic generalized epilepsy. EMBO Rep. 2014;15(7):766-774. doi:10.15252/embr.201438840.

Kahle et al., The KCC2 Cotransporter and Human Epilepsy: Getting Excited About Inhibition. Neuroscientist. 2016;22(6):555-562. doi:10.1177/1073858416645087.

Kelley et al., Compromising KCC2 transporter activity enhances the development of continuous seizure activity. Neuropharmacology. 2016;108:103-110. doi:10.1016/j.neuropharm.2016.04.029.

Lee et al., NMDA receptor activity downregulates KCC2 resulting in depolarizing GABAA receptor-mediated currents. Nat Neurosci. 2011;14(6):736-743. doi:10.1038/nn.2806.

Li et al., Antidepressant like effects of piperine in chronic mild stress treated mice and its possible mechanisms. Life Sci. 2007;80(15):1373-1381. doi:10.1016/j.lfs.2006.12.027.

Martin-Aragon Baudel et al., Chloride co-transporters as possible therapeutic targets for stroke. J Neurochem. 2017;140(2):195-209. doi:10.1111/jnc.13901.

Merner et al., Regulatory domain or CpG site variation in SLC12A5, encoding the chloride transporter KCC2, in human autism and schizophrenia. Front Cell Neurosci. 2015; 9: 386. Epub Oct. 12, 2015. doi: 10.3389/fncel.2015.00386.

(56) References Cited

OTHER PUBLICATIONS

Monteggia et al., Rett syndrome and the impact of MeCP2 associated transcriptional mechanisms on neurotransmission. Biol Psychiatry. 2009;65(3):204-210. doi:10.1016/j.biopsych.2008.10.036.

Nguyen et al., MeCP2 is critical for maintaining mature neuronal networks and global brain anatomy during late stages of postnatal brain development and in the mature adult brain. J Neurosci. 2012;32(29):10021-10034. doi:10.1523/JNEUROSCI.1316-12.2012.

Pragnya et al., Ameliorating effect of piperine on behavioral abnormalities and oxidative markers in sodium valproate induced autism in BALB/C mice. Behav Brain Res. 2014;270:86-94. doi:10.1016/j.bbr.2014.04.045.

Puskarjov et al., A variant of KCC2 from patients with febrile seizures impairs neuronal Cl? extrusion and dendritic spine formation. EMBO Rep. Jun. 2014; 15(6): 723-729. EPub Mar. 25, 2014. doi: 10.1002/embr.201438749.

Robertson et al., Reduced GABAergic Action in the Autistic Brain. Curr Biol. 2016;26(1):80-85. doi:10.1016/j.cub.2015.11.019.

Sun et al., Regulation of epileptiform activity by two distinct subtypes of extrasynaptic GABAA receptors. Mol Brain. 2013; 6: 21. EPub May 1, 2013. doi: 10.1186/1756-6606-6-21.

Tang et al., KCC2 rescues functional deficits in human neurons derived from patients with Rett syndrome. Proc Natl Acad Sci U S A. 2016;113(3):751-756. doi:10.1073/pnas.1524013113.

Tang et al., Pharmacological enhancement of KCC2 gene expression exerts therapeutic effects on human Rett syndrome neurons and Mecp2 mutant mice. Sci Transl Med. Jul. 31, 2019;11(503):eaau0164. doi: 10.1126/scitranslmed.aau0164.

Tao et al., Transcript-specific associations of SLC12A5 (KCC2) in human prefrontal cortex with development, schizophrenia, and affective disorders. J Neurosci. 2012;32(15):5216-5222. doi:10.1523/JNEUROSCI.4626-11.2012.

Tornberg et al., Behavioural phenotypes of hypomorphic KCC2-deficient mice. Eur J Neurosci. 2005;21(5):1327-1337. doi:10.1111/j.1460-9568.2005.03959.x. Abstract Only.

Tyzio et al., Oxytocin-mediated GABA inhibition during delivery attenuates autism pathogenesis in rodent offspring. Science. 2014;343(6171):675-679. doi:10.1126/science.1247190.

Ure et al., Restoration of Mecp2 expression in GABAergic neurons is sufficient to rescue multiple disease features in a mouse model of Rett syndrome. Elife. 2016;5:e14198. Published Jun. 21, 2016. doi:10.7554/eLife.14198.

Van Esch et al., Duplication of the MECP2 region is a frequent cause of severe mental retardation and progressive neurological symptoms in males. Am J Hum Genet. 2005;77(3):442-453. doi:10.1086/444549.

Zhang et al., A thallium transport FLIPR-based assay for the identification of KCC2-positive modulators. J Biomol Screen. 2010;15(2):177-184. doi:10.1177/1087057109355708.

KCC2 EXPRESSION ENHANCING COMPOUNDS AND USES THEREOF

RELATED APPLICATIONS

This application is a division of and claims priority under 35 U.S.C. § 120 to U.S. patent application Ser. No. 16/615,676, filed Nov. 21, 2019, which is a national stage filing under 35 U.S.C. § 371 of International PCT Application, PCT/US2018/033912, filed May 22, 2018, which claims priority under 35 U.S.C. § 119(e) to U.S. Provisional Application, Ser. No. 62/509,652, filed May 22, 2017, which is incorporated herein by reference.

GOVERNMENT SUPPORT

This invention was made with government support under grant number 2R01MH104610-15 awarded by the National Institutes of Health. The government has certain rights in the invention.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Jun. 14, 2022, is named W057170052US02-SEQ-MOD and is 2,145 bytes in size.

BACKGROUND OF THE INVENTION

Autism spectrum disorders (ASD) affect 1 in 68 children in the United States. Although the majority of ASD patients show a common set of autistic behaviors, the pathogenesis is unclear for most cases. Rett syndrome (RTT) is a genetically defined type of ASD caused by mutations in the X-linked gene Methyl CpG binding Protein 2 (MECP2) that affects one in every 10,000 live female births in the United States. Deficits in potassium chloride cotransporter-2 (KCC2) gene expression has been described in various neurological diseases, psychiatric disorders, and central nervous system injuries including epilepsy, schizophrenia, as well as ASD and Rett syndrome (RTT). Development of effective therapies targeted at KCC2 gene expression to treat RTT have great potential, for it will not only be beneficial to the thousands of RTT patients, but also to millions of patients worldwide suffering from ASD, epilepsy, schizophrenia, mental retardation, stroke, Fragile-X syndrome, traumatic brain injury, and spinal cord injury.

SUMMARY OF THE INVENTION

Rett syndrome (RTT), a severe neurodevelopmental disorder caused by mutations in the X-linked gene Methyl CpG binding Protein 2 (MECP2), is one of the most common causes for mental retardation in females. Experiments conducted in MECP2-knockout RTT mouse models have shown that RTT phenotypes in adult animals can be reversed through re-expression of MECP2, or by pharmacological treatment, highlighting the possibility of developing an effective treatment for symptomatic RTT patients. One possible therapeutic strategy for treating RTT patients is to restore MECP2 expression by reactivation of the inactive X chromosome that presumably carries the wild-type (WT) copy of MECP2. However, the potential oncogenic transformation of X chromosome reactivation is a potential side effect, which renders this approach problematic as a long-term therapy. An alternative strategy is to modulate a molecular pathway that is disrupted in the RTT brain but does not directly involve MECP2. Published work on this "downstream targets" approach has identified a number of promising molecular targets to treat RTT phenotypes including brain-derived neurotrophic factor (BDNF), insulin-like growth factor-1 (IGF-1), NMDA receptor, and cholesterol metabolism. However, these pathways broadly regulate many downstream gene targets, and the current efficacy of treating RTT symptoms through modulating these pathways is unsatisfactory.

A delicate balance between excitatory and inhibitory neurotransmission (E/I balance) is crucial for the proper functioning of the brain. In the case of Rett syndrome, a reduction in the number of excitatory glutamatergic synapses has been consistently reported from studies using postmortem Rett syndrome (RTT) patient brain samples, mouse models of RTT, and human stem cell-derived RTT neurons. A large proportion of RTT patients suffer from comorbid epilepsy, which strongly indicates a deficit in the inhibitory GABAergic signaling and disruption of the E/I balance contribute to disease. In keeping with the GABA hypothesis of RTT pathogenesis, recent work has shown that knocking-out MECP2 expression specifically in GABAergic neurons lead to severe RTT phenotypes resembling global MECP2 deficiency. Taken together, these data suggest that in order to effectively treat RTT symptoms, restoration of the impaired balance between excitatory and inhibitory neurotransmission may be beneficial.

Potassium chloride cotransporter-2 (KCC2) is a gene essential for the maintenance of the balance between the excitatory and inhibitory signaling in the brain. It is also important for neuroprotection against excitotoxicity, and implied in synaptic plasticity. Deficits in KCC2 expression has been described in various neurological diseases, psychiatric disorders, and central nervous system injuries, including epilepsy, schizophrenia, as well as autism spectrum disorders (ASD) and Rett syndrome (RTT). Similar decreases in KCC2 expression have been detected in animal model of RTT (8). Previously published work has demonstrated that forced expression of KCC2 protein in Rett syndrome (RTT) neurons rescue disease- specific neurotransmission impairments (7).

In some aspects, the present disclosure provides methods to identify KCC2 expression enhancing compounds (KEECs) using a novel screening platform. In certain embodiments, the screening platform uses neurons to identify KCC2 expression enhancing compounds. In some embodiments, the screening platform utilizes reporter neurons engineered using a genome editing technique such as clustered regularly interspaced short palindromic repeats (CRISPR)/Cas genome editing, genome editing using other RNA-guided endonucleases (RGENs), TALEN-based genome editing, or zinc finger based genome editing, or other genome editing technique. In some embodiments, the screening platform utilizes reporter neurons engineered using a genome editing technique and generated from induced pluripotent stem cells (iPS cells). In some embodiments the iPS cells may be derived from a subject who has or is a carrier of Rett syndrome. In some embodiments the iPS cells may be derived from a subject who does not have Rett syndrome and is not a carrier of Rett syndrome. In some embodiments, the iPS cells are rodent iPS cells. In some embodiments, the iPS cells are human iPS cells. In some embodiments, the screening platform utilizes reporter neurons engineered by clustered regularly interspaced short palindromic repeats (CRISPR)/Cas9 genome editing of human embryonic stem cells (ESC). In certain embodiments, the reporter neurons are WT or RTT KCC2-2A-luciferase reporter neurons, which are prepared by insertion of a luciferase reporter gene into the KCC2 locus of human WT or RTT ESC. In certain embodiments the sequence encoding the reporter protein (e.g., luciferase), may be separated from the KCC2 coding sequence by a sequence that encodes a 2A peptide, wherein the sequence that encodes KCC2, the sequence that encodes the 2A peptide, and the sequence that encodes the reporter protein are in frame. This sequence (i.e., GGCAAACCGAT-TCCGAATCCGCTGCTGGGCCTGGATTCCACCTACC-CATACGATG TTCCAGATTACGCTgccactaacttetccctgtt-gaaacaagcaggggatgtegaagagaatcceggggcca (SEQ ID NO: 1), wherein the 2A peptide sequence is in lower case) results in production of an mRNA that is translated into two separate polypeptides: a polypeptide comprising KCC2 and a polypeptide comprising a reporter protein, e.g., luciferase. This allows the neurons to express KCC2 as well as the reporter protein, with expression of both being driven by the KCC2 promoter. In certain embodiments, the insertion site of the reporter is at the end of exon 26 of KCC2. In certain embodiments, the insertion site of the reporter is at the end of exon 25 of KCC2. In certain embodiments, the insertion site of the reporter is at the end of exon 24 of KCC2. In the exemplified embodiment, the polypeptide comprising KCC2 also comprises V5 and HA epitope tags, thus facilitating detection of the polypeptide. 2A peptides, sometimes referred to as "self-cleaving peptides", mediate "ribosome skipping" as well known in the art. Such peptides are found in members of the Picornaviridae virus family, including aphthoviruses such as foot-and-mouth disease virus (FMDV), equine rhinitis A virus (ERAV), Thosea asigna virus (TaV) and porcine teschovirus-1 (PTV-1) (Donnelly, M. L., et al., *J. Gen. Virol.*, 2001, 82, 1027-101; Ryan, M. D., et al., *J. Gen. Virol.*, 2001, 72, 2727-2732) and cardioviruses such as Theilovirus (e.g., Theiler's murine encephalomyelitis) and encephalomyocarditis viruses. The 2A peptides derived from FMDV, ERAV, PTV-1, and TaV are sometimes referred to as "F2A", "E2A", "P2A", and "T2A", respectively. There may be a peptide linker (e.g., one or more serine or glycine residues or a combination thereof) between the 2A peptide sequence and the KCC2 sequence and/or between the 2A peptide sequence and the reporter protein sequence. The screening platform has several unique advantages that allow rapid assessment of the effect of potential drugs on KCC2 expression within the intact gene expression regulatory context in neurons. In certain embodiments, the neurons are human wild type neurons. In certain embodiments, the neurons are RTT cultured human neurons. In certain embodiments, the neurons are rodent neurons. In certain embodiments the neurons are male neurons. In certain embodiments the neurons are female neurons.

In some embodiments, the test compound screened in the screening platform is a small molecule. In certain embodiments, the test compound is an organic molecule. In certain embodiments, the test compound is a compound selected from the group consisting of kinase inhibitors, Feline McDonough sarcoma-like tyrosine kinase 3 (FLT3) inhibitors, glycogen synthase kinase 3 (GSK3) inhibitors, gamma-aminobutyric acid (GABA) inhibitors, GABA reuptake inhibitors, monoamine oxidase inhibitors (MAOI), norepinephrine reuptake inhibitor (NRI), dopamine antagonist, Sirtuin 1 (SIRT1) activators, transient receptor potential cation channel subfamily V member 1 (TRPV1) activators, monoamine transporter activators, tropomyosin receptor kinase B (TrkB) agonists, ampakines, and salts thereof.

The test compounds which are identified to enhance KCC2 expression in the screening platform may be designated hit compounds. In certain embodiments, a hit compound can be altered to provide a modified version of a hit compound. In certain embodiments, a hit compound is chemically altered to provide a modified version of a hit compound. In certain embodiments, a hit compound is altered to provide a modified version with a longer half-life relative to a hit compound. In certain embodiments, a bit compound is altered to provide a modified version with an increased ability to cross the blood-brain barrier relative to a hit compound. In certain embodiments, a hit compound is altered to provide a modified version with a greater solubility relative to a hit compound. In certain embodiments, a hit compound is altered to provide a modified version with an increased potency relative to a hit compound. In certain embodiments, a hit compound is altered to provide a modified version with an increased bioavailability (e.g., oral) relative to a hit compound. In certain embodiments, a hit compound is altered to provide a modified version with an increased stability (e.g., in human plasma) relative to a hit compound. Such compounds may be further tested to validate their ability to enhance KCC2 expression and/or treat a neurological disease, psychiatric disorder, or central nervous system injury discussed herein.

In certain embodiments, the compound is a small molecule. In certain embodiments, the compound is a nucleic acid. In certain embodiments, the compound is a protein or peptide. In certain embodiments, the compound is an organic molecule. In certain embodiments, the compound is a molecule selected from the group consisting of kinase inhibitors, Feline McDonough sarcoma-like tyrosine kinase 3 (FLT3) inhibitors, glycogen synthase kinase 3 (GSK3) inhibitors, gamma-aminobutyric acid (GABA) inhibitors, GABA reuptake inhibitors, monoamine oxidase inhibitors (MAOI), norepinephrine reuptake inhibitor (NRI), dopamine antagonist, Sirtuin 1 (SIRT1) activators, transient receptor potential cation channel subfamily V member 1 (TRPV1) activators, monoamine transporter activators, tropomyosin receptor kinase B (TrkB) agonists, ampakines, and salts thereof. In certain embodiments, the hit compound is a molecule selected from the group consisting of, but not limited to, (E)-(4-(2-(1H-indazol-3-yl)vinyl)phenyl)(piperazin-1-yl)methanone (KW-2449), 2Z,3E)-6'-bromo-3-(hydroxyimino)-[2,3'-biindolinylidene]-2'-one (KIN 001-043), N-(2-diethylaminoethyl)-5-[(Z)-(5-fluoro-2-oxo-1H-indol-3-ylidene)methyl]-2,4-dimethyl-1H-pyrrole-3-carboxamide (Sunitinib), 1-(2-(5-(2-(3-methyloxetan-3-yl)ethyl)-1H-benzo[d]imidazol-1-yl)quinolin-8-yl)piperidin-4-amine (Crenolanib), N'-[4-[(6,7-dimethoxy-4-quinolinyl)oxy]phenyl]-N-(4-fluorophenyl)-1,1-cyclopropanedicarboxamide (XL-184), 3-((6-(3-aminophenyl)-7H-pyrrolo[2,3-d]pyrimidin-4-yl)methyl)phenol (TWS-119), (2Z,3E)-3-(hydroxyimino)-[2,3'-biindolinylidene]-2'-one (Indirubin-monoxime), resveratrol, piperine, and salts thereof. In certain embodiments the compound is a MET proto-oncogene, receptor tyrosine kinase (MET) inhibitor or salt thereof.

Feline McDonough sarcoma-like tyrosine kinase 3 (FLT3) is a class III receptor tyrosine kinase that regulates hematopoiesis, the process of creating new blood cells in the body. This receptor is activated by binding of the FLT3 ligand to the extracellular domain, which induces homodimer formation in the plasma membrane leading to autophosphorylation of the receptor. The activated receptor kinase subsequently phosphorylates and activates multiple cytoplasmic effector molecules in pathways involved in apoptosis, proliferation, and differentiation of hematopoietic cells in bone marrow. Mutations that result in the constitutive activation of this receptor result in acute myeloid leukemia and acute lymphoblastic leukemia. Research efforts to discover inhibitors of feline McDonough sarcoma-like tyrosine kinase 3 (FLT3) has identified the following types of chemical entities as FLT3 inhibitors: ureas, carboxamides, alkaloids, and benzamidazole. Feline McDonough sarcoma-like tyrosine kinase 3 (FLT3) inhibitors designated hit compounds in the present disclosure include (E)-(4-(2-(1H-indazol-3-yl)vinyl)phenyl)(piperazin-1-yl)methanone (KW-2449) [carboxamide], 1-(2-(5-(2-(3-methyloxetan-3-yl) ethyl)-1H-benzo[d]imidazol-1-yl)quinolin-8-yl)piperidin-4-amine (Crenolanib) [benzamidazole], N'-[4-[(6,7-dimethoxy-4-quinolinyl)oxy]phenyl]-N-(4-fluorophenyl)-1, 1-cyclopropanedicarboxamide (XL-184) [carboxamide], and N-(2-diethylaminoethyl)-5-[(Z)-(5-fluoro-2-oxo-1H-indol-3-ylidene)methyl]-2,4-dimethyl-1H-pyrrole-3-carboxamide (Sunitinib) [carboxamide]. The compounds N1'-[3-fluoro-4-[[6-methoxy-7-(3-morpholinopropoxy)-4-quinolyl]oxy]phenyl]-N1-(4-fluorophenyl)cyclopropane-1,1-dicarboxamide (Foretinib) [carboxamide] and 3-[(4-quinolinylmethyl)amino]-N-[4-(trifluoromethoxy)phenyl]-2-thiophenecarboxamide (OSI-930) [carboxamide] are also FLT3 inhibitors designated as hit compounds in the present disclosure.

Glycogen synthase kinase 3 (GSK3) is a serine/threonine protein kinase that mediates the addition of phosphate molecules onto serine and threonine amino acid residues. In mammals, GSK3 is encoded by two genes, GSK3α and GSK3β. GSK3 is involved in a great number of signaling pathways and has been implicated in a number of diseases including Type II diabetes, Alzheimer's disease, inflammation, cancer, and bipolar disorder. Research efforts to discover inhibitors of glycogen synthase kinase 3 (GSK3) has identified the following types of chemical entities as GSK3 inhibitors: metal cations, marine organism derived compounds, ureas, aminopyrimidines, arylindolemaleimides, thiazoles, thiadiazolidindiones, halomethylketones, and peptides. Glycogen synthase kinase 3 (GSK3) inhibitors designated hit compounds (KCC2 expression enhancing compounds) in the present disclosure include 2Z,3E)-6'-bromo-3-(hydroxyimino)-[2,3'-biindolinylidene]-2'-one (KIN 001-043) [marine organism derived], 1-(4-methoxybenzyl)-3-(5-nitrothiazol-2-yl)urea (AR-A014418) [urea], 3-((6-(3-aminophenyl)-7H-pyrrolo[2,3-d]pyrimidin-4-yl)methyl) phenol (TWS-119) [aminopyrimidine], and (2Z,3E)-3-(hydroxyimino)-[2,3'-biindolinylidene]-2'-one (Indirubin-monoxime) [marine organism derived], and indirubin.

MET proto-oncogene, receptor tyrosine kinase (MET) is a single pass tyrosine kinase receptor with important roles in embryonic development, organogenesis and wound healing. Hepatocyte growth factor/Scatter Factor (HGF/SF) and its splicing isoform (NK1, NK2) are the known ligands of the MET receptor. MET is normally expressed by cells of epithelial origin and is also expressed in neurons, hepatocytes, hematopoietic cells, melanocytes and neonatal cardiomyocytes. MET engagement activates multiple signal transduction pathways, many of which are involved in the cellular program known as invasive growth. MET inhibitors designated hit compounds in the present disclosure include N-(4-(2-amino-3-chloropyridin-4-yloxy)-3-fluorophenyl)-4-ethoxy-1-(4-fluorophenyl)-2-oxo-1,2-dihydropyridine-3-carboxamide (BMS 777607), N1'-[3-fluoro-4-[[6-methoxy-7-(3-morpholinopropoxy)-4-quinolyl]oxy]phenyl]-N1-(4-fluorophenyl)cyclopropane-1,1-dicarboxamide (Foretinib), and Cabozantinib (XL-184).

In some embodiments, the bit compounds or modified versions thereof are validated by a secondary assay. In certain embodiments, the KCC2 expression enhancing compounds are assayed by Western blot experiments. In certain embodiments, the amount of gene expression by the Western blot experiments is detected by chemiluminescence. In certain embodiments, the KCC2 expression enhancing compounds are assayed by Western blot experiments with WT and/or RTT cultured human neurons. In some embodiments, the KCC2 expression enhancing compounds are assayed using brain tissue slices, e.g., prepared from neonatal rodent brain. In some embodiments the KCC2 enhancing compounds may be tested in an animal model of a disorder described herein, e.g., RTT syndrome. For example, the compounds may be tested for ability to alleviate at least one symptom of the disorder in the animal model. The KCC2 expression enhancing compounds identified and validated in human neurons could potentially be developed into therapies that stimulate KCC2 expression for the treatment of subjects afflicted with various neurological diseases, psychiatric disorders, or central nervous system (e.g., brain) injuries. In certain embodiments, the neurological diseases, psychiatric disorders, or central nervous system injuries are selected from a group consisting of, but not limited to, ASD, RTT, epilepsy, schizophrenia, mental retardation, stroke, Fragile-X syndrome, traumatic brain injury, and spinal cord injury. In certain embodiments, the condition is Down syndrome.

In some aspects, the present disclosure provides methods of treating a subject with a neurological disease, psychiatric disorder, or central nervous system injury characterized by deficient expression or function of KCC2. In certain embodiments, the subject is administered a therapeutically effective amount of a compound selected from the group consisting of kinase inhibitors, Feline McDonough sarcoma-like tyrosine kinase 3 (FLT3) inhibitors, glycogen synthase kinase 3 (GSK3) inhibitors, gamma-aminobutyric acid (GABA) inhibitors, GABA reuptake inhibitors, monoamine oxidase inhibitors (MAOI), norepinephrine reuptake inhibitor (NRI), dopamine antagonist, Sirtuin 1 (SIRT1) activators, transient receptor potential cation channel subfamily V member 1 (TRPV1) activators, monoamine transporter activators, tropomyosin receptor kinase B (TrkB) agonists, ampakines, and pharmaceutically acceptable salts thereof. In certain embodiments, the compound is selected from the group consisting of (E)-(4-(2-(1H-indazol-3-yl)vinyl)phenyl)(piperazin-1-yl)methanone (KW-2449), 2Z,3E)-6'-bromo-3-(hydroxyimino)-[2,3'-biindolinylidene]-2'-one (KIN 001-043), N-(2-diethylaminoethyl)-5-[(Z)-(5-fluoro-2-oxo-1H-indol-3-ylidene)methyl]-2,4-dimethyl-1H-pyrrole-3-carboxamide (Sunitinib), 1-(2-(5-(2-(3-methyl-oxetan-3-yl)ethyl)-1H-benzo[d]imidazol-1-yl)quinolin-8-yl)piperidin-4-amine (Crenolanib), N'-[4-[(6,7-dimethoxy-4-quinolinyl)oxy]phenyl]-N-(4-fluorophenyl)-1,1-cyclopropanedicarboxamide (XL-184), 3-((6-(3-aminophenyl)-7H-pyrrolo[2,3-d]pyrimidin-4-yl)methyl) phenol (TWS-119), (2Z,3E)-3-(hydroxyimino)-[2,3'-biindolinylidene]-2'-one (Indirubin-monoxime), resveratrol, piperine, and salts thereof. In certain embodiments, the subject is administered a therapeutically effective amount of a compound selected from the group consisting of, MET proto-oncogene, receptor tyrosine kinase (MET) inhibitors. In certain embodiments the compound is selected from the group of compounds listed in Table 2 and salts thereof. In certain embodiments the compound is selected from the group of compounds listed in Table 3 and salts thereof.

In certain embodiments, a pharmaceutical composition is used to treat a subject with a neurological disease, psychiatric disorder, or central nervous system (e.g., brain) injury. In certain embodiments, the pharmaceutical composition comprises of a compound selected from the group consisting of kinase inhibitors, Feline McDonough sarcoma-like tyrosine kinase 3 (FLT3) inhibitors, glycogen synthase kinase 3 (GSK3) inhibitors, gamma-aminobutyric acid (GABA) inhibitors, GABA reuptake inhibitors, monoamine oxidase inhibitors (MAOI), norepinephrine reuptake inhibitor (NRI), dopamine antagonist, Sirtuin 1 (SIRTI) activators, transient receptor potential cation channel subfamily V member 1 (TRPV1) activators, monoamine transporter activators, tropomyosin receptor kinase B (TrkB) agonists, ampakines, and pharmaceutically acceptable salts thereof. In certain embodiments, the pharmaceutical composition comprises a compound selected from the group consisting of (E)-(4-(2-(1H-indazol-3-yl)vinyl)phenyl)(piperazin-1-yl)methanone (KW-2449), 2Z,3E)-6'-bromo-3-(hydroxyimino)-[2,3'-biindolinylidene]-2'-one (KIN 001-043), N-(2-diethylaminoethyl)-5-[(Z)-(5-fluoro-2-oxo-1H-indol-3-ylidene)methyl]-2,4-dimethyl-1H-pyrrole-3-carboxamide (Sunitinib), 1-(2-(5-(2-(3-methyloxetan-3-yl)ethyl)-1H-benzo[d]imidazol-1-yl)quinolin-8-yl)piperidin-4-amine (Crenolanib), N'-[4-[(6,7-dimethoxy-4-quinolinyl)oxy]phenyl]-N-(4-fluorophenyl)-1,1-cyclopropanedicarboxamide (XL-184), 3-((6-(3-aminophenyl)-7H-pyrrolo[2,3-d]pyrimidin-4-yl)methyl)phenol (TWS-119), (2Z,3E)-3-(hydroxyimino)-[2,3'-biindolinylidene]-2'-one (Indirubin-monoxime), resveratrol, piperine, and salts thereof. In certain embodiments, the compound is selected from the group consisting of, MET proto-oncogene, receptor tyrosine kinase (MET) inhibitors. In certain embodiments the compound is selected from the group of compounds listed in Table 2 and salts thereof. In certain embodiments the compound is selected from the group of compounds listed in Table 3 and salts thereof. In certain embodiments, the pharmaceutical composition comprises a pharmaceutically acceptable excipient.

In certain embodiments, a kit is provided, which comprises a compound selected from the group consisting of kinase inhibitors, Feline McDonough sarcoma-like tyrosine kinase 3 (FLT3) inhibitors, glycogen synthase kinase 3 (GSK3) inhibitors, gamma-aminobutyric acid (GABA) inhibitors, GABA reuptake inhibitors, monoamine oxidase inhibitors (MAOI), porepinephrine reuptake inhibitor (NRI), dopamine antagonist, Sirtuin 1 (SIRT1) activators, transient receptor potential cation channel subfamily V member 1 (TRPV1) activators, monoamine transporter activators, tropomyosin receptor kinase B (TrkB) agonists, ampakines, and pharmaceutically acceptable salts thereof. In certain embodiments, the compound is selected from the group consisting of (E)-(4-(2-(1H-indazol-3-yl)vinyl)phenyl)(piperazin-1-yl)methanone (KW-2449), 2Z,3E)-6'-bromo-3-(hydroxyimino)-[2,3'-biindolinylidene]-2'-one (KIN 001-043), N-(2-diethylaminoethyl)-5-[(Z)-(5-fluoro-2-oxo-1H-indol-3-ylidene)methyl]-2,4-dimethyl-1H-pyrrole-3-carboxamide (Sunitinib), 1-(2-(5-(2-(3-methyloxetan-3-yl)ethyl)-1H-benzo[d]imidazol-1-yl)quinolin-8-yl)piperidin-4-amine (Crenolanib), N'-[4-[(6,7-dimethoxy-4-quinolinyl)oxy]phenyl]-N-(4-fluorophenyl)-1,1-cyclopropanedicarboxamide (XL-184), 3-((6-(3-aminophenyl)-7H-pyrrolo[2,3-d]pyrimidin-4-yl)methyl)phenol (TWS-119), (2Z,3E)-3-(hydroxyimino)-[2,3'-biindolinylidene]-2'-one (Indirubin-monoxime), resveratrol, piperine, and salts thereof. In certain embodiments, the compound is selected from the group consisting of, MET proto-oncogene, receptor tyrosine kinase (MET) inhibitors. In certain embodiments the compound is selected from the group of compounds listed in Table 2 and salts thereof. In certain embodiments the compound is selected from the group of compounds listed in Table 3 and salts thereof. In certain embodiments, the kit consists instructions for administering a compound, the pharmaceutically acceptable salt thereof, or the pharmaceutical composition.

In some aspects, the present disclosure provides compounds, compositions, and kits described herein for the use in a method of the present disclosure.

The details of certain embodiments of the invention are set forth in the Detailed Description of Certain Embodiments, as described below. Other features, objects, and advantages of the invention will be apparent from the Definitions, Examples, Figures, and Claims.

DEFINITIONS

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., Tetrahedron 33:2725 (1977); Eliel, E. L. *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, IN 1972). The invention additionally encompasses compounds as individual isomers substantially free of other isomers, and alternatively, as mixtures of various isomers.

In a formula, ⁓ is a single bond where the stereochemistry of the moieties immediately attached thereto is not specified, --- is absent or a single bond, and === or ⁼⁼⁼ is a single or double bond.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}$F with $^{18}$F, or the replacement of a carbon by a $^{13}$C- or $^{14}$C-enriched carbon are within the scope of the disclosure. Such compounds are useful, for example, as analytical tools or probes in biological assays.

When a range of values is listed, it is intended to encompass each value and subrange within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —CH$_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu or s-Bu), unsubstituted isobutyl (i-Bu)). In certain embodiments, the alkyl group is a substituted $C_{1-10}$ alkyl (such as substituted $C_{1-6}$ alkyl, e.g., —CH$_2$F, —CHF$_2$, —CF; or benzyl (Bn)).

The term "haloalkyl" is a substituted alkyl group, wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include —CF$_3$, —CF$_2$CF$_3$, —CF$_2$CF$_2$CF$_3$, —CCl$_3$, —CFCl$_2$, —CF$_2$Cl, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("heteroC$_{1-10}$ alkyl"). In some embodiments, a heteroalkyl group is a saturated group having 1 to 9 carbon atoms and 1 or more heteroatoms within the parent chain ("heteroC$_{1-9}$ alkyl"). In some embodiments, a heteroalkyl group is a saturated group having 1 to 8 carbon atoms and 1 or more heteroatoms within the parent chain ("heteroC$_{1-8}$ alkyl"). In some embodiments, a heteroalkyl group is a saturated group having 1 to 7 carbon atoms and 1 or more heteroatoms within the parent chain ("heteroC$_{1-7}$ alkyl"). In some embodiments, a heteroalkyl group is a saturated group having 1 to 6 carbon atoms and 1 or more heteroatoms within the parent chain ("heteroC$_{1-6}$ alkyl"). In some embodiments, a heteroalkyl group is a saturated group having 1 to 5 carbon atoms and 1 or 2 heteroatoms within the parent chain ("heteroC$_{1-5}$ alkyl"). In some embodiments, a heteroalkyl group is a saturated group having 1 to 4 carbon atoms and 1 or 2 heteroatoms within the parent chain ("heteroC$_{1-4}$ alkyl"). In some embodiments, a heteroalkyl group is a saturated group having 1 to 3 carbon atoms and 1 heteroatom within the parent chain ("heteroC$_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl (C$_9$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted C$_{2-10}$ alkenyl. In certain embodiments, the alkenyl group is a substituted C$_{2-10}$ alkenyl. In an alkenyl group, a C=C double bond for which the stereochemistry is not specified (e.g., —CH=CHCH$_3$,

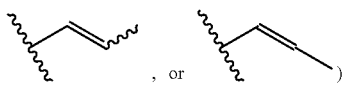

, or

)

may be in the (E)- or (Z)-configuration.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group bas 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 10 ring carbon atoms ("C$_{3-10}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl. In certain embodiments, the carbocyclyl includes 0, 1, or 2 C=C double bonds in the carbocyclic ring system, as valency permits.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl. In certain embodiments, the heterocyclyl is substituted or unsubstituted, 3- to 7-membered, monocyclic heterocyclyl, wherein 1, 2, or 3 atoms in the heterocyclic ring system are independently oxygen, nitrogen, or sulfur, as valency permits.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetra-hydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). In certain embodiments, the heteroaryl is substituted or unsubstituted, 5- or 6-membered, monocyclic heteroaryl, wherein 1, 2, 3, or 4 atoms in the heteroaryl ring system are independently oxygen, nitrogen, or sulfur. In certain embodiments, the heteroaryl is substituted or unsubstituted, 9- or 10-membered, bicyclic heteroaryl, wherein 1, 2, 3, or 4 atoms in the heteroaryl ring system are independently oxygen, nitrogen, or sulfur.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively.

Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group substituted by a heteroaryl group, wherein the point of attachment is on the alkyl moiety.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moicty of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{3-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$—C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

In certain embodiments, the carbon atom substituents are independently halogen, substituted or unsubstituted C$_{1-6}$ alkyl, —OR$^{aa}$, —SR$^{aa}$, —N(R$^{bb}$)$_2$, —CN, —SCN, —NO$_2$, —C(=O)R$^{aa}$, —CO$_2$R$^{aa}$, —C(=O)N(R$^{bb}$)$_2$, —OC(=O)R$^{aa}$, —OCO$_2$R$^{aa}$, —OC(=O)N(R$^{bb}$)$_2$, —NR$^{bb}$(=O)R$^{aa}$, —NR$^{bb}$CO$_2$R$^{aa}$, or —NR$^{bb}$C(=O)N(R$^{bb}$)$_2$. In certain embodiments, the carbon atom substituents are independently halogen, substituted or unsubstituted C$_{1-6}$ alkyl, —OR$^{aa}$, —SR$^{aa}$, —N(R$^{bb}$)$_2$, —CN, —SCN, or —NO$_2$.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O) SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$, —OP(=O)$_2$R$^{aa}$, —OP(=O)(R$^{aa}$)$_2$, —OP(⊙O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein.

The term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —SR$^{aa}$, —S=SR$^{cc}$, —SC(=S)SR$^{aa}$, —SC(=O)SR$^{aa}$, —SC(=O)OR$^{aa}$, and —SC(=O)R$^{aa}$, wherein R$^{aa}$ and R$^{cc}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(NR$^{bb}$)$_2$, wherein R$^{aa}$, R$^{bb}$ and R$^{cc}$ are as defined herein, and wherein R$^{bb}$ of the group —NH(R$^{bb}$) is not hydrogen.

The term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N ($R^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O))(NR$^{bb}$)$_2$, wherein R$^{aa}$, R$^{bb}$, and R$^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3$$^+$X$^-$, wherein R$^{bb}$ and X$^-$ are as defined herein.

The term "sulfonyl" refers to a group selected from —SO$_2$N(R$^{bb}$)$_2$, —SO$_2$R$^{aa}$, and —SO$_2$OR$^{aa}$, wherein R$^{aa}$ and R$^{bb}$ are as defined herein.

The term "sulfinyl" refers to the group —S(=O)R$^{aa}$, wherein R$^{aa}$ is as defined herein.

The term "carbonyl" refers a group wherein the carbon directly attached to the parent molecule is sp$^2$ hybridized, and is substituted with an oxygen, nitrogen or sulfur atom, e.g., a group selected from ketones (—C(=O)R$^{aa}$), carboxylic acids (—CO$_2$H), aldehydes (—CHO), esters (—CO$_2$R$^{aa}$, —C(=O)SR$^{aa}$, —C(=S)SR$^{aa}$), amides (—C(=O)N(R$^{bb}$)$_2$, —C(=O)NR$^{bb}$SO$_2$R$^{aa}$, —C(=S)N(R$^{bb}$)$_2$), and imines (—C(=NR$^{bb}$)R$^{aa}$, —C(=NR$^{bb}$)OR$^{aa}$, —C(=NR$^{bb}$)N(R$^{bb}$)$_2$), wherein R$^{aa}$ and R$^{bb}$ are as defined herein.

The term "silyl" refers to the group —Si(R$^{aa}$)$_3$, wherein R$^{aa}$ is as defined herein.

The term "boronyl" refers to boranes, boronic acids, boronic esters, borinic acids, and borinic esters, e.g., boronyl groups of the formula —B(R$^{aa}$)$_2$, —B(OR$^{cc}$)$_2$, and —BR$^{aa}$(OR$^{cc}$), wherein R$^{aa}$ and R$^{cc}$ are as defined herein.

The term "phosphino" refers to the group —P(R$^{cc}$)$_3$, wherein R$^{cc}$ is as defined herein. An exemplary phosphino group is triphenylphosphine.

The term "phosphono" refers to the group —O(P=O)(OR$^{cc}$)R$^{aa}$, wherein R$^{aa}$ and R$^{cc}$ are as defined herein.

The term "phosphoramido" refers to the group —O(P=O)(NR$^{bb}$)$_2$, wherein each R$^{bb}$ is as defined herein.

The term "stannyl" refers to the group —Sn(R$^{cc}$)$_3$, wherein R$^{cc}$ is as defined herein.

The term "germyl" refers to the group —Ge(R$^{cc}$)$_3$, wherein R$^{cc}$ is as defined herein.

The term "arsenyl" refers to the group —As(R$^{cc}$)$_3$, wherein R$^{cc}$ is as defined herein.

The term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered beteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl- 2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1.4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fem), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfonamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, 1-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4 dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

The term "heteroatom" refers to an atom that is not hydrogen or carbon. In certain embodiments, the heteroatom is nitrogen. In certain embodiments, the heteroatom is oxygen. In certain embodiments, the heteroatom is sulfur.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs); and birds (e.g., commercially relevant birds such as chickens, ducks, geese, and/or turkeys). In certain embodiments, the animal is a mammal. In certain embodiments, the animal is a mouse. In certain embodiments, the animal is a human. The animal may be a male or female at any stage of development. The animal may be a transgenic animal or genetically engineered animal. In certain embodiments, the subject is a non-human animal.

The term "administer," "administering," or "administration" refers to implanting, absorbing, ingesting, injecting, inhaling, or otherwise introducing a compound or cell described herein or generated as described herein, or a composition thereof, in or on a subject.

The terms "treatment," "treat," and "treating" refer to reversing, alleviating, delaying the onset of, or inhibiting the progress of a disease. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen and/or in light of detecting that the subject has a genotype associated with the disease). Treatment may also be continued after symptoms have resolved, for example, to delay or prevent recurrence.

The terms "condition," "disease," and "disorder" are used interchangeably.

The term "stem cell" refers to a vertebrate cell that has the ability both to self-renew, and to generate differentiated progeny. The ability to generate differentiated progeny of all three germ layers may be described as pluripotent (see Morrison et al. (1997) Cell 88:287-298). "Embryonic stem cells" (ES cells) are pluripotent stem cells derived from the inner cell mass of an early-stage preimplantation embryo, e.g., a morula or blastocyst. Pluripotency distinguishes embryonic stem cells from adult stem cells found in adults; while embryonic stem cells can generate all cell types in the body, adult stem cells are multipotent and can produce only a limited number of cell types.

As used herein, the term "salt" refers to any and all salts, and encompasses pharmaceutically acceptable salts.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

An "effective amount" of a compound described herein refers to an amount sufficient to elicit the desired biological response, i.e., treating the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutic and prophylactic treatment. For example, in treating a neurological disease, psychiatric disorder, or central nervous system injury characterized by deficient expression or function of KCC2, an effective amount of a compound may correct or improve the deficient expression or function of KCC2.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, and/or enhances the therapeutic efficacy of another therapeutic agent.

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than about 1,000 g/mol, not more than about 900 g/mol, not more than about 800 g/mol, not more than about 700 g/mol, not more than about 600 g/mol, not more than about 500 g/mol, not more than about 400 g/mol, not more than about 300 g/mol, not more than about 200 g/mol, or not more than about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and not more than about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention.

The term "inhibition," "inhibiting," "inhibit," or "inhibitor" refers to the ability of a compound to reduce, slow, halt or prevent activity of a particular biological process (e.g., kinase activity) in a cell.

The term "gene" refers to a nucleic acid fragment capable of synthesizing a gene product. In certain embodiments, the nucleic acid fragment includes regulatory sequences preceding and following the coding sequence. "Native gene" refers to a gene as found in nature with its own regulatory sequences. "Chimeric gene" or "chimeric construct" refers to any gene or a construct, not a native gene, comprising regulatory and coding sequences that are not found together in nature. Accordingly, a chimeric gene or chimeric construct may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but which is introduced into the host organism by gene transfer. Foreign genes can comprise native genes inserted into a non-native organism, or chimeric genes. A "transgene" is a gene that has been introduced into the genome by a transformation procedure.

The term "reporter" refers to a gene attached to a regulatory sequence of another gene of interest in bacteria, cell culture, animals, or plants. Reporter genes are often used as an indication of whether a certain gene has been taken up by or expressed in the cell or organism population.

The term "neurological disease" refers to any disease of the nervous system, including diseases that involve the central nervous system (brain, brainstem and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including, but not limited to, Alzheimer's disease, Parkinson's disease, amyotrophic lateral sclerosis, tauopathies (including frontotemporal dementia), and Huntington's disease. Examples of neurological diseases include, but are not limited to, headache, stupor and coma, dementia, seizure, sleep disorders, trauma, infections, neoplasms, neuro-ophthalmologic disorders, movement disorders, demyelinating diseases, spinal cord disorders, and disorders of peripheral nerves, muscle and neuromuscular junctions. Addiction and mental illness, include, but are not limited to, bipolar disorder, depression, and schizophrenia, and are also included in the definition of neurological diseases. Examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomie dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy (CIDP); chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome: encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); boloprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile; phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (aka motor neuron disease or amyotrophic lateral sclerosis); lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger syndrome.

The term "psychiatric disorder" refers to a disease of the mind and includes diseases and disorders listed in the Diagnostic and Statistical Manual of Mental Disorders—Fourth Edition (DSM-IV), published by the American Psychiatric Association, Washington D. C. (1994). Psychiatric disorders include, but are not limited to, anxiety disorders (e.g., acute stress disorder agoraphobia, generalized anxiety disorder, obsessive-compulsive disorder, panic disorder, posttraumatic stress disorder, separation anxiety disorder, social phobia, and specific phobia), childhood disorders, (e.g., attention-deficit/hyperactivity disorder, conduct disorder, and oppositional defiant disorder), eating disorders (e.g., anorexia nervosa and bulimia nervosa), mood disorders (e.g., depression, bipolar disorder, cyclothymic disorder, dysthymic disorder, and major depressive disorder), personality disorders (e.g., antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder), psychotic disorders (e.g., brief psychotic disorder, delusional disorder, schizoaffective disorder, schizophreniform disorder, schizophrenia, and shared psychotic disorder), substance-related disorders (e.g., alcohol dependence, amphetamine dependence, cannabis dependence, cocaine dependence, hallucinogen dependence, inhalant dependence, nicotine dependence, opioid dependence, phencyclidine dependence, and sedative dependence), adjustment disorder, autism, delirium, dementia, multi-infarct dementia, learning and memory disorders (e.g., amnesia and age-related memory loss), and Tourette's disorder.

BRIEF DESCRIPTION OF THE DRAWINGS

The accompanying drawings, which constitute a part of this specification, illustrate several exemplary embodiments of the invention and together with the description, serve to explain certain principles of the invention. The embodiments disclosed in the drawings are exemplary and do not limit the scope of this disclosure.

FIG. 1A shows a diagram showing the gene targeting strategy to insert a luciferase reporter gene into the KCC2 locus of human RTT ESC. FIG. 1B shows the workflow of a compound screening experiment. The cell lysate was divided into two parts to measure luciferase signal (KCC2 translation) and Cell-Titer Glow (CTG, amount of ATP). The luciferase signal was normalized to CTG for each well, and the Luc/CTG ratio was normalized to the in-plate DMSO negative control to calculate fold change ratio. FIG. 1C shows RTT KCC2 reporter neurons screening results with LINCS (Library of Integrated Network-based Cellular Signatures) kinase inhibitor library (see, e.g., Haston, K. M. et. al., Annu Rev Pharmacol Toxicology, 2016, 56, 489-510; Fuller, H. R. et al., Frontiers in Cellular Neuroscience, 2016, 9, 1-15; Milani, P. et al., Scientific Reports, 2016, 6, 1-12). The structure of hit compounds KW-2449, KIN 001-043 are provided. FIG. 1D shows sample data of RTT KCC2 reporter neurons screening results with IRSF (International Rett Syndrome Foundation) SMART (Selected Molecular Agents for Rett Therapy) compound library (rettsyndrome-.org/for-researchers/smart-library).

FIG. 2A shows that KW-2449 treatment significantly increases KCC2 expression in RTT neurons at concentrations as low as 0.1 µM. FIG. 2B shows that KIN 001-043 treatment significantly increases KCC2 expression in RTT neurons at a concentration of 0.3 µM. FIG. 2C shows that Resveratrol treatment significantly increases KCC2 expression in RTT neurons at a concentration of 10 µM. FIG. 2D shows that Piperine treatment significantly increases KCC2 expression in RTT neurons at a concentration of 10 µM.

FIGS. 3A to 3B show two functional analogs of hit compound KW-2449, Crenolanib (FIG. 3A) and XL-184 (FIG. 3B), which both inhibit FLT3 kinase activity and increase KCC2 expression when applied to RTT human neuron culture. FIG. 3C shows Indirubin-monoxime, a structural analog of hit compound KIN 001-043 that only differs at a Bromide residue, induces a significant increase in KCC2 expression in RTT neurons. FIG. 3D shows TWS-119, a functional analog of hit compound KIN 001-043 that inhibits the GSK3β pathway, induces a significant increase in KCC2 expression in RTT neurons. FIG. 3E shows that the KCC2-enhancing effect of hit compound Resveratrol could be blocked by the SIRT1 pathway inhibitor EX-527. FIG. 3F shows that the KCC2-enhancing effect of hit compound Piperine could be blocked by the TRPV1 channel inhibitor A784168.

FIGS. 4A to 4D show four hit compounds KW-2449 (FIG. 4A), Sunitinib (FIG. 4B), XL-184 (FIG. 4C), and Crenolanib (FIG. 4D), which all inhibit FLT3 kinase activity and increase KCC2 expression when applied to WT human neuron culture. FIG. 4E shows the hit compound TWS-119, which inhibits GSK3β and induces significant increase in the KCC2 expression in RTT neurons.

FIGS. 5A to 5B show that the treatment of KW-2449 (FIG. 5A), Crenolanib (FIG. 5B), and XL-184 (FIG. 5B), which are inhibitors of FLT3 kinase activity, to organotypical brain slices prepared from neonatal mice significantly increases KCC2 expression, in comparison to DMSO (FIG. 5A) or medium-treated control groups (FIG. 5B). FIG. 5C shows the treatment of KIN 001-043 (BIO) to brain slices increases KCC2 expression, while the treatment with an inactive analog of KIN 001-043 (MeBIO) does not affect KCC2 expression.

FIG. 6A is a diagram depicting the compound screening platform: A 2A-luciferase gene expression reporter was inserted in-frame before the endogenous stop codon of KCC2 gene in human ES cells. Luciferase activity faithfully reflects the expression level of KCC2 in the KCC2 reporter human neurons differentiated from the gene-targeted ES cells. FIG. 6B shows an unbiased screening of 929 small molecule compounds from LINCS, SMART, and ICCB drug libraries identified 14 potential KCC2 expression-enhancing compounds (B score >3). FIG. 6C shows that the identified hit compounds induce significant increases in KCC2 reporter signal compared to in-plate DMSO negative control. Compound data were color-coded according to their library-of-origin. FIG. 6D shows that hit KEEC KW-2449 (an inhibitor of FLT3 kinase) increases KCC2 protein level in cultured WT human neurons in a dose-dependent manner. FIG. 6E shows that hit KEEC BIO (6-bromoindirubin-3'-oxime) treatment increases KCC2 expression, while an inactive analog MeBIO (Methylated BIO) did not affect KCC2 expression in cultured human neurons. FIGS. 6F to 6H show that three chemical compounds that are functionally analogous to hit KEEC KW-2449, including Crenolanib, XL-184, and Sunitinib, induce a significant increase in KCC2 expression in cultured human RTT neurons. FIG. 6I shows that TWS-119, a functional analog of hit compound BIO, induces a significant increase in KCC2 expression in RTT neurons. Data are presented as mean±SEM. * $p<0.05$,  $p<0.01$, * $p<0.001$, determined by one-way ANOVA.

FIGS. 7B and 7C shows that reading luciferase signal from KCC2 luciferase reporter neurons in a dilution series generates a graded luciferase response. Data shown as mean±SEM.

FIG. 8A is a diagram depicting the experimental scheme: organotypic brain slices were prepared from P3 neonatal mouse brain, and treated with vehicle or KEECs for 7 days before analysis. FIG. 8B shows that treatment of organotypic mouse brain slices with hit KEEC KW-2449 significantly enhances KCC2 expression. FIG. 8C shows that treatment of brain slices with BIO significantly enhances KCC2 expression, while inactive analog MeBIO does not alter KCC2 expression. FIG. 8C shows that treatment of organotypic brain slices prepared from neonatal mice with Crenolanib or XL-184 significantly increases KCC2 expression. FIGS. 8E to 8F show results of quantitative RT-PCR experiments showing a significant increase in the KCC2 mRNA level and a significant reduction in NKCC1 mRNA level, in brain slices treated with FLT3 inhibitors, Sunitinib, XL-184, Crenolanib, or a structural analog of BIO termed indirubin monoxime. n=3 independent biological repeats per group. FIG. 8G depicts representative gramicidin-perforated patch recording results showing the responses to GABA recorded from neonatal mouse neurons cultured for 6 days in vitro (DIV6) and treated with KEECs or controls. Dashed lines indicate GABA reversal potential ($E_{GABA}$) in each condition. FIG. 8H presents quantified results showing that treatment of DIV6 cultured mouse neurons with KEECs KW-2449, BIO, XL-184, or TWS-119 induces significant hyperpolarizing shift in $E_{GABA}$. Data are presented as mean±SEM. * $p<0.05$,  $p<0.01$, * $p<0.001$, determined by one-way ANOVA.

FIG. 10A shows results of an unbiased screening of 929 small molecule compounds from LINCS, SMART, and ICCB drug libraries identified 30 hit compounds that generate a B score>3. FIG. 10B shows that the identified hit compounds induce significant increases in KCC2 reporter signal comparing to in-plate DMSO negative control. FIGS. 10C, 10E, 10G, and 10H show that treatment of RTT neurons with hit KEEC KW-2449 and analog compounds Crenolanib and XL-184, and FLT3 inhibitor-I lead to significant increase in KCC2 expression. FIGS. 10D and 10F show that treatment of RTT neurons with hit KEEC BIO and the analog compounds indirubin monoxiome lead to significant increase in KCC2 expression. FIG. 10I shows that reatment of RTT neurons with Resveratrol increased KCC2 expression; while the additional application of the SIRT1 pathway inhibitor EX-527 blocked KCC2 expression enhancement. FIG. 10J shows that treatment of RTT neuron neurons with Piperine induced KCC2 expression in a dose-dependent manner. FIG. 10K shows that treatment of RTT neurons with Piperine increased KCC2 expression; while the additional application of the TRPV1 pathway inhibitor A784168 blocked KCC2 expression enhancement. Data are presented as mean±SEM. * $p<0.05$,  $p<0.01$, * $p<0.001$, determined by one-way ANOVA.

FIGS. 11A to 11C show that knocking down mouse Flt3 gene or Gsk3β gene in cultured DIV6 immature mouse neurons significantly increase KCC2 gene expression comparing to non-transfected neurons. FIGS. 11D to 11F show that knocking down human FLT3 gene or GSK3β gene in cultured one-month human RTT neurons significantly increase KCC2 gene expression comparing to non-transfected neurons. Data is presented as mean±SEM, * $p<0.05$, ** $p<0.01$, determined by one-way ANOVA.

FIG. 12A presents representative gramicidin-perforated patch recording results showing the responses to GABA recorded from human neurons derived from MECP2 knockout human neurons and treated with KEECs or controls. Dashed lines indicate $E_{GABA}$ in each condition. FIG. 12B presents quantified results showing that treatment of RTT with KEECs KW-2449 or BIO, but not the inactive analog MeBIO, induces significant hyperpolarizing shift in $E_{GABA}$. Knocking down KCC2 with shRNA transfection abolishes the $E_{GABA}$ changes induced by KW-2449 or BIO. #$p<0.05$, comparing to the KW-2449- or BIO-treated groups without shRNA transfection. FIGS. 12C to 12H show that the frequency of mEPSC is significantly reduced in RTT neurons (FIG. 12D) compared to isogenic #38 WT neurons (FIG. 12C). Treatment of RTT neurons with KEECs KW-2449 (FIG. 12E) or BIO (FIG. 12F), but not the inactive analog MeBIO (FIG. 12G), significantly increased the frequency of mEPSC. Knocking down KCC2 with shRNA transfection abolishes the mEPSC changes induced by KW-2449 or BIO. #$p<0.05$, ###$p<0.001$, comparing to the KW-2449- or BIO-treated groups without shRNA transfection. Quantified results are shown in (FIG. 12H). Data are presented as mean±SEM. * $p<0.05$,  $p<0.01$, * $p<0.001$, determined by one-way ANOVA.

FIGS. 14A to 14D show representative MAP2-stained dendritic morphology traces reconstructed from RTT neurons treated with DMSO, KW-2449, BIO or MeBIO. FIG. 14E shows Sholl analysis show that treatment of RTT neurons with KW-2449 or BIO induce significant increase in neurite complexity comparing to DMSO- or MeBIO-treated control groups. FIGS. 14F to 14H show that reatment with KW-2449 or BIO significantly increase the nucleus size (FIG. 14F), total neurite length (FIG. 14G), and the number of neurite branches (FIG. 14H) in RTT neurons. Data are presented as mean±SEM. * $p<0.05$,  $p<0.01$, * $p<0.001$, determined by t-test.

FIG. 15A is a diagram depicting the plethysmograph measurement setup. FIGS. 15N to 15L show representative night-time locomotion activity time series heatmap for EtOH injected (FIG. 15L) and KEEC Piperine injected (FIG. 15M) Mecp2 mutant animals. Injection of Piperine significantly increased day-time locomotion in Mecp2 mutant animals comparing to EtOH control (FIG. 15N). * $p<0.05$, ** $p<0.01$, determined by paired t-test with Bonferroni correction when applicable.

DETAILED DESCRIPTION OF CERTAIN EMBODIMENTS

Figure 1A:
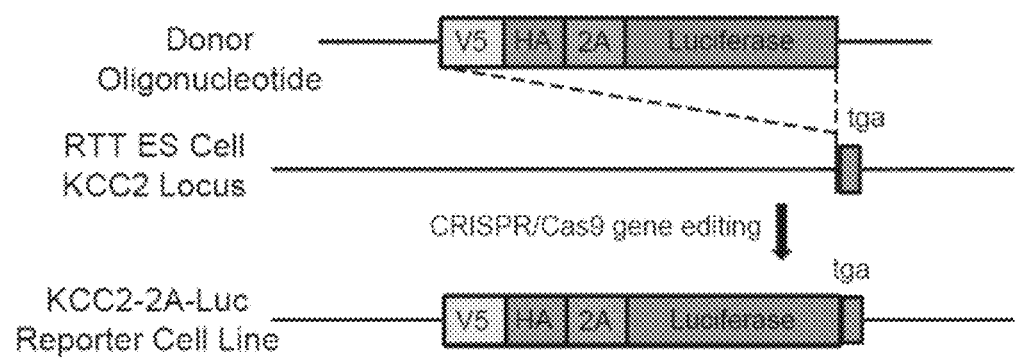
FIGS. 1A to 1D show the development of a screening platform with RTT KCC2-2A-luciferase reporter neurons to identify KCC2 expression enhancing compounds.

The present disclosure provides methods, compounds, compositions, and kits focused on the identification, validation, and use of compounds to treat various neurological diseases, psychiatric disorders, and central nervous system injuries characterized by deficient expression of KCC2 (e.g., ASD, RTT, epilepsy, schizophrenia, mental retardation, stroke, Fragile-X syndrome, traumatic brain injury, and spinal cord injury). KCC2 has proven to be a critical gene for proper brain function and for the survival of the organism. Global knockout of KCC2 gene in mouse model leads to death at birth (Hubner et al., *Neuron*, 2001, 30, 515-24). Less severe types of KCC2-deficient animal model (KCC2 hypomorph) have been developed, in which massive brain development defect have led to behavior abnormalities (Tomberg, J. et al., *Eur. J. Neurosci.*, 2005, 21, 1327-37). Impaired electrophysiology properties have been documented in these animals (Riekki, R. et al., *J. Neurophysiol.*, 2008, 99, 3075-89). Since complete lack of KCC2 is incompatible with life, there has only been a few reports of rare cases of human ASD patients carrying relatively mild mutations including R952H, R1049C, R1048W, in the C-terminus regulatory region of KCC2 gene. Mutation R952H has also been described in schizophrenia patients (Merner, N. D. et al., *Front. Cell. Neurosci.*, 2015, 9, 1-10). However, disruptions in KCC2 expression and/or function have been documented in many neurological disorders.

Animal models with KCC2 deficiency develop pathological features similar to those observed in MECP2 knockout mouse including breathing irregularity (Hubner et al., *Neuron*, 2001, 30, 515-24), smaller body weight (Tornberg, J. et al., *Eur. J. Neurosci.*, 2005, 21, 1327-37), and impaired learning and memory (Tornberg, J. et al., *Eur. J. Neurosci.*, 2005, 21, 1327-37). On the other hand, NKCC1 knockout mouse model suffers from heightened anxiety, imbalance, and severe deafness (29; Flagella, M. et al., *J. Biol. Chem.*, 1999, 274, 26946-55). These phenotypes are strikingly similar to mouse model of MECP2 duplication syndrome (Na, E. S. et al., *J. Neurosci.*, 2012, 32, 3109-17; Samaco, R. C. et al., *Nat. Genet.*, 2012, 44, 206-11), and to the human MECP2 duplication syndrome patient (Van Esch, H. et al., *Am. J. Hum. Genet.*, 2005, 77, 442-53; del Gaudio, D. et al., *Genet. Med.*, 2006, 8, 784-92). Previous work (Tang, X. et al., *PNAS*, 2016, 113, 751-756) has utilized iPS cell-derived human neurons to establish developmental time courses of KCC2 expression and GABA functional switch in wild-type and Rett syndrome (RTT) neurons. It was found that human RTT neurons have a severe reduction in KCC2 expression and, consequently, deficits in both GABA functional switch and glutamatergic synapse development. The findings revealed a link between KCC2 and RTT, and may provide a novel framework to understand the pathological causes of autism spectrum disorders in general.

Since the discovery of KCC2 as the main regulator of neuronal chloride homeostasis in 1999 (Rivera, C. et al., *Nature*, 1999, 397, 251-5), one of the first diseases that has been linked to KCC2 deficit is epilepsy (Cohen, I. et al., *Science*, 2002, 298, 1418-21; Woo, N. S. et al., *Hippocampus*, 2002, 12, 258-68). Experimental evidence has pointed out that in the epileptic brain, the constant high level of neuronal activity can lead to a significant downregulation of KCC2 level, which in turn exacerbates the system overexcitation by reducing GABAergic inhibition (85-87). In human neonatal infants before one year of age, potentiating GABAergic neurotransmission actually exacerbates the epileptic condition (Dzhala, V. I. et al., *Nat. Med.*, 2005, 11, 1205-13). Treatment of neonatal seizure with bumetanide, a selective NKCC1 blocker, can reduce the intracellular chloride level and ameliorate seizure severity (neonatal seizure). However, bumetanide treatment has the side effect of causing hearing loss in some clinical cases. These findings highlight the contribution of GABA excitation to both normal human brain development and in neurological disorders. Reviews of recent progress in this field can be found in the following two articles (84; 2).

In the brain injury and stroke condition, the KCC2 expression level is also found to be significantly reduced around the transient focal cerebral ischemia loci (90). Without wishing to be bound by any theory, the underlying mechanism is likely to be through N-methyl-D-aspartate (NMDA)-mediated phosphorylation and internalization of KCC2 (Lee, H. H. et al., *Nat. Neurosci.*, 2011, 14, 736-743). During the stressful period of child-birth labor, the surge of oxytocin from the maternal bloodstream can lead to a temporary increase in KCC2 expression in the fetus, effectively preventing excitotoxicity and cell death during delivery (Khazipov, R. et al., *Prog. Brain Res.*, 2008, 170, 243-57). A rather comprehensive review of recent literature can be found in (Martín-Aragón Baudel, M. A., et al., *J. Neurochem.*, 2017, 140, 195-209).

In the cases of neuropsychiatric disorders, a disruption in KCC2 messenger ribonucleic acid (mRNA) level has been reported in schizophrenia patients (5; 4). Differences in expression levels of specific KCC2 transcripts have also been linked to schizophrenia and affective disorders (88). Mutation in the cell adhesion molecule critical for GABAergic synapse formation, neuroligin 2 (NL2), is found in schizophrenia patients. Unexpectedly, knockdown of NL2 can lead to a significant decrease in KCC2, suggesting KCC2's participation in the pathogenesis of some genetically-defined schizophrenia cases (Sun, C. et al., *Mol. Brain*, 2013, 6, 1-13). Altered KCC2 expression has also been implied in mediating stress axis behaviors (Hewitt, S. A. et al., *Nat. Neurosci.*, 2009, 12, 438-443). In two recent clinical studies, children with general autism spectrum disorders and children with Fragile-X syndrome, a specific monogenic form of autism (Hagerman, R. et al., *Molecular Autism*, 2010, 1, 1-14), can both be phenotypically treated with NKCC1 blocker bumetanide (76,77). Two recent research articles have described a delayed GABA functional switch in Fragile-X syndrome mouse model (He, K. et al., *Endokrynol Pol.*, 2014, 65, 485-90), valporate acid-induced autism model (74), and the alleviation of Fragile-X syndrome-related GABA functional switch deficit in the offspring by treating mutant mouse mother with oxytocin or bumetanide (74). These findings suggest the intriguing possibility that KCC2 dysfunction may be the core symptom and molecular underpinning responsible for various neurodevelopmental and neuropsychiatric disorders.

In the spinal cord, where the onset of KCC2 expression is the earliest during CNS development, disease-related downregulation of KCC2 can lead to various neurological conditions. After spinal cord injury, KCC2 downregulation in motor neurons leads to spasticity, a condition in which certain muscles are continually contracted (6). Similar spasticity can also be observed after intrathecal brain-derived neurotrophic factor (BDNF) injection since acute BDNF application is known to down-regulate KCC2. Interestingly, later application of BDNF to mouse model of spinal cord injury restores KCC2 expression and alleviates spasticity symptoms. Along the same vein, it has also been discovered that microglia-secreted BDNF down-regulates KCC2 in sensory neurons, leading to over-excitation of sensory neurons and neuropathic pain (Coull, J. A. et al., *Nature*, 2005, 438, 1017-21).

Although KCC2 expression levels has been linked to multiple neurological diseases, psychiatric disorders, and central nervous system injuries, as far as the inventors are aware, no small molecule chemical compound that is capable of increasing KCC2 expression in neurons has been identified prior to the present disclosure. Therefore, enhancing KCC2 expression is a promising pharmacological avenue to treat a variety of neurological diseases, psychiatric disorders, or central nervous system injuries. Without wishing to be bound by any theory, enhancing KCC2 expression may act at least in part through restoring the foundation of proper neural network function.

In certain embodiments, methods of treating a subject with a neurological disease, psychiatric disorder, and central nervous system injury characterized by deficient expression or function of KCC2 are described. In some embodiments the neurological disease, psychiatric disorder, or central nervous system injury is selected from the group consisting of ASD, RTT, epilepsy, schizophrenia, mental retardation, stroke, Fragile-X syndrome, traumatic brain injury, and spinal cord injury. In one embodiment, the subject has ASD. In one embodiment, the subject has RTT. In certain embodiments, methods of treating a subject with a neurodevelopmental disorder are described, the methods comprising administering a KCC2 expression enhancing compound to a subject having the disorder. In one embodiment the subject has RTT. In one embodiment the subject has Fragile-X syndrome. In one embodiment the subject has Down syndrome.

In certain embodiments, treating a subject comprises the step of administering to the subject a therapeutically effective amount of a small molecule that enhances expression of KCC2. In certain embodiments, treating a subject comprises the step of administering to the subject a therapeutically effective amount of a compound selected from the group consisting of kinase inhibitor, Feline McDonough sarcoma-like tyrosine kinase 3 (FLT3) inhibitors, glycogen synthase kinase 3 (GSK3) inhibitors, gamma-aminobutyric acid (GABA) inhibitors, GABA reuptake inhibitors, monoamine oxidase inhibitors (MAOI), porepinephrine reuptake inhibitor (NRI), dopamine antagonist, Sirtuin 1 (SIRT1) activators, transient receptor potential cation channel subfamily V member 1 (TRPV1) activators, monoamine transporter activators, tropomyosin receptor kinase B (TrkB) agonists, ampakines, and pharmaceutically acceptable salts thereof. In certain embodiments, the compound is selected from the group consisting of E)-(4-(2-(1H-indazol-3-yl)vinyl)phenyl)(piperazin-1-yl)methanone (KW-2449), 2Z,3E)-6'-bromo-3-(hydroxyimino)-[2,3'-biindolinylidene]-2'-one (KIN 001-043), N-(2-diethylaminoethyl)-5-[(Z)-(5-fluoro-2-oxo-1H-indol-3-ylidene)methyl]-2,4-dimethyl-1H-pyrrole-3-carboxamide (Sunitinib), 1-(2-(5-(2-(3-methyloxetan-3-yl)ethyl)-1H-benzo[d]imidazol-1-yl)quinolin-8-yl)piperidin-4-amine (Crenolanib), N'-[4-[(6,7-dimethoxy-4-quinolinyl)oxy]phenyl]-N-(4-fluorophenyl)-1,1-cyclopropanedicarboxamide (XL-184), 3-((6-(3-aminophenyl)-7H-pyrrolo[2,3-d]pyrimidin-4-yl)methyl)phenol (TWS-119), (2Z,3E)-3-(hydroxyimino)-[2,3'-biindolinylidene]-2'-one (Indirubin-monoxime), resveratrol, piperine, and salts thereof. In certain embodiments, the compound is selected from the group consisting of, MET proto-oncogene, receptor tyrosine kinase (MET) inhibitors. In certain embodiments the compound is selected from the group of compounds listed in Table 2 and salts thereof. In certain embodiments the compound is selected from the group of compounds listed in Table 3 and salts thereof.

In some aspects, a method of identifying a compound that modulates the level of KCC2 in a cell is described. In certain embodiments, the method comprises contacting a test compound with a cell; incubating the test compound with the cell for at least 24 hours under physiological conditions; and determining the expression level of KCC2 in the cell. In some embodiments, the compound is identified as a modulator of KCC2 expression if the expression level of KCC2 in the cell differs from the expression level of KCC2 in a control cell not contacted with the test compound. In some embodiments, the compound is identified as a KCC2 expression enhancing compound (KEEC) if the expression level of KCC2 in the cell is greater than the expression level of KCC2 in a control cell not contacted with the test compound. In some embodiments, the compound is identified as a KCC2 expression repressor compound (KERC) if the expression level of KCC2 in the cell is lower than the expression level of KCC2 in a control cell not contacted with the test compound.

In certain embodiments, the cells are neuronal cells. In certain embodiments, the neuronal cells are mammalian neuronal cells. In certain embodiments, the neuronal cells are human neuronal cells. In certain embodiments, the neuronal cells are primate neuronal cells. In certain embodiments, the neuronal cells are rodent neuronal cells. In certain embodiments, the neuronal cells are mouse neuronal cells. In certain embodiments, the neuronal cells are derived from embryonic stem cells. In certain embodiments the neuronal cells are derived from induced pluripotent stem (iPS) cells. In certain embodiments the neurons comprise excitatory neurons. In certain embodiments, the neuronal cells are wild-type KCC2 neurons. In certain embodiments, the neuronal cells are RTT cultured human neurons. In certain embodiments, the neuronal cell contains a reporter gene. In certain embodiment, the reporter gene is in the KCC2 locus. In some embodiments, the reporter gene is a luciferase reporter gene. In certain embodiments the reporter gene may be optimized for expression in mammalian cells.

In certain embodiments, the test compound is a nucleic acid. In certain embodiments, the test compound is a protein or peptide. In certain embodiments, the test compound is a small molecule. In certain embodiments the small molecule can be an organic molecule, or salt thereof. In certain embodiments, the test compound is selected from the group consisting of kinase inhibitors, Feline McDonough sarcoma-like tyrosine kinase 3 (FLT3) inhibitors, glycogen synthase kinase 3 (GSK3) inhibitors, gamma-aminobutyric acid (GABA) inhibitors, GABA reuptake inhibitors, monoamine oxidase inhibitors (MAOI), norepinephrine reuptake inhibitor (NRI), dopamine antagonist, Sirtuin 1 (SIRT1) activators, transient receptor potential cation channel subfamily V member 1 (TRPV1) activators, monoamine transporter activators, tropomyosin receptor kinase B (TrkB) agonists, ampakines, and salts thereof. In certain embodiments, the test compound is selected from the group consisting of, MET proto-oncogene, receptor tyrosine kinase (MET) inhibitors.

In certain embodiments, the cell is incubated with a test compound for at least 1 day. The incubation time can, for example, range between 1 day and 30 days. In certain embodiments, the incubation time described herein includes independently between 1 day and 7 days, between 7 days and 14 days, between 14 days and 21 days, between 21 days and 30 days, between 1 day and 3 days, between 3 days and 6 days, between 6 days and 9 days, between 9 days and 12 days, between 12 days and 15 days, between 15 days and 18 days, between 18 days and 21 days, between 21 days and 24 days, between 24 days and 27 days, or between 27 days and 30 days, inclusive. In one embodiment, the incubation time is approximately 14 weeks.

In certain embodiments, the concentration of the test compound while contacting the cell is between 0.1 nM and 1000 µM (1 M). In certain embodiments, concentration of the test compound while contacting the cell described herein includes independently between 0.1 nM and 1 nM, between 1 nM and 10 nM, between 10 nM and 100 nM (0.1 µM), between 0.1 µM and 1 µM, between 1 µM and 10 µM between 10 µM and 100 µM, between 100 µM and 200 µM, between 200 µM and 300 µM, between 300 µM and 400 µM, between 400 µM and 500 µM, between 500 µM and 600 µM, between 600 µM and 700 µM, between 700 µM and 800 µM, between 800 µM and 900 µM, or between 900 µM and 1000 µM. inclusive. In some embodiments, the concentration is approximately 10 µM.

In some embodiments, the cells are lysed after the incubation step. In certain embodiments the cell lysate is analyzed based upon a reporter assay to determine the expression level of KCC2. In certain embodiments, the reporter assays are selected from a group consisting of β-galactosidase reporter assay, chloramphenicol acetyltransferase reporter assay, fluorescent protein reporter assay (e.g., green fluorescent protein assay, red fluorescent protein assay, cyan fluorescent protein assay), and luciferase reporter assay. In certain embodiments the luciferase is firefly luciferase, sea pansy (*Renilla*) luciferase, *Gaussia* luciferase, or NanoLuc luciferase.

In some embodiments, the cells utilized are RTT KCC2-2A-luciferase reporter neurons. The neurons may be adapted to a multi-well format. In some embodiments, the neurons are adapted to a multi-well format. In some embodiments, the neurons are adapted to a 96-well format. In some embodiments, the neurons are adapted to a 384-well format. The cells, e.g., RTT KCC2-2A-luciferase reporter neurons, are then treated with a test compound library and incubated. The cells are then lysed, and, in some embodiments the cell lysate is divided into at least two parts, and a first part is used to measure reporter signal (indicative of KCC2 translation) and a second part is used to measure number of viable cells. The reporter signal for each well may be normalized to the signal indicative of the number of viable cells for that well, and the resulting ratio may be normalized to an in-plate negative control (e.g., a well containing a test compound vehicle, such as DMSO, and not a test compound) to calculate fold change ratio. For example, in some embodiments the cells are lysed, and the cell lysate is divided into two parts to measure luciferase signal (KCC2 translation) and Cell-Titer Glow (CTG, amount of ATP). The luciferase signal is normalized to CTG for each well, and the Luc/CTG ratio is normalized to the in-plate DMSO negative control to calculate fold change ratio. Any of a variety of assays may be used to measure the number of viable cells. For example, an assay that measures an indicator of metabolically active cells, such as ATP (e.g., a Cell-Titer Glo assay), may be used. Other assays that may be used in certain embodiments include tetrazolium reduction, resazurin reduction, and protease activity assays.

In certain embodiments, compounds are identified as KCC2 expression enhancing compounds (KEEC). In certain embodiments, the compound identified is selected from a group consisting of kinase inhibitors, Feline McDonough sarcoma-like tyrosine kinase 3 (FLT3) inhibitors, glycogen synthase kinase 3 (GSK3) inhibitors, gamma-aminobutyric acid (GABA) inhibitors, GABA reuptake inhibitors, monoamine oxidase inhibitors (MAOI), norepinephrine reuptake inhibitor (NRI), dopamine antagonist, Sirtuin 1 (SIRT1) activators, transient receptor potential cation channel subfamily V member 1 (TRPV1) activators, monoamine transporter activators, tropomyosin receptor kinase B (TrkB) agonists, ampakines, and salts thereof. In certain embodiments, the compound identified is selected from a group consisting of (E)-(4-(2-(1H-indazol-3-yl)vinyl)phenyl)(piperazin-1-yl)methanone (KW-2449), (2Z,3E)-6'-bromo-3-(hydroxyimino)-[2,3'-biindolinylidene]-2'-one (KIN 001-043), 1-(4-methoxybenzyl)-3-(5-nitrothiazol-2-yl)urea (AR-A014418), nipecotic acid, methysticin, trifluoperazine dihydrochloride, resveratrol, piperine, luteolin (flacitran), 7,8-dihydroxyflavone, 2,3,6a,7,8,9-hexahydro-11H-[1,4]dioxino[2',3':4,5]benzo[1,2-e]pyrrolo[2,1-b][1,3]oxazin-11-one (CX-614 or BDP37), N-(2-diethylaminoethyl)-5-[(Z)-(5-fluoro-2-oxo-1H-indol-3-ylidene)methyl]-2,4-dimethyl-1H-pyrrole-3-carboxamide (Sunitinib), 1-(2-(5-(2-(3-methyloxetan-3-yl)ethyl)-1H-benzo[d]imidazol-1-yl) quinolin-8-yl)piperidin-4-amine (Crenolanib), N'-[4-[(6,7-dimethoxy-4-quinolinyl)oxy]phenyl]-N-(4-fluorophenyl)-1,1-cyclopropanedicarboxamide (XL-184), 3-((6-(3-aminophenyl)-7H-pyrrolo[2,3-d]pyrimidin-4-yl)methyl) phenol (TWS-119), (2Z,3E)-3-(hydroxyimino)-[2,3'-biindolinylidene]-2'-one (Indirubin-monoxime). In certain embodiments, the compound is selected from the group consisting of, MET proto-oncogene, receptor tyrosine kinase (MET) inhibitors. In addition, the molecular pathways that the identified compounds act through to enhance KCC2 expression have been elucidated. Many of the hit compounds can be grouped into one or more of the following classes of compounds: Feline McDonough sarcoma-like tyrosine kinase 3 (FLT3) inhibitors, glycogen synthase kinase 3 (GSK3) inhibitors, gamma-aminobutyric acid (GABA) inhibitors, GABA reuptake inhibitors, monoamine oxidase inhibitors (MAOI), norepinephrine reuptake inhibitor (NRI), dopamine antagonist, Sirtuin 1 (SIRT1) activators, transient receptor potential cation channel subfamily V member 1 (TRPV1) activators, monoamine transporter activators, tropomyosin receptor kinase B (TrkB) agonists, and ampakines.

In some embodiments a compound is selective for a particular target versus one or more other potential targets. For example, in some embodiments the IC50 of the compound for inhibiting a first target (e.g., FLT3) may be at least 10-fold lower, at least 25-fold lower, at least 50-fold lower, or at least 100-fold lower than its IC50 for inhibiting a second kinase, using a comparable assay. In some embodiments a KEEC is selective for inhibiting FLT3 as compared with MET. In some embodiments the IC50 of a FLT3 inhibitor for inhibiting MET may be at least 100 nM, at least 1 micromolar, or at least 10 micromolar. In some embodiments a FLT3 inhibitor has substantially no activity against MET.

In some embodiments, KCC2 expression enhancing compounds are validated using another assay. In certain embodiments, the compound is validated by enzyme-linked immunosorbent assay, protein immunoprecipitation, immunoelectrophoresis, protein immunostaining, or Western blot experiments. In certain embodiments the compounds are validated by experiments that quantify the level of expression of KCC2 by utilizing antibodies that specifically bind to KCC2. For example, in certain embodiments, the compound is validated by Western blot experiments. These experiments can quantify the level of gene expression of KCC2 by utilizing antibodies that specifically target KCC2. The present disclosure describes Western blot experiments performed with WT and/or RTT cultured neurons, as well as brain tissue slices prepared from rodents. In certain embodiments the rodent is a mouse. In certain embodiment, the mouse is a neonatal mouse. In some embodiments, the KEECs validated by Western blot experiments include (E)-(4-(2-(1H-indazol-3-yl)vinyl)phenyl) (piperazin-1-yl)methanone (KW-2449), (2Z,3E)-6'-bromo-3-(hydroxyimino)-[2,3'-biindolinylidene]-2'-one (KIN 001-043), N-(2-diethylaminoethyl)-5-[(Z)-(5-fluoro-2-oxo-1H-indol-3-ylidene)methyl]-2,4-dimethyl-1H-pyrrole-3-carboxamide (Sunitinib), 1-(2-(5-(2-(3-methyloxetan-3-yl) ethyl)-1H-benzo[d]imidazol-1-yl)quinolin-8-yl)piperidin-4-amine (Crenolanib), N'-[4-[(6,7-dimethoxy-4-quinolinyl) oxy]phenyl]-N-(4-fluorophenyl)-1,1-cyclopropanedicarboxamide (XL-184), 3-((6-(3- aminophenyl)-7H-pyrrolo[2,3-d ]pyrimidin-4-yl)methyl) phenol (TWS-119), (2Z,3E)-3-(hydroxyimino)-[2,3'-biindolinylidene]-2'-one (Indirubin-monoxime), resveratrol, and piperine.

In some embodiments, the Feline McDonough sarcoma-like tyrosine kinase 3 (FLT3) inhibitors that can be used in the present invention are described in (U.S. patent application Ser. No. 11/550,077, filed Oct. 17, 2006, and issued on Sep. 14, 2010 as U.S. Pat. No.7,795,279; International Patent Application No. PCT/JP2013/070436, filed on Jul. 29, 2013, published as WO/2014/017659 on Jan. 30, 2014; U.S. patent application Ser. No. 11/422,413, filed Jun. 6, 2006, published as US 2006/0281788 on Dec. 14, 2006; U.S. patent application Ser. No. 11/422,379, filed Jun. 6, 2006, published as US 2006/0281771 on Dec. 14, 2006; U.S. patent application Ser. No. 10/989,766, filed Nov. 15, 2004, published as US 2005/0171171 on Aug. 4, 2005; U.S. patent application Ser. No. 10/917,578, filed Aug. 13, 2004, published as US 2005/0124637 on Jun. 9, 2005; International Patent Application No. PCT/EP2002/012076, filed on Oct. 29, 2002, published as WO/2003/037347 on May 8, 2003; U.S. patent application Ser. No. 11/192,318, filed Jul. 27, 2005, and issued on Nov. 18, 2008 as U.S. Pat. No. 7,452,993; U.S. patent application Ser. No. 11/192,341, filed Jul. 27, 2005, and issued on Apr. 22, 2008, as U.S. Pat. No. 7,361,763; International Patent Application No. PCT/GB2008/001612, filed May 9, 2008, published as WO/2008/139161 on Nov. 20, 2008).

In certain embodiments, the Feline McDonough sarcoma-like tyrosine kinase 3 (FLT3) inhibitors are classified into one or more of the following classes of compounds: ureas, carboxamides, alkaloids, and benzamidazoles.

In certain embodiments, the FLT3 inhibitors are compounds of the following formula:

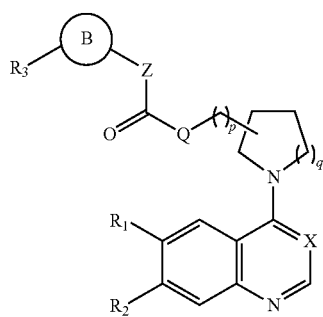

and pharmaceutically acceptable salts, and stereochemical isomers thereof, wherein: q is 0, 1 or 2; p is 0 or 1; Q is NH, N(alkyl), O, or a direct bond; X is N, or C—CN, or CH provided that $R_{bb}$ is not heteroaryl or halogen; Z is NH, N(alkyl), or CH$_2$; B is selected from: cycloalkyl, a nine to ten membered benzo-fused heteroaryl, or a nine to ten membered benzo-fused heterocyclyl, or, if $R_3$ is present, phenyl or heteroaryl, provided that B is not thiadiazinyl; $R_1$ and $R_2$ are independently selected from the following:

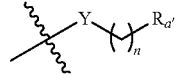 (a-1)

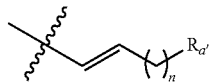 (a-2)

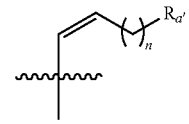 (a-3)

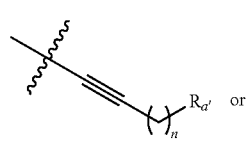 (a-4)

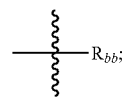 (a-5)

wherein n is 1, 2, 3 or 4; Y is a direct bond, O, S, NH, or N(alkyl); $R_a$ is alkoxy, phenoxy, heteroaryl optionally substituted with $R_5$, hydroxyl, alkylamino, dialkylamino, oxazolidinonyl optionally substituted with $R_5$, pyrrolidinonyl optionally substituted with $R_5$, piperidinonyl optionally substituted with $R_5$, cyclic heterodionyl optionally substituted with $R_5$, heterocyclyl optionally substituted with $R_5$, squaryl, —COOR$_y$, —CONR$_w$R$_x$, —N(R$_w$)CON(R$_y$)(R$_x$), —N(R$_y$)CON(R$_w$)(R$_x$), —N(R$_x$)C(O)OR$_x$, —N(R$_w$)COR$_y$, —SR$_y$, —SOR$_y$, —SO$_2$R$_y$, —NR$_w$SO$_2$R$_y$, —NR$_w$SO$_2$R$_x$, —SO$_3$R$_y$, —OSO$_2$NR$_w$R$_x$, or —SO$_2$NR$_w$R$_x$; $R_{bb}$ is hydrogen, halogen, alkoxy, phenyl, heteroaryl, or heterocyclyl; $R_5$ is one, two, or three substituents independently selected from: halogen, cyano, trifluoromethyl, amino, hydroxyl, alkoxy, —C(O)alkyl, —SO$_2$alkyl, —C(O)N(alkyl):, alkyl, —C$_{(1-4)}$alkyl-OH, or alkylamino; $R_w$ and $R_x$ are independently selected from: hydrogen, alkyl, alkenyl, aralkyl, or heteroaralkyl, or $R_w$ and $R_x$ may optionally be taken together to form a 5 to 7 membered ring, optionally containing a heteromoiety selected from O, NH, N(alkyl), SO, SO$_2$, or S; $R_y$ is selected from: hydrogen, alkyl, alkenyl, cycloalkyl, phenyl, aralkyl, heteroaralkyl, or heteroaryl; and $R_3$ is one or more substituents, optionally present, and independently selected from: alkyl, alkoxy, halogen, nitro, cycloalkyl optionally substituted with $R_4$, heteroaryl optionally substituted with $R_4$, alkylamino, heterocyclyl optionally substituted with $R_4$, alkoxyether, —O(cycloalkyl), pyrrolidinonyl optionally substituted with $R_4$, phenoxy optionally substituted with $R_4$, —CN, —OCHF$_2$, —OCF$_3$, —CF$_3$, halogenated alkyl, heteroaryloxy optionally substituted with $R_4$, dialkylamino, —NHSO$_2$alkyl, or —SO$_2$alkyl; wherein $R_4$ is independently selected from: halogen, cyano, trifluoromethyl, amino, hydroxyl, alkoxy, —C(O)alkyl, —CO$_2$alkyl, —SO$_2$alkyl, —C(O)N(alkyl)$_2$, alkyl, or alkylamino (see U.S. patent application Ser. No. 11/422,379, filed Jun. 6, 2006, published as US 2006/0281771 on Dec. 14, 2006).

In certain embodiments, the FLT3 inhibitors are compounds of the following formula:

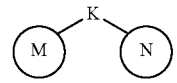

wherein: M is substituted or unsubstituted heteroaryl, or substituted or unsubstituted aryl; N is a substituted or unsubstituted aryl, or substituted or unsubstituted heteroaryl; and K is

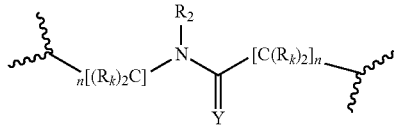

where Y is O or S; each $R_k$ is independently H, halogen, substituted or unsubstituted alkyl, —OH, substituted or unsubstituted alkoxy, —OC(O)$R_2$, —NO$_2$, —N($R_2$)$_2$, —SR$_2$, —C(O)R$_2$, —C(O)$_2$R$_2$, —C(O)N(R$_2$)$_2$, or —N(R$_2$)C(O)R$_2$, each $R_2$ is independently H, substituted or unsubstituted alkyl, substituted or unsubstituted cycloalkyl, substituted or unsubstituted heterocyclyl, substituted or unsubstituted aryl, or substituted or unsubstituted heteroaryl; or wherein two $R_2$ groups are linked together by an optionally substituted alkylene; and each n is independently 0, 1, 2, 3 or 4; or an active metabolite, or a pharmaceutically acceptable prodrug, isomer, pharmaceutically acceptable salt or solvate thereof (see U.S. patent application Ser. No. 10/989,766, filed Nov. 15, 2004, published as US 2005/0171171 on Aug. 4, 2005).

In certain embodiments, M is a unsubstituted aryl and N is an unsubstituted heteroaryl. In certain embodiments, M is a substituted aryl and N is an unsubstituted heteroaryl. In certain embodiments, M is an unsubstituted aryl and N is a substituted heteroaryl. In certain embodiments, M is a substituted aryl and N is a substituted heteroaryl. In certain embodiments, M or N is a unsubstituted phenyl. In certain embodiments, M or N is a substituted phenyl. In certain embodiments, M or N is selected from: pyrrolyl, furanyl, thiophenyl, imidazolyl, pyrazolyl, oxazolyl, isoxazolyl, thiazolyl, isothiazolyl triazolyl, oxadiazolyl, thiadiazolyl, tetrazolyl, pyridinyl, pyridazinyl, pyrimidinyl, pyrazinyl, triazinyl, tetrazinyl, azepinyl, oxepinyl, thiepinyl, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, purinyl, naphthyridinyl, pteridinyl, quinolinyl, isoquinolinyl, cinnolinyl, quinoxalinyl, phthalazinyl, quinazolinyl, phenanthridinyl, dibenzofuranyl, carbazolyl, acridinyl, phenothiazinyl, phenoxazinyl and phenazinyl. In certain embodiments, M or N is a substituted thiophenyl. In certain embodiments, the FLT3 inhibitor is OSI-930:

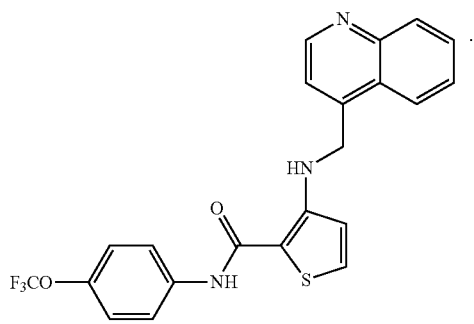 [SMILES: O=C(Nc1ccc(OC(F)(F)F)cc1)c1sccc1NCc1ccnc2ccccc12]

In certain embodiments, the FLT3 inhibitor is FLT inhibitor-1 (Calbiochem 343020):

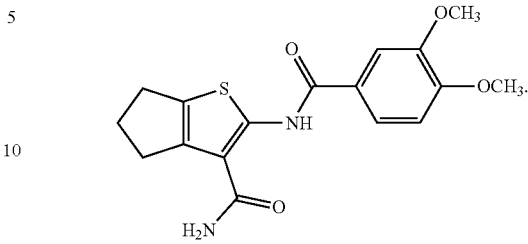

In certain embodiments, the FLT3 inhibitors are compounds of the following formula:

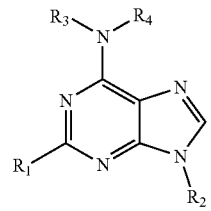

in which: $R_1$ is selected from hydrogen, halo, $C_{1-6}$alkyl, halo-substituted-$C_{1-6}$alkyl, $C_{1-6}$alkoxy, halo-substituted-$C_{1-6}$alkoxy, —OXOR$^5$, —OXR$^6$, —OXNR$_5$R$_6$, —OXONR$_5$R$_6$, —XR$_6$, —XNR$_5$R$_6$ and —XNR$_7$XNR$_7$R$_7$; wherein X is selected from a bond, $C_{1-6}$alkylene, $C_{2-6}$alkenylene and $C_{2-6}$alkynylene; wherein $R_7$ is independently selected from hydrogen or $C_{1-6}$alkyl; $R_5$ is selected from hydrogen, $C_{1-6}$alkyl and —XOR$_7$; wherein X is selected from a bond, $C_{1-6}$alkylene, $C_{2-6}$alkenylene and $C_{2-6}$alkynylene; and $R_7$ is independently selected from hydrogen or $C_{1-6}$alkyl; $R_6$ is selected from hydrogen, $C_{1-6}$alkyl, $C_{3-12}$cycloalkyl$C_{0-4}$alkyl, $C_{3-8}$heterocycloalkyl$C_{0-4}$alkyl, $C_{6-10}$aryl$C_{0-4}$alkyl and $C_{5-10}$heteroaryl$C_{0-4}$alkyl; or $R_5$ and $R_6$ together with the nitrogen atom to which both $R_5$ and $R_6$ are attached form $C_{3-8}$heterocycloalkyl or $C_{5-8}$heteroaryl; wherein a methylene of any heterocycloalkyl formed by $R_5$ and $R_6$ can be optionally replaced by —C(O)— or —S(O)$_2$—; wherein any aryl, heteroaryl, cycloalkyl or heterocycloalkyl of $R_6$ or the combination of $R_5$ and $R_6$ can be optionally substituted by 1 to 3 radicals independently selected from —XNR$_7$R$_7$, —XOR$_7$, —XNR$_7$R$_7$, —XC(O)NR$_7$R$_7$, —XNR$_7$C(O)R$_7$, —XOR$_7$, —XC(O)OR$_7$, —XC(O)R$_7$, $C_{1-6}$alkyl, $C_{3-8}$heterocycloalkyl, $C_{5-10}$heteroaryl, $C_{3-12}$cycloalkyl and $C_{6-10}$aryl$C_{0-4}$alkyl; wherein any alkyl or alkylene of $R_1$ can optionally have a methylene replaced by a divalent radical selected from —NR$_7$C(O)—, —C(O)NR$_7$—, —NR—$_7$, —C(O)—, —O—, —S—, —S(O)— and —S(O)$_2$—; and wherein any alkyl or alkylene of $R_6$ can be optionally substituted by 1 to 3 radicals independently selected from $C_{5-8}$heteroaryl, —NR$_7$R$_7$, —C(O)NR$_7$R$_7$, —NR$_7$C(O)R$_7$, halo and hydroxy; wherein $R_7$ is independently selected from hydrogen or $C_{1-6}$alkyl; $R_2$ is selected from hydrogen, $C_{6-10}$aryl and $C_{5-10}$heteroaryl; wherein any aryl or heteroaryl of $R_2$ is optionally substituted with 1 to 3 radicals independently selected from —XNR$_7$R$_7$, —XOR$_7$, —XOR$_8$, —XC(O)OR$_7$, —XC(O)R$_7$, $C_{1-6}$alkyl, $C_{1-6}$alkoxy, nitro, cyano, hydroxy, halo and halo-substituted-$C_{1-6}$alkyl; wherein X and $R_7$ are as described above; and $R_8$ is $C_{6-10}$aryl$C_{0-4}$alkyl; $R_3$ is selected from hydrogen and $C_{1-6}$alkyl; $R_4$ is selected from $C_{3-12}$cycloalkyl$C_{0-4}$alkyl, $C_{3-8}$heterocycloalkyl$C_{0-4}$alkyl, $C_{6-10}$aryl$C_{0-4}$alkyl and $C_{5-10}$heteroaryl$C_{0-4}$alkyl; wherein any alkylene of $R_4$ can optionally have a methylene replaced by a divalent radical selected from —C(O)—, —S—, —S(O)— and —S(O)$_2$—; wherein said aryl, heteroaryl, cycloalkyl or heterocycloalkyl of $R_4$ is optionally substituted by 1 to 3 radicals selected from halo, $C_{1-6}$alkyl, $C_{1-6}$alkoxy, halo-substituted-$C_{1-6}$alkyl, halo-substituted-$C_{1-6}$alkoxy, —XR$_9$, —XOR$_9$, —XS(O)$_{0-2}$R$_7$, —XS(O)$_{0-2}$R$_9$, —XC(O)R$_7$, —XC(O)OR$_7$, —XP(O)R$_7$R$_7$, —XC(O)R$_9$, —XC(O)NR$_7$XNR$_7$R$_7$, —XC(O)NR$_7$R$_7$, —XC(O)NR$_7$R$_9$ and —XC(O)NR$_7$XOR$_7$; wherein X and R$_7$ are as described above; $R_9$ is selected from $C_{3-12}$cycloalkyl $C_{0-4}$alkyl, $C_{3-8}$heterocycloalkyl$C_{0-4}$alkyl, $C_{6-10}$aryl and $C_{5-10}$heteroaryl; wherein any aryl, heteroaryl, cycloalkyl or heterocycloalkyl of $R_9$ is optionally substituted by 1 to 3 radicals selected from $C_{1-6}$alkyl, —XC(O)R$_7$ and —XC(O)NR$_7$R$_7$; wherein X and R$_7$ are as described above; and the pharmaceutically acceptable salts, hydrates, solvates, isomers and prodrugs thereof (see U.S. patent application Ser. No. 10/917,578, filed Aug. 13, 2004, published as US 2005/0124637 on Jun. 9, 2005).

In certain embodiments, the FLT3 inhibitors are compounds of the following formula:

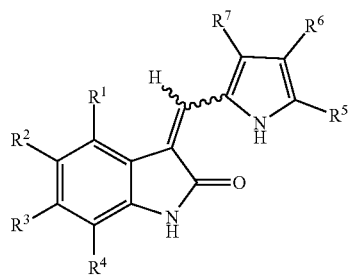

wherein: $R_1$ is hydrogen; $R_2$ is selected from the group consisting of hydrogen, halo, and —S(O)$_2$NR$_{13}$R$_{14}$; $R_3$ is hydrogen; $R_4$ is hydrogen; $R_5$ is alkyl; $R_6$ is selected from the group consisting of hydrogen and —C(O)R$_{10}$, or $R_5$ and $R_6$ combine to form an alkyl group consisting of —(CH$_2$)$_4$—; $R_7$ is alkyl; $R_{10}$ is selected from the group consisting of —N(R$_{11}$)(CH$_2$)$_n$R$_{12}$ and —NR$_{13}$R$_{14}$; $R_{11}$ is H; n is independently 1, 2, 3 or 4; $R_{12}$ is —NR$_{13}$R$_{14}$; and $R_{13}$ and $R_{14}$ are independently alkyl or aryl, or $R_{13}$ and $R_{14}$ may combine to form a heterocyclo group; or a pharmaceutically acceptable salt thereof (see U.S. patent application Ser. No. 13/058,171, filed on Aug. 8, 2009, published as U.S. Pat. No. 8,993,615 on Mar. 31, 2015).

In certain embodiments, the FLT3 inhibitors are compounds of the following formula:

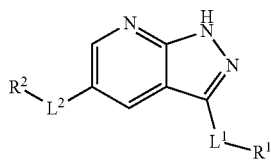

wherein $L^1$ and $L^2$ are independently a bond, —S(O)$_n$—, —O—, —NH—, unsubstituted $C_1$-$C_5$alkylene, or unsubstituted 2 to 5 membered heteroalkylene, wherein n is an integer from 0 to 2, and $R^1$ and $R^2$ are independently substituted or unsubstituted cycloalkyl, substituted or unsubstituted heterocycloalkyl, substituted or unsubstituted heteroaryl, or substituted or unsubstituted aryl, with the proviso that $R^1$ is not substituted or unsubstituted pyrrolyl, and that $L^1$ is not unsubstituted 2 to 5 membered heteroalkylene when $R^1$ and $R^2$ are both unsubstituted phenyl, and that $L^1$ is not —S(O)$_2$— when $R^2$ is unsubstituted piperazinyl, and that $R^1$ is not substituted or unsubstituted isoxazolyl when $R^2$ is unsubstituted pyridinyl (see U.S. patent application Ser. No. 11/192,318, filed Jul. 27, 2005, and issued on Nov. 18, 2008 as U.S. Pat. No. 7,452,993).

In certain embodiments, the FLT3 inhibitors are compounds of the following formula:

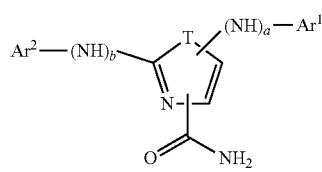

or a salt, solvate, N-oxide or tautomer thereof; wherein: a is 0 or 1; bis 0 or 1: provided that the sum of a and b is 0 or 1; T is O or NH; Ar$^1$ is a monocyclic or bicyclic 5- to 10-membered aryl or heteroaryl group containing up to 4 heteroatoms selected from O, N and S$_1$ and being optionally substituted by one or more substituents $R^1$; Ar$^2$ is a monocyclic or bicyclic 5- to 10-membered aryl or heteroaryl group containing up to 4 heteroatoms selected from O$_1$ N and S and being optionally substituted by one or more substituents $R^2$; $R^1$ is halogen; cyano; nitro; a group $R^a$-$R^b$; or a 3 to 8-membered carbocyclic or heterocyclic ring containing up to 4 heteroatoms selected from O, N and S and being optionally substituted by one or more substituents $R^3$; $R^a$ is a bond, O, CO$_1$ X$^1$C(X$^2$), C(X$^2$)X$^1$, X$^1$C(X$^2$)X$^1$, S, SO, SO$_2$, NR$^C$, SO$_2$NR$^0$ or NR$^0$SO$_2$; $R^b$ is: hydrogen; or a 3 to 8-membered carbocyclic or heterocyclic ring containing up to 4 heteroatoms selected from O, N and S and being optionally substituted by one or more substituents $R^3$; or a $C_{1-12}$ acyclic hydrocarbon group optionally substituted by one or more substituents selected from hydroxy; oxo; halogen; cyano; nitro; carboxy; amino; N(R$^C$)$_2$; and 3 to 8-membered carbocyclic or heterocyclic rings containing up to 4 heteroatoms selected from O, N and S and being optionally substituted by one or more substituents $R^3$; wherein one to three but not all of the carbon atoms of the $C_{1-12}$ acyclic hydrocarbon group may optionally be replaced by O, CO, X$^1$C(X$^2$), C(X$^2$)X$^1$, X$^1$C(X$^2$)X$^1$, S, SO, SO$_2$, NR$^0$, SO$_2$NR$^C$ or NR$^0$SO$_2$; $R^0$ is hydrogen or a $C_{1-4}$ hydrocarbon group; X$^1$ is O, S or NR$^C$; X$^2$ is =O, =S or =NR$^C$; $R^2$ is halogen; cyano; nitro; or a group $R^a$-$R^d$; $R^d$ is hydrogen; a $C_{1-4}$ alkyl group optionally substituted by one or more fluorine atoms; or a benzyl group wherein the benzene ring of the benzyl group is optionally substituted with one to three substituents selected from halogen, cyano, $C_{1-4}$ alkyl and $C_{1-4}$ alkoxy, and wherein the $C_{1-4}$ alkyl and $C_{1-4}$ alkoxy substituents on the benzene ring are each optionally substituted with one or more fluorine atoms; $R^3$ is X$^2$; halogen; cyano; nitro; a group $R^a$-$R^e$; or a 3 to 7-membered carbocyclic or heterocyclic ring containing up to 4 heteroatoms selected from O, N and S and being optionally substituted by a group $R^4$; $R^e$ is: hydrogen; or a $C_{1-6}$acyclic hydrocarbon group optionally substituted by one or more substituents selected from hydroxy; oxo; halogen; cyano; nitro; carboxy; amino; and N(R$^C$)$_2$; wherein one to three but not all of the carbon atoms of the $C_{1-6}$ acyclic hydrocarbon group may optionally be replaced by O, S, SO, SO$_2$, NR$^C$, X$^1$C(X$^2$), C(X$^2$)X$^1$ or X$^1$C(X$^2$)X$^1$; or a benzyl group wherein the benzene ring of the benzyl group is optionally substituted with one to three substituents selected from halogen, cyano, C$_{1-4}$ alkyl and C$_{1-4}$ alkoxy, and wherein the C$_{1-4}$ alkyl and C$_{1-4}$ alkoxy groups are each optionally substituted with one or more fluorine atoms; and R$^4$ is selected from halogen, cyano, nitro and a group R$^a$-R$^d$; provided that when a is O, Ar$^1$ is other than a 2-aminopyridin-4-yl or 2-amino-pyrimidin-4-yl group wherein the 2-amino moiety is optionally substituted; and that neither Ar$^2$—(NH)$_b$— nor Ar$^1$—(NH)$_a$— form an optionally substituted quinoxalin-4-ylamino group; and that when a is 1 and b is O, then Ar$^2$ is other than a bicyclic group containing a pyrrole or pyrazole ring fused to a non-aromatic six-membered carbocyclic ring wherein the point of attachment of Ar$^2$ is a nitrogen atom of the pyrrole or pyrazole ring; but excluding the compounds: 2,5-diphenyl-1H-imidazole-4-carboxylic acid amide and tautomers thereof; 2-(4-fluorophenyl)-5-(4-methoxyphenyl)-1H-imidazole-4-carboxylic acid amide and tautomers thereof; 2-phenyl-5-thiophen-2-yl-1H-imidazole-4-carboxylic acid amide and tautomers thereof; 2-phenyl-5-(3,4,5-trimethoxy-phenyl)-oxazole-4-carboxylic acid amide; 2,5-diphenyl-oxazole-4-carboxylic acid amide; and 2-(4-methylphenyl)-5-phenyl-oxazole-4-carboxylic acid amide (see International Patent Application No. PCT/GB2008/001612, filed May 9, 2008, published as WO/2008/139161 on Nov. 20, 2008).

In certain embodiments, the Feline McDonough sarcoma-like tyrosine kinase 3 (FLT3) inhibitors are selected from a group consisting of Pacritinib, TG101209, Crenolanib, Lestautirinib, PKC412, Tandutinib, Sunitinib, a Sorafenib, Linifanib, Dovitinib (TKI-258), KW-2449, Quizartinib (AC220), Dovitinib Dilactic acid, Tandutinib, Cabozanitib (XL-184), TG101209, Amuvatinib (MP-470), and ENMD-2076. In certain embodiments, the FLT3 inhibitors are selected from a group consisting of Pacritinib, TG101209, Crenolanib, Lestautirinib, PKC412, Tandutinib, Sunitinib, Sorafenib, Linifanib, Dovitinib (TKI-258), KW-2449, Quizartinib (AC220), Dovitinib Dilactic acid, Tandutinib, Cabozanitib (XL-184), TG101209, Amuvatinib (MP-470), Foretinib (GSK1363089; XL880; EXEL-2880), OSI-930, and ENMD-2076. In certain embodiments the FLT3 inhibitor is Gilteritinib, MRX-2843, G-749, AZD2932, or JNJ-47117096.

In some embodiments a target of interest herein (e.g., a kinase, e.g., FLT3 or GSK3) is targeted for degradation based upon the proteolysis targeting chimera (PROTAC) concept (see, e.g., Carmony, K C and Kim, K, PROTAC-Induced Proteolytic Targeting, Methods Mol Biol. 2012; 832: Ch. 44). In this approach, a heterobifunctional agent is designed to contain a first domain (e.g., a small molecule) that binds to a protein of interest (e.g., FLT3), a second domain that binds to an E3 ubiquitin ligase complex (e.g., a compound that binds to cereblon (CRBN) or VHL ubiquitin ligases), and, typically, a linker to tether these domains together In some embodiments a FLT3 inhibitor is TL12-186, TL13-117, or TL13-149, the structures of which are presented below (see Huang, H T, et al., Cell Chem Biol. 2018 Jan. 18;25(1):88-99).

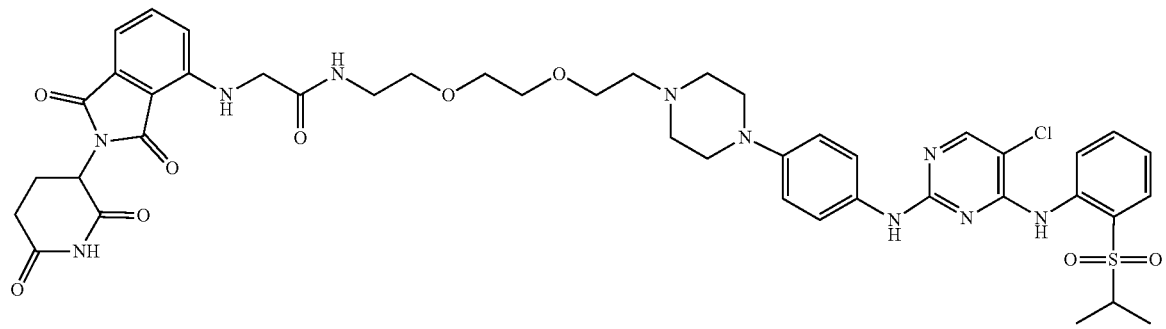

TL12-186

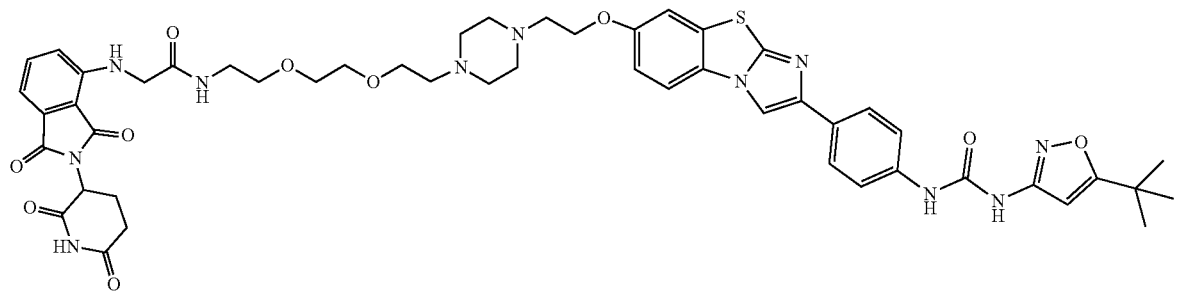

TL13-117

TL13-149

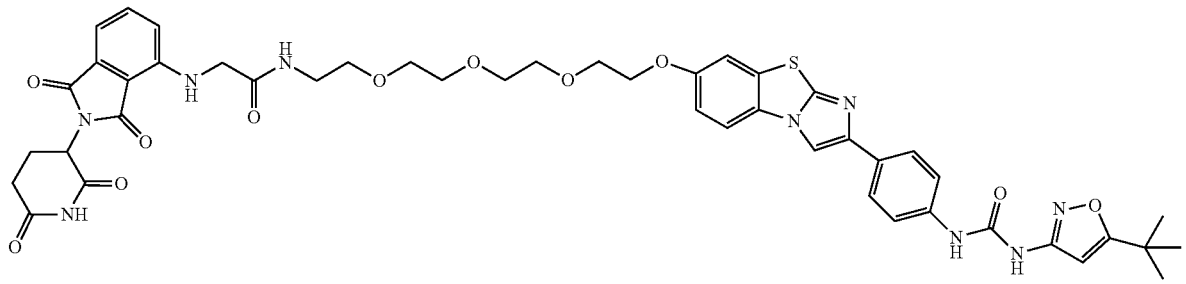

In some embodiments, the glycogen synthase kinase 3 (GSK3) inhibitors that can be used in the present invention are described in (U.S. patent application Ser. No. 10/360,535, filed on Feb. 6, 2003, published as US 2004/0034037 on Feb. 19, 2004; U.S. patent application Ser. No. 09/267,971, filed Mar. 12, 1999, and issued on May 2, 2000 as U.S. Pat. No. 6,057,117; U.S. patent application Ser. No. 09/336,038, filed Jun. 18, 1999, and issued on Jul. 9, 2002 as U.S. Pat. No. 6,417,185; U.S. patent application Ser. No. 09/949,035, filed on Sep. 6, 2001, published as US 2002/0156087 on May 16, 2006, and issued on May 16, 2006 as U.S. Pat. No. 7,045,519; U.S. patent application Ser. No. 10/936,470, filed on Sep. 7, 2004, published as US 2005/0137201 on Jun. 23, 2005, and issued on Nov. 4, 2008 as U.S. Pat. No. 7,446,199; U.S. patent application Ser. No. 08/948,887, filed on Oct. 10, 1997, and issued on Nov. 28, 2000, as U.S. Pat. No. 6,153,618; U.S. patent application Ser. No. 10/917,707, filed Aug. 13, 2004, and published as US 2005/0054663 on Mar. 10, 2005; U.S. patent application Ser. No. 09/738,040, filed Dec. 14, 2000, published as US 2001/0034051 on Oct. 25, 2001, and issued on Aug. 19, 2003 as U.S. Pat. No. 6,608,063; U.S. patent application Ser. No. 10/109,070, filed Mar. 28, 2002, published as US 2003/0087922 on May 8, 2003, and issued on Sep. 27, 2005 as U.S. Pat. No. 6,949,544; U.S. patent application Ser. No. 10/639,784, filed on Aug. 12, 2003, published as US 2004/0106615 on Jun. 3, 2004, and issued on Dec. 4, 2007 as U.S. Pat. No. 7,304,071; U.S. patent application Ser. No. 11/913,612, filed Nov. 5, 2007, and published as US 2008/0207594 on Aug. 28, 2008; U.S. patent application Ser. No. 10/228,621, filed Aug. 26, 2002, and published as US 2003/0008866 on Jan. 9, 2003; U.S. patent application Ser. No. 12/338,129, filed Dec. 18, 2008, published as US 2009/0118278 on May 7, 2009, and issued on Jan. 18, 2011 as U.S. Pat. No. 7,872,129; U.S. patent application Ser. No. 10/891,912, filed Jul. 13, 2004, published as US 2005/0004152 on Jan. 6, 2005, and issued on Aug. 14, 2007 as U.S. Pat. No. 7,256,190; U.S. patent application Ser. No. 12/300,056, filed Jan. 12, 2009, and published as US 2009/0142337 on Jun. 4, 2009; U.S. patent application Ser. No. 09/951,902, filed Sep. 14, 2001, published as US 2002/0147146 on Oct. 10, 2002, and issued on Aug. 24, 2004 as U.S. Pat. No. 6,780,625; U.S. patent application Ser. No. 10/493,452, filed Apr. 23, 2004, published as US 2005/0004125 on Jan. 6, 2005, and issued on Apr. 7, 2009 as U.S. Pat. No. 7,514,445; International Patent Application No. PCT/EP2011/061198, filed on Jul. 4, 2011, published as WO/2012/004217 on Jan. 12, 2012; International Patent Application No. PCT/US2003/026625, filed on Aug. 21, 2003, published as WO/2004/018455 on Mar. 4, 2004; International Patent Application No. PCT/US2001/042081, filed on Sep. 6, 2001, published as WO/2002/020495 on Mar. 14, 2002; International Patent Application No. PCT/EP2001/003640, filed on Mar. 22, 2001, published as WO/2001/070729 on Sep. 27, 2001).

In certain embodiments, the GSK3 inhibitors are classified into one or more of the following classes of compounds: metal cations, marine organism derived compounds, ureas, aminopyrimidines, arylindolemaleimides, thiazoles, thiadiazolidindiones, halomethylketones, and peptides.

In certain embodiments, the GSK3 inhibitors are compounds of the following formula:

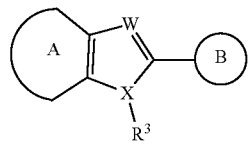

or a pharmaceutically acceptable salt thereof, wherein: Ring A is an optionally substituted 5-7 membered, partially unsaturated or fully unsaturated ring having 0-3 heteroatoms independently selected from nitrogen, oxygen or sulfur, and wherein Ring A is optionally fused to an optionally substituted saturated, partially unsaturated or fully unsaturated 5-8 member ring having 0-3 heteroatoms independently selected from nitrogen, oxygen or sulfur; Ring B is an optionally substituted 5-6 membered ring having 0 to 4 heteroatoms, independently selected from nitrogen, oxygen, or sulfur, wherein said ring has a first substituent, —N(R$^1$)$_2$, in the position adjacent to the point of attachment, and is optionally substituted by up to two additional substituents; W is selected from nitrogen or CR$^4$ and X is selected from nitrogen or CH, wherein at least one of W and X is nitrogen; R$^1$ is selected from R or R$^2$; R$^2$ is selected from —SO$_2$R, —SO$_2$N(R)$_2$, —CN, —C(O)R, —CO$_2$R, or —CON(R)$_2$; R is independently selected from hydrogen or an optionally substituted group selected from C$_{1-6}$ aliphatic, a 3-6 membered saturated, partially unsaturated, or aryl ring having 0-4 heteroatoms independently selected from nitrogen, oxygen, or sulfur, or: two R groups on the same nitrogen are taken together with the nitrogen bound thereto to form a 3-7 membered heterocyclic or heteroaryl ring having 1-4 heteroatoms independently selected from nitrogen, oxygen, or sulfur; R$^3$ is selected from T-CN or L-R; T is a valence bond or an optionally substituted C$_{1-6}$ alkylidene chain; L is a valence bond or a C$_{1-4}$ alkylidene chain, wherein up to two methylene units of L are optionally, and independently, replaced by —O—, —S—, —NR—, —NRC(O)—, —NRC(O)NR—, —OC(O)NR—, —C(O)—, —CO$_2$—, —NRCO$_2$—, —C(O)NR—, —SO$_2$NR—, —NRSO$_2$—, or —NRSO$_2$NR—; and R$^4$ is selected from L-R, -halo, T-NO$_2$, T-CN (see U.S. patent application Ser. No. 10/360,535, filed on Feb. 6, 2003, published as US 2004/0034037 on Feb. 19, 2004; U.S. patent application Ser. No. 09/267,971, filed Mar. 12, 1999, and issued on May 2, 2000 as U.S. Pat. No. 6,057,117).

In certain embodiments, the GSK3 inhibitors are compounds of the following formula:

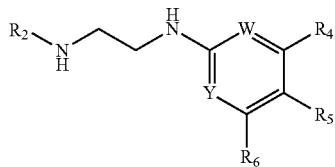

wherein: W and Y are each nitrogen; R$_2$ is an optionally substituted aryl; R$_4$ and R$_6$ are each independently selected from the group consisting of hydrogen, a halo, and R$_7$, wherein R$_7$ is a monovalent radical selected from the group consisting of a lower alkyl, a cycloalkyl, an aryl, an aminoalkyl, an aminoaralkyl, an aminocycloalkylaryl, an arylcarboxamidocycloalkylaralkyl, an arylcarboxamidocycloalkylaryl, an arylcarboxamidoalkylcycloalkyl, an arylcarboxamidoaryl, an arylcarboxamidoalkyl, an arylcarboxamidoaralkyl, an arylcarboxamidoalkoxyalkyl, an aminoalkoxyalkyl, and an arylsulfonamidoaralkyl, and wherein R$_7$ is optionally substituted; R$_5$ is selected from the group consisting of hydrogen, carboxyl, nitro, amino, cyano, an optionally substituted lower alkyl, an optionally substituted aryl, an optionally substituted aralkyl, an optionally substituted aminoalkyl, an optionally substituted aminoaryl, an optionally substituted aminoaralkyl, an optionally substituted aminoalkoxyalkyl, an optionally substituted arylaminoalkyl, an optionally substituted arylaminoaryl, an optionally substituted arylaminoaralkyl, an optionally substituted arylalkylamino, all optionally substituted arylalkylaminoalkyl, an optionally substituted arylalkylaminoaralkyl, an optionally substituted carboxcycloamido, an optionally substituted acyloxyalkyl, an optionally substituted acyloxyaryl, an optionally substituted acyloxyaralkyl, an optionally substituted acyloxyalkylcycloalkyl, an optionally substituted acyloxyalkylaminoalkyl, and an optionally substituted sulfonylalkyl, an optionally substituted carbamylalkyl, an optionally substituted carbamylaryl, an optionally substituted carbamylaralkyl, an optionally substituted carbamylalkylamino, an optionally substituted carbamylalkylaminoalkyl, an optionally substituted carbamylalkylaminoaryl, and an optionally substituted carbamylalkylaminoaralkyl; wherein, no more than two of R$_4$, R$_5$, and R$_6$ are hydrogen; and salts thereof (see U.S. patent application Ser. No. 09/336,038, filed Jun. 18, 1999, and issued on Jul. 9, 2002 as U.S. Pat. No. 6,417,185).

In certain embodiments, the GSK3 inhibitors are compounds of the following formula:

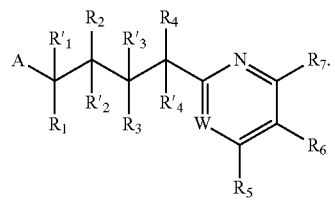

wherein: W is optionally substituted carbon or nitrogen; X and Y are independently selected from the group consisting of nitrogen, oxygen, and optionally substituted carbon; A is optionally substituted aryl or heteroaryl; R$_1$, R'$_1$, R$_2$, R'$_2$, R$_3$, R'$_3$, R$_4$ and R'$_4$ are independently selected from the group consisting of hydrogen, hydroxyl, and optionally substituted loweralkyl, cycloloweralkyl, cyclicaminoalkyl, alkylaminoalkyl, loweralkoxy, amino, alkylamino, alkylcarbonyl, arylcarbonyl, aralkylcarbonyl, heteroarylcarbonyl, heteroaralkylcarbonyl, aryl and heteroaryl, and R'$_1$, R'$_2$, R'$_3$ and R'$_4$ are independently selected from the group consisting of hydrogen, and optionally substituted loweralkyl; R$_5$ and R$_7$ are independently selected from the group consisting of hydrogen, halo, and optionally substituted loweralkyl, cycloalkyl, alkoxy, amino, aminoalkoxy, alkylamino, aralkylamino, heteroaralkylamino, arylamino, heteroarylamino cycloimido, heterocycloimido, amidino, cycloamidino, heterocycloamidino, guanidinyl, aryl, biaryl, heteroaryl, heterobiaryl, heterocycloalkyl, and arylsulfonamido; R$_6$ is selected from the group consisting of hydrogen, hydroxy, halo, carboxyl, nitro, amino, amido, amidino, imido, cyano, and substituted or unsubstituted loweralkyl, loweralkoxy, alkylcarbonyl, arylcarbonyl, aralkylcarbonyl, heteroarylcarbonyl, heteraralkylcarbonyl, alkylcarbonyloxy, arylcarbonyloxy, aralkylcarbonyloxy, alkylaminocarbonyloxy, arylaminocarbonyloxy, formyl, loweralkylcarbonyl, loweralkoxycarbonyl, aminocarbonyl, aminoaryl, alkylsulfonyl, sulfonamido, amrinoalkoxy, alkylamino, heteroarylamino, alkylcarbonylamino, alkylaminocarbonylamino, arylaminocarbonylamino, aralkylcarbonylamino, heteroaralkylcarbonylamino, arylcarbonylamino, heteroarylcarbonylamino cycloamido, cyclothioamido, cycloamidino, heterocycloamidino, cycloimido, heterocycloimido, guanidinyl, aryl, heteroaryl, heterocyclo, heterocycloalkyl, arylsulfonyl and arylsulfonamido; and the pharmaceutically acceptable salts thereof (see U.S. patent application Ser. No. 09/949,035, filed on Sep. 6, 2001, published as US 2002/0156087 on May 16, 2006, and issued on May 16, 2006 as U.S. Pat. No. 7,045,519).

In certain embodiments, the GSK3 inhibitors are compounds of formula (A):

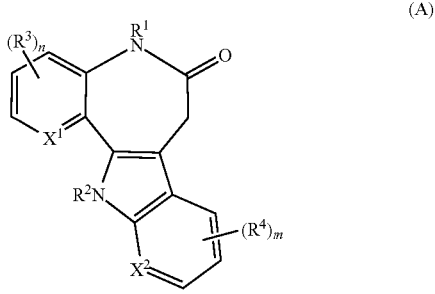

(A)

wherein X$^1$ and X$^2$ are independently N or CR$_3$ and preferably X$^1$ is N or CH and X$^2$ is CH; R$^1$ and R$^2$ are independently H, —C$_1$-C$_6$ alkyl, optionally substituted, or —CO—C$_1$-C$_6$ alkyl, optionally substituted, wherein the substituents are independently selected from one or more of halo, CN, OH, O—C$_1$-C$_6$alkyl; COOH, COO—C$_1$-C$_6$ alkyl, —CONH$_2$, —CONH(C$_1$-C$_6$)alkyl, —CON(C$_1$-C$_6$ alkyl)$_2$, aryl, heteroaryl or combinations thereof; each R$^3$ and R$^4$ is independently selected from C$_1$-C$_6$ alkyl, —C$_2$-C$_6$alkenyl; —C$_2$-C$_6$ alkynyl; —C$_3$-C$_{10}$ cycloalkyl, —C$_3$-C$_{10}$ heterocyclyl, aryl with 6 to 10 carbon atoms, heteroaryl with 5 to 10 ring atoms; each optionally substituted; halo, e.g. F, Cl, Br or I; —$NO_2$, —CN, —$OR^1$; —$COOR^1$ or —$NR^1R^2$; wherein $R^1$ and $R^2$ are as defined above; and wherein alkyl, alkenyl or alkynyl is optionally substituted with one or more of halo, —$NO_2$, —CN, —$OR^1$, $COOR^1$, —$OCOR^1$, —$NR^1R^2$, $NR^1COR^2$, —$NR^1OCOR^2$, —$NR^1CONR^1R^2$, —$SR^1$, $SOR^1$, —$SO_2R^1$, —$SONR^1R^2$, $SO_2NR^1R^2$ or —$NR^1SO_2NR^1NR^2$; or combinations thereof, wherein $R^1$ and $R^2$ are as defined above; wherein cycloalkyl, heterocyclyl, aryl or heteroaryl is optionally substituted with one or more of $C_1$-$C_6$ alkyl, halo, —$NO_2$, —CN, —$OR^1$, $COOR^1$, —$OCOR^1$, —$NR^1R^2$, $NR^1COR^2$, —$NR^1OCOR^2$, —$NR^1CONR^1R^2$, —$SR^1$, $SOR^1$, —$SO_2R^1$, —$SONR^1R^2$, $SO_2NR^1R^2$ or —$NR^1SO_2NR^1NR^2$; or combinations thereof, wherein $R^1$ and $R^2$ are as defined above; or wherein two $R^3$ or two $R^4$ may together form a ring; n=0-3, preferably 0-1 and more preferably 0; m=0-3, preferably 0, 1 or 2 and more preferably 1 or 2; or an optical isomer or a salt thereof (see U.S. patent application Ser. No. 11/913,612, filed Nov. 5, 2007, and published as US 2008/0207594 on Aug. 28, 2008).

In certain embodiments, the GSK3 inhibitors are compounds of the following formula:

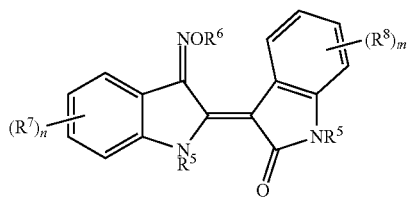

wherein $R^5$ and $R^6$ are independently H, —$C_1$-$C_6$ alkyl, optionally substituted, or —CO—$C_1$-$C_6$ alkyl, optionally substituted, wherein the substituents are independently selected from one or more of halo, CN, OH, O—$C_1$-$C_6$ alkyl; COOH, $COOC_1$-$C_6$ alkyl, —$CONH_2$, —$CONH(C_1$-$C_6$alkyl), —$CON(C_1$-$C_6$ alkyl)$_2$, aryl, heteroaryl or combinations thereof; each $R^7$ and $R^8$ is independently selected from $C_1$-$C_6$ alkyl, —$C_2$-$C_6$ alkenyl; $C_2$-$C_6$ alkynyl; $C_3$-$C_{10}$ cycloalkyl, —$C_3$-$C_{10}$ heterocyclyl, aryl with 6 to 10 carbon atoms, heteroaryl with 5 to 10 ring atoms, each optionally substituted; halo, e.g. F, Cl, Br or I; —$NO_2$, —CN, —$OR^1$; —$COOR^1$; or $NR^1R^2$, wherein $R^1$ and $R^2$ are as defined in formula (A), wherein alkyl, alkenyl or alkynyl is optionally substituted with one or more of oxo, halo, —$NO_2$, —CN, —$OR^1$, $COOR^1$, —$OCOR^1$, —$NR^1R^2$, $NR^1COR^2$, —$NR^1OCOR^2$, —$NR^1CONR^1R^2$, —$SR^1$, $SOR^1$, —$SO_2R^1$, —$SONR^1R^2$, $SO_2NR^1R^2$ or —$NR^1SO_2NR^1NR^2$ or combinations thereof, wherein $R^1$ and $R^2$ are as defined in formula (A); wherein cycloalkyl, heterocyclyl, aryl or heteroaryl is optionally substituted with one or more of $C_1$-$C_6$ alkyl, oxo, halo, —$NO_2$, —CN, —$OR^1$, $COOR^1$, —$OCOR^1$, —$NR^1R^2$, $NR^1COR^2$, —$NR^1OCOR^2$, —$NR^1CONR^1R^2$, —$SR^1$, $SOR^1$, —$SO_2R^1$, —$SONR^1R^2$, $SO_2NR^1R^2$ or —$NR^1SO_2NR^1NR^2$ or combinations thereof, wherein $R^1$ and $R^2$ are as defined in formula (A); or two $R^7$ or two $R^8$ may together form a ring; n=0-3, preferably 0-1 and more preferably 0; m=0-3, preferably 0-1 and more preferably 1, or an optical isomer or a salt thereof (see U.S. patent application Ser. No. 11/913,612, filed Nov. 5, 2007, and published as US 2008/0207594 on Aug. 28, 2008).

In certain embodiments, the GSK3 inhibitors are compounds of the following formula:

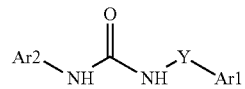

wherein Y is —[$C(R^9)_2$], each $R^9$ is independently H, F or $CH_3$, and r is 0-3, and Ar1 and Ar2 are aromatic or heteroaromatic rings optionally substituted with at least one $R^7$ wherein each $R^7$ is independently selected from $C_1$-$C_5$ alkyl, optionally halogenated; halo, e.g. F, Cl, Br or I; —$NO_2$, —CN, —$OR^5$; —$COOR^5$; —$OCOR^5$; —$NR^5R^6$ and —$NR^5COR^6$ and wherein $R^5$ and $R^6$ are independently H, $C_1$-$C_5$ alkyl, optionally halogenated, or —CO—$C_1$-$C_5$ alkyl (see U.S. patent application Ser. No. 11/913,612, filed Nov. 5, 2007, and published as US 2008/0207594 on Aug. 28, 2008).

In certain embodiments, the GSK3 inhibitors are compounds of the following formula:

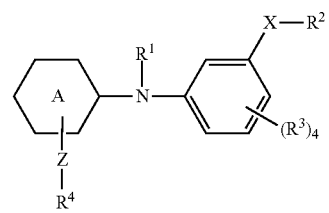

a pharmaceutically acceptable addition salt or a stereochemically isomeric form thereof, wherein the moiety

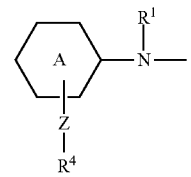

represents a radical of formula

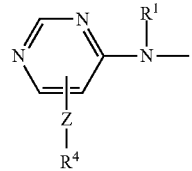

$R^1$ is hydrogen; aryl formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl, $C_{1-6}$alkylcarbonyloxy; $C_{1-6}$alkyloxy$C_{1-6}$alkylcarbonyl optionally substituted with $C_{1-6}$alkyloxycarbonyl; X is —$NR^1$—; —NH—NH—; —N—N—; —O—; —C(=O)—; —C(=S)—; —O—C(=O)—; —C(=O)—O—; —O—C(=O)—$C_{1-6}$alkyl; —C(=O)—O—$C_{1-6}$alkyl-; —O—$C_{1-6}$alkyl-C(=O)—; —C(=O)—$C_{1-6}$alkyl-O—; —O—C(=O)—$NR^1$—; —$NR^1$—C(=O)—O—; —O—C(=O)—C(=O)—; —C(=O)—$NR^1$—; —$NR^1$—C(=)—; —C(=S)—$NR^1$—, —$NR^1$—, —$NR^1$—C(=S)—; —$NR^1$—C(=O)—$NR^1$—; —$NR^1$—C(=)S—$NR^1$—; —$NR^1$—S(=O)—$NR^1$; $NR^1$—S(=O)$_2$—$NR^1$—;

—$C_{1-6}$alkyl-C(=O)—NR$^1$—; —O—$C_{1-6}$alkyl-C(=O)—NR$^1$—; —$C_{1-6}$alkyl-O—C(=O)—NR$^1$—; —$C_{1-6}$alkyl-; —O—$C_{1-6}$alkyl-; —$C_{1-6}$alkyl-O—; —NR$^1$—$C_{1-6}$alkyl-; —$C_{1-6}$alkyl-NR$^1$—; —NR$^1$—$C_{1-6}$alkyl-NR$^1$—; —NR$^1$—$C_{1-6}$alkyl-$C_{3-7}$cycloalkyl-; —$C_{2-6}$alkenyl-; —$C_{2-6}$alkynyl-; —O—$C_{2-6}$alkenyl-; —$C_{2-6}$alkenyl-O—; —NR$^1$—$C_{2-6}$alkenyl-; —$C_{2-6}$alkenyl-NR$^1$—; —NR$^1$—$C_{2-6}$alkenyl-NR$^1$—; —NR$^1$—$C_{2-6}$alkenyl-$C_{3-7}$cycloalkyl-; —O—$C_{2-6}$alkynyl-; —$C_{2-6}$alkynyl-O—; —NR$_1$—$C_{2-6}$alkynyl-; —$C_{2-6}$alkynyl-NR$^1$—; —NR$^1$—$C_{2-6}$alkynyl-NR$^1$—; —NR$^1$—$C_{2-6}$alkynyl-$C_{3-7}$cycloalkyl-; —O—$C_{1-6}$alkyl-O—; —O—$C_{2-6}$alkenyl-O—; —O—$C_{2-6}$alkynyl-O—; —CHOH—; —S—; —S(=O)—; —S(=O)$_2$—; —S(=O)—NR$^1$—; —S(=O)$_2$—NR$^1$—; —NR$^1$S(=O)—; —NR$^1$—(=O)$_2$—; —S—$C_{1-6}$alkyl-; —$C_{1-6}$alkyl-S—; —S—$S_{2-6}$alkenyl-; —$C_{2-6}$alkenyl-S—; —S—$C_{2-6}$alkynyl-; —$C_{2-6}$alkynyl-S—; —O—$C_{1-6}$alkyl-S(=O)$_2$— or a direct bond; Z is a direct bond, 'O—; —S—; —C(=O)—; —C(=O)—O—; —O—C(=O)—; —C(=S)—; —S(=O)—; —S(=O)$_2$—; —NR$^1$—; —NR$^1$—C(=O)—; —O—C(=O)—NR$^1$—; —NR$^1$C(=O)—O—; —NR$^1$—C(=S)—; —S(=O)—NR$^1$; —S(=O)$_2$—NR$^1$—; —NR$^1$—S(=O)—; —NR$^1$—S(=O)$_2$—; —NR$^1$—(C=O)—NR$^1$—; —NR$^1$—C(=S)—NR$^1$—; —NR$^1$—S(=O)—NR$^1$—; —NR$^1$—S(=O)$_2$—NR$^1$—; R$^2$ is hydrogen, $C_{1-10}$alkyl, $C_{2-10}$alkenyl, $C_{2-10}$alkynyl, R$^{20}$, each of said groups representing R$^2$ may optionally be substituted where possible with one or more substituents each independently being selected from —S; —O; R$^{15}$; hydroxy; halo; nitro; cyano; R$^{15}$—O—; SH; R$^{15}$—S—; formyl; carboxyl; R$^{15}$—C(=O)—; R$^{15}$—O—C(=O)—; R$^{15}$—C(=O)—O—; R$^{15}$—O—C(=O)—O—; —SO$_3$H; R$^{15}$—S(=O)—; R$^{15}$—S(=O)—; R$^5$R$^6$N; R$^5$R$^6$N—$C_{1-6}$alkyl; R$^5$R$^6$N—$C_{3-7}$cycloalkyl; R$^5$R$^6$N—$C_{1-6}$alkyloxy; R$^5$R$^6$N—C(=O)—; R$^5$R$^6$N—C(=S)—; R$^5$R$^6$N—C(=O)—NH—; R$^5$R$^6$N—C(=S)—NH—; R$^5$R$^6$N—S(=O)$_n$—; R$^5$R$^6$N—S(=O)—NH—; R$^{15}$—C(=S)—; R$^{15}$—C(=O)—NH—; R$^{15}$—O—C(=O)—NH—; R$^{15}$—S(=O)$_n$—NH—; R$^{15}$—O—S(=O)$_n$—NH—; R$^{15}$—C(=S)—NH—; R$^{15}$—O—(=S)—NH—; R$^{17}$R$^{18}$N—Y$_{1a}$—; R$^{17}$R$^{18}$N—Y$_2$—NR$^{16}$—Y$_1$; R$^{15}$—Y$_2$—NR$^{19}$—Y$_1$—; H—Y$_2$—NR$^{19}$—Y$_1$—; R$^3$ is hydrogen; halo; $C_{1-6}$alkyl; cyano; or polyhalo$C_{1-6}$alkyl; R$^4$ is a monocyclic, bicyclic or tricyclic saturated heterocycle; a monocyclic, bicyclic or tricyclic partially saturated heterocycle or a monocyclic, bicyclic or tricyclic aromatic heterocycle, each of said heterocycles optionally being substituted where possible with one or more substituents each independently being selected from =S; =O; R$^{15}$; hydroxy; halo; nitro; cyano; R$^{15}$—O—; SH; R$^{15}$—S—; formyl; carboxyl; R$^{15}$—C(=O)—; R$^{15}$—O—C(=O)—; R$^{15}$—C(=O)—O—; R$^{15}$—O—C(=O)—O—; —SO$_3$H; R$^{15}$—S(=O)—; R$^{15}$—S(=O)$_2$—; R$^5$R$^6$N; R$^5$R$^6$NC$_{1-6}$alkyl; R$^5$R$^6$NC$_{3-7}$cycloalkyl; R$^5$R$^6$NC$_{1-6}$alkyloxy; R$^5$R$^6$N—C(=O)—; R$^5$R$^6$N—C(=S)—; R$^5$R$^6$N—C(=O)—NH—; R$^5$R$^6$N—C(=S)—NH—; R$^5$R$^6$N—S(=O)$_n$—; R$^5$R$^6$N—S(=O)$_n$—NH—; R$^{15}$—C(=S)—; R$^{15}$—C(=O)—NH—; R$^{15}$—O—C(=O)—NH—; R$^{15}$—S(=O)$_n$—NH—; R$^{15}$—O—S(=O)$_n$—NH—; R$^{15}$—C(=S)—NH—; R$^{15}$—O—C(=S)—NH—; R$^{17}$R$^{18}$N—Y$_{1a}$; R$^{17}$R$^{18}$N—Y$_2$—NR$^{16}$—Y$_1$—; R$^{15}$—Y$_2$—NR—Y$_1$; H—Y$_2$NR$^{19}$—Y$_1$—; R$^5$ and R$^6$ each independently are hydrogen, R$^8$, —Y$_1$—NR$^9$—Y$_2$—NR$^{10}$R$^{11}$, —Y$_1$—NR$^9$—Y$_1$—R$^8$, —Y$_1$—NR$^9$R$^{10}$, or R$^5$ and R$^6$ may together with the nitrogen to which they are attached form a saturated or partially saturated monocyclic 3 to 8 membered heterocycle or an aromatic 4 to 8 membered monocyclic heterocycle, each of said heterocycles may optionally be substituted with one or more substituents selected from R$^{12}$, R$^{13}$ and R$^{14}$, or each of said heterocycles may optionally be fused with a benzene ring, said benzene ring being optionally substituted with one or more substituents selected from R$^{12}$, R$^{13}$ and R$^{14}$; R$^7$ is $C_{1-6}$alkyl, $C_{1-6}$alkyloxy, amino, mono- or di($C_{1-6}$alkyl)amino or polyhalo$C_{1-6}$alkyl; R$^8$ is R$^9$, R$^{10}$ and R$^{11}$ alkyl; $C_{2-6}$alkenyl; $C_{2-6}$alkynyl; a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; a monocyclic, bicyclic or tricyclic aromatic heterocycle; $C_{1-6}$alkyl substituted with a monocyclic, bicyclic or tricyclic saturated carbocycle or with a monocyclic, bicyclic or tricyclic partially saturated carbocycle or with a monocyclic, bicyclic or tricyclic aromatic carbocycle or with a monocyclic, bicyclic or tricyclic saturated heterocycle or with a monocyclic, bicyclic or tricyclic partially saturated heterocycle or with a monocyclic, bicyclic or tricyclic aromatic heterocycle; each of said groups representing R$^8$ may optionally be substituted with one or more substituents selected from R$^{12}$, R$^{13}$ and R$^{14}$; R$^9$, R$^{10}$ and R$^{11}$ each independently are hydrogen or R$^8$, or any two of R$^9$, R$^{10}$ and R$^{11}$ may together be $C_{1-6}$alkanediyl or $C_{2-6}$alkenediyl thereby forming a saturated or partially saturated monocyclic 3 to 8 membered heterocycle or an aromatic 4 to 8 membered monocyclic heterocycle together with the nitrogen atoms to which they are attached, each of said heterocycles may optionally be substituted with one or more substituents selected from R$^{12}$, R$^{13}$ and R$^{14}$; R$^{12}$, R$^{13}$ and R$^{14}$ each independently are hydrogen; R$^{15}$; hydroxy; halo; nitro; cyano; R$^{15}$—O—; SH; R$^{15}$—S—; formyl; carboxyl; R$^{15}$—C(=O)—; R$^{15}$—O—C(=O)—; R$^{15}$—C(=O)—O—; R$^{15}$—O—C(=O)—O—; —SO$_3$H; R$^{15}$—S(=O)—; R$^{15}$—S(=O)$_2$—; R$^{15}$R$^{16}$N—S(=O)—; R$^{15}$R$^{16}$N—S(=O)$_2$—; R$^{17}$R$^{18}$N—Y$_1$—; R$^{17}$R$^{18}$N—Y$_2$—NR$^{16}$—Y$_1$—; R$^{15}$—Y$_2$—NR$^{19}$—Y$_1$—; H—Y$_2$NR$^{19}$—Y$_1$—; oxo, or any two of R$^{12}$, R$^{13}$ and R$^{14}$ may together be $C_{1-6}$alkanediyl or $C_{2-6}$alkenediyl thereby forming a saturated or partially saturated monocyclic 3 to 8 membered carbo-or heterocycle or an aromatic 4 to 8 membered monocyclic carbo- or heterocycle together with the atoms to which they are attached, or any two of R$^{12}$, R$^{13}$ and R$^{14}$ may together be —O—(CH$_2$)$_r$—O— thereby forming a saturated, partially saturated or aromatic monocyclic 4 to 8 membered carbo or heterocycle together with the atoms to which they are attached; R$^{15}$ is $C_{1-6}$alkyl, a monocyclic, bicyclic or tricyclic saturated heterocycle; $C_{1-6}$alkyl substituted with a monocyclic, bicyclic or tricyclic saturated carbocycle or with a monocyclic, bicyclic or tricyclic aromatic carbocycle; R$^{16}$, R$^{17}$, R$^{18}$ and R$^{19}$ each independently are hydrogen or R$^{15}$, or R$^{17}$ and R$^{18}$, or R$^{15}$ and R$^{19}$ may together be $C_{1-6}$alkanediyl or $C_{2-6}$alkenediyl thereby forming a saturated or partially saturated monocyclic 3 to 8 membered heterocycle or an aromatic 4 to 8 membered monocyclic heterocycle, each of said heterocycles may optionally be substituted with one or more substituents selected from R$^{12}$, R$^{13}$ and R$^{14}$; or R$^{17}$ and R$^{18}$ together with R$^{16}$ may be $C_{1-6}$alkanediyl or $C_{2-6}$alkenediyl thereby forming a saturated or partially saturated monocyclic 3 to 8 membered heterocycle or an aromatic 4 to 8 membered monocyclic heterocycle together with the nitrogen atoms to which they are attached, each of said heterocycles may optionally be substituted with one or more substituents selected from R$^{12}$, R$^{13}$ and R$^{14}$; R$^{20}$ is a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; a monocyclic, bicyclic or tricyclic aromatic heterocycle; $R^{21}$ is a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; a monocyclic, bicyclic or tricyclic aromatic heterocycle, each of said carbocycles or heterocycles representing $R^{21}$ may optionally be substituted with one or more substituents selected from $R^{12}$, $R^{13}$ and $R^{14}$; $Y_{1a}$ is —$Y_3$—S(=O)—$Y_4$—; —$Y_3$—S(=O)$_2$—$Y_4$—, —$Y_3$—C(=O)—$Y_4$, —$Y_3$—C(=S)—$Y_4$, —$Y_3$—O—$Y_4$—, —$Y_3$—S—$Y_4$—, —$Y_5$—O—C(=O)—$Y_4$— or —$Y_3$—C(=O)—O—$Y_4$—; $Y_1$ or $Y_2$ each independently are a direct bond, —$Y_3$—S(=O)—$Y_4$—; —$Y_3$—S(=O)$_2$—$Y_4$—, —$Y_3$—C(=O)—$Y_4$—, —$Y_3$—C(=S)—$Y_4$, —$Y_3$—O—$Y_4$, —$Y_3$—S—$Y_4$, —$Y_3$—O—C(=O)—$Y_4$— or —$Y_3$—C(=O)—O—$Y_4$—; $Y_3$ or $Y_4$ each independently are a direct bond, $C_{1-6}$alkanediyl, $C_{2-6}$alkenediyl or $C_{2-6}$alkynediyl; n is 1 or 2; m is 1 or 2: p is 1 or 2; r is 1 to 5; s is 1 to 3; aryl is phenyl or phenyl substituted with one, two, three, four or five substituents each independently selected from halo, $C_{1-6}$alkyl, $C_{3-7}$cycloalkyl, $C_{1-6}$alkyloxy, cyano, nitro, polyhalo$C_{1-6}$alkyl and polyhalo$C_{1-6}$alkyloxy; provided that —X—$R^2$ and/or $R^3$ is other than hydrogen; and provided that -Z—$R^4$ is other than

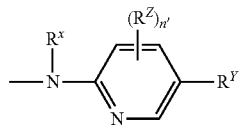

wherein $R^x$ is hydrogen, aryl, $C_{1-6}$alkylcarbonyl, $C_{1-6}$alkyl, $C_{1-6}$alkyloxycarbonyl, $C_{1-6}$alkyl substituted with $C_{1-6}$alkyloxycarbonyl; $R^y$ is halo, $C_{1-6}$alkyl, cyano, aminocarbonyl, nitro, trihalomethyl, trihalomethyloxy or $C_{1-6}$alkyl substituted with cyano or aminocarbonyl; $R^z$ is hydroxyl, halo, $C_{1-6}$alkyl, $C_{1-6}$alkyloxy, cyano, aminocarbonyl, nitro, amino, trihalomethyl, trihalomethyloxy or $C_{1-6}$alkyl substituted with cyano or aminocarbonyl; and n' is 0, 1, 2 or 3; and provided that -Z—$R^4$ is other than $C_{1-6}$alkyl substituted with indolyl which may be substituted with one, two, three, four or five substituents each independently selected from halo, hydroxyl, $C_{1-6}$alkyl, $C_{1-6}$alkyloxy, cyano, aminocarbonyl, $C_{1-6}$alkyloxycarbonyl, formyl, nitro, amino, trihalomethyl, trihalomethyloxy and $C_{1-6}$alkylcarbonyl (see U.S. patent application Ser. No. 10/493,452, filed Apr. 23, 2004, published as US 2005/0004125 on Jan. 6, 2005, and issued on Apr. 7, 2009 as U.S. Pat. No. 7,514,445).

In certain embodiments, the GSK3 inhibitors are compounds of the following formula:

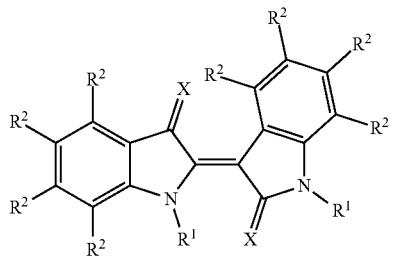

and salts thereof, wherein: each X is independently O or NOR$^A$; R$^A$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group; $R^1$ is hydrogen, optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, optionally substituted aryl, optionally substituted heteroaryl, or a nitrogen protecting group; and $R^2$ is hydrogen, halogen, optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, optionally substituted aryl, or optionally substituted heteroaryl.

In certain embodiments, at least one X is O. In certain embodiments, at least one X is NOH. In certain embodiments, both X are O. In certain embodiments, at least one X is NOR$^A$, wherein R$^A$ is a oxygen protecting group. In certain embodiments, at least one $R^1$ is hydrogen. In certain embodiments, both $R^1$ are hydrogen. In certain embodiments, at least one $R^2$ is hydrogen. In certain embodiments, at least one $R^2$ is halogen. In certain embodiments, at least one $R^2$ is bromide. In certain embodiments, all $R^2$ are hydrogen. In certain embodiments, at least one $R^2$ is unsubstituted alkyl. In certain embodiments, at least one $R^2$ is substituted alkyl.

In certain embodiments, the GSK3 inhibitor is KIN 001-043:

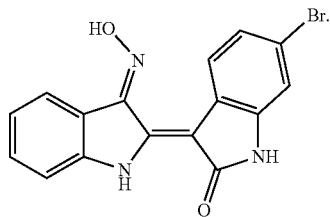 [SMILES: O=C1Nc2cc(Br)ccc2/C1=C1/Nc2ccccc2/C1=N\O]

In certain embodiments, the GSK3 inhibitor is indirubin-monoxime:

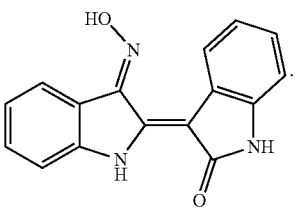 [SMILES: O=C1Nc2ccccc2/C1=C1/Nc2ccccc2/C1=N\O]

In certain embodiments, the GSK3 inhibitor is indirubin:

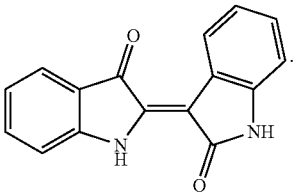 [SMILES: O=C1Nc2ccccc2/C1=C1/Nc2ccccc2C1=O]

In certain embodiments, the GSK3 inhibitors are selected from a group consisting of KIN 001-043, AR-A014418, TWS-119, Indirubin-monoxime, indirubin, beryllium, copper, lithium, mercury, tungsten, 6-BIO, dibromocantharelline, hymenialdisine, CT98014, CT98023, CT99021, SB-216763, SB-415286, AZD-1080, alsterpaullone, cazpaullone, kenpaullone, manzamine A, palinurine, tricantine, TDZD-8, NP00111, NP031115, tideglusib, HMK-32, and L803-mts.

In certain embodiments, the MET inhibitors are compounds of the following formula:

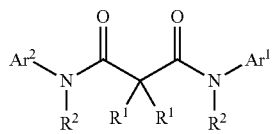

and salts thereof, wherein: $Ar^1$ is optionally substituted aryl or optionally substituted heteroaryl; $Ar^2$ is optionally substituted aryl or optionally substituted heteroaryl; each $R^1$ is independently hydrogen, optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, optionally substituted aryl, or optionally substituted heteroaryl; and each $R^2$ is independently hydrogen, optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, optionally substituted aryl, optionally substituted heteroaryl, or a nitrogen protecting group; or two $R^1$ are taken together to form an optionally substituted carbocyclyl or optionally substituted heterocyclyl; or $R^1$ and $R^2$ are taken together to form an optionally substituted carbocyclyl or optionally substituted heterocyclyl.

In certain embodiments, $Ar^1$ is unsubstituted phenyl. In certain embodiments, $Ar^1$ is substituted phenyl. In certain embodiments, $Ar^2$ is unsubstituted phenyl. In certain embodiments, $Ar^2$ is substituted phenyl. In certain embodiments, at least one $R^1$ is optionally substituted alkyl. In certain embodiments, both $R^1$ are independently optionally substituted alkyl. In certain embodiments, two $R^1$ are taken together to form a optionally substituted heterocyclyl. In certain embodiments, two $R^1$ are taken together to form a optionally substituted carbocyclyl. In certain embodiments, two $R^1$ are taken together to form a optionally substituted cyclopropyl. In certain embodiments, two $R^1$ are taken together to form a optionally substituted cyclobutyl. In certain embodiments, two $R^1$ are taken together to form a optionally substituted cyclopentyl. In certain embodiments, two $R^1$ are taken together to form a optionally substituted cyclohexyl. In certain embodiments, two $R^1$ are taken together to form a optionally substituted cycloheptyl. In certain embodiments, two $R^1$ are taken together to form a optionally substituted cyclooctyl. In certain embodiments, $R^1$ and $R^2$ are taken together to form an optionally substituted carbocyclyl. In certain embodiments, $R^1$ and $R^2$ are taken together to form an optionally substituted heterocyclyl. In certain embodiments, $R^1$ and $R^2$ are taken together to form an optionally substituted heterocyclyl. In certain embodiments, $R^1$ and $R^2$ are taken together to form an optionally substituted 4-membered heterocyclyl. In certain embodiments, $R^1$ and $R^2$ are taken together to form an optionally substituted 5-membered heterocyclyl. In certain embodiments, $R^1$ and $R^2$ are taken together to form an optionally substituted 6-membered heterocyclyl. In certain embodiments, $R^1$ and $R^2$ are taken together to form an optionally substituted 7-membered heterocyclyl. In certain embodiments, $R^1$ and $R^2$ are taken together to form an optionally substituted, unsaturated 6-membered heterocyclyl.

In certain embodiments, the MET inhibitor is BMS 777607:

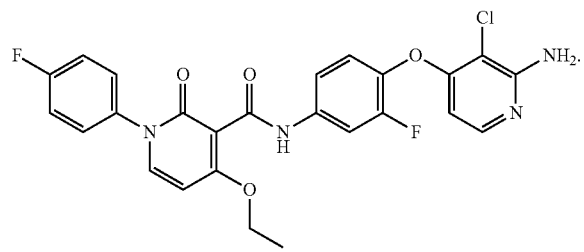 [SMILES: CCOc1ccn(-c2ccc(F)cc2)c(=O)c1C(=O)Nc1ccc(Oc2ccnc(N)c2Cl)c(F)c1]

In certain embodiments, the MET inhibitor is Foretinib:

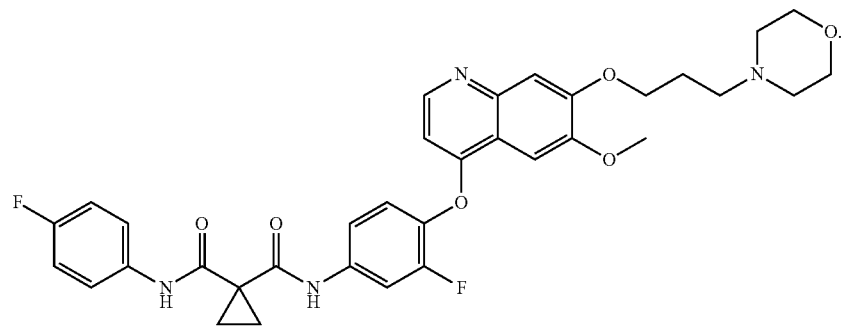 [SMILES: COc1cc2c(Oc3ccc(NC(=O)C4(C(=O)Nc5ccc(F)cc5)CC4)cc3F)ccnc2cc1OCCCN1CCOCC1]

In certain embodiments, the MET inhibitor is XL-184:

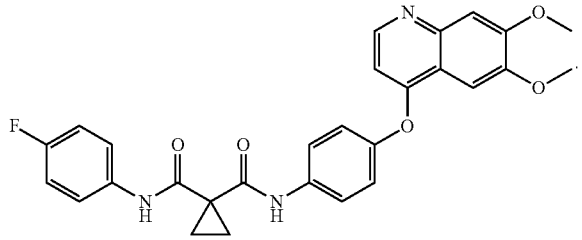 [SMILES: COc1cc2nccc(Oc3ccc(NC(=O)C4(C(=O)Nc5ccc(F)cc5)CC4)cc3)c2cc1OC]

In certain embodiments the MET inhibitors are selected from the group consisting of AMG-208, AMG-337, AMG-458, PHA-665752, SU11274, NPS-1034, SGX-523, BMS-777607, tepotinib, BMS-794833, NVP-BVU972, MK-2461, MGCD-265, golvatinib, JNJ-38877605, BMS-754807, PF-04217903, savolitinib, crizotinib, tivantinib, cabozantinib, foretinib, capmatinib (INC280), tepotinib, BMS-794833, BMS-817378, DCC-2618, merestinib (LY2801653), Altiratinib), BMS-794833, c-Met inhibitor 1, Ningetinib, MK-2461, NPS-1034, and SCR-1481B1.

In certain embodiments, the kinase inhibitors are compounds of the following formula:

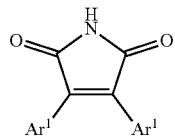

and salts thereof, wherein each $Ar^1$ is independently optionally substituted aryl or optionally substituted heteroaryl.

In certain embodiments, at least one $Ar^1$ is unsubstituted aryl. In certain embodiments, at least one $Ar^1$ is substituted aryl. In certain embodiments, both $Ar^1$ are unsubstituted aryl. In certain embodiments, both $Ar^1$ are substituted aryl. In certain embodiments, at least one $Ar^1$ is unsubstituted heteroaryl. In certain embodiments, at least one $Ar^1$ is substituted heteroaryl. In certain embodiments, both $Ar^1$ are unsubstituted heteroaryl. In certain embodiments, both $Ar^1$ are substituted heteroaryl. In certain embodiments, the unsubstituted or substituted heteroaryl is selected from: pyrrolyl, furanyl, thiophenyl, imidazolyl, pyrazolyl, oxazolyl, isoxazolyl, thiazolyl, isothiazolyl triazolyl, oxadiazolyl, thiadiazolyl, tetrazolyl, pyridinyl, pyridazinyl, pyrimidinyl, pyrazinyl, triazinyl, tetrazinyl, azepinyl, oxepinyl, thiepinyl, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, purinyl, naphthyridinyl, pteridinyl, quinolinyl, isoquinolinyl, cinnolinyl, quinoxalinyl, phthalazinyl, quinazolinyl, phenanthridinyl, dibenzofuranyl, carbazolyl, acridinyl, phenothiazinyl, phenoxazinyl and phenazinyl. In certain embodiments, at least one $Ar^1$ is substituted indolyl. In certain embodiments, both $Ar^1$ are substituted indolyl.

In certain embodiments, the kinase inhibitor is Ro 31-8220:

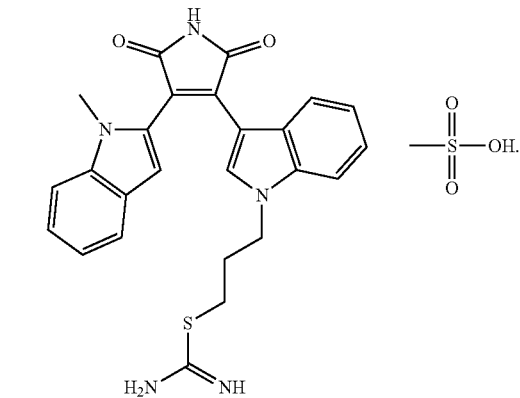

In certain embodiments, cell culture media are used to culture and maintain cells. In some embodiments, the cell culture medium is chemically defined medium. In some embodiments, cell culture medium is serum-free medium, e.g., mTeSR1™ medium (StemCell Technologies, Vancouver, BC). In some embodiments, the culture medium comprises one or more supplements, such as, but not limited to N2 and B27. In some embodiments, the cell culture medium comprises a serum replacement composition. In some embodiments, the cell culture medium comprises knock-out serum replacement medium. In some embodiments, the cell culture medium does not comprise a serum replacement composition.

In some embodiments, the cell culture medium comprises a basal medium to which one or more supplements are added, such as: N2 supplement, B27 supplement, glutamax, pyruvate, penicillin-streptomycin, and/or BSA (e.g., from Sigma). In certain embodiments the basal medium is DMEM/F12, Neurobasal medium, or a mixture thereof.

In some aspects, the present disclosure provides pharmaceutical compositions comprising a compound, or a pharmaceutically acceptable salt thereof, and optionally a pharmaceutically acceptable excipient for use in treating and/or preventing a neurological disease, psychiatric disorder, or central nervous system injury characterized by deficient expression or function of KCC2. In certain embodiments, the pharmaceutical composition described herein comprises a compound, or a pharmaceutically acceptable salt thereof, and a pharmaceutically acceptable excipient. In certain embodiments, the compound is selected from a group consisting of kinase inhibitors, Feline McDonough sarcoma-like tyrosine kinase 3 (FLT3) inhibitors, glycogen synthase kinase 3 (GSK3) inhibitors, gamma-aminobutyric acid (GABA) inhibitors, GABA reuptake inhibitors, monoamine oxidase inhibitors (MAOI), norepinephrine reuptake inhibitor (NRI), dopamine antagonist, Sirtuin 1 (SIRT1) activators, transient receptor potential cation channel subfamily V member 1 (TRPV1) activators, monoamine transporter activators, tropomyosin receptor kinase B (TrkB) agonists, ampakines, and salts thereof. In certain embodiments, the compound is selected from a group consisting of (E)-(4-(2-(1H-indazol-3-yl)vinyl)phenyl)(piperazin-1-yl)methanone (KW-2449), 2Z,3E)-6'-bromo-3-(hydroxyimino)-[2,3'-biindolinylidene]-2'-one (KIN 001-043), N-(2-diethylaminoethyl)-5-[(Z)-(5-fluoro-2-oxo-1H-indol-3-ylidene)methyl]-2,4-dimethyl-1H-pyrrole-3-carboxamide (Sunitinib), 1-(2-(5-(2-(3-methyloxetan-3-yl)ethyl)-1H-benzo[d]imidazol-1-yl)quinolin-8-yl)piperidin-4-amine (Crenolanib), N'-[4-[(6,7-dimethoxy-4-quinolinyl)oxy]phenyl]-N-(4-fluorophenyl)-

1,1-cyclopropanedicarboxamide (XL-184), 3-((6-(3-aminophenyl)-7H-pyrrolo[2,3-d]pyrimidin-4-yl)methyl)phenol (TWS-119), (2Z,3E)-3-(hydroxyimino)-[2,3'-biindolinylidene]-2'-one (Indirubin-monoxime), resveratrol, piperine, and salts thereof. In certain embodiments, the compound is selected from the group consisting of, MET proto-oncogene, receptor tyrosine kinase (MET) inhibitors. In certain embodiments the compound is selected from the group of compounds listed in Table 2 and salts thereof. In certain embodiments the compound is selected from the group of compounds listed in Table 3 and salts thereof. In some aspects, the present disclosure provides pharmaceutical compositions comprising a compound, or a pharmaceutically acceptable salt thereof, and optionally a pharmaceutically acceptable excipient for use in treating and/or preventing ASD, RTT, epilepsy, schizophrenia, mental retardation, stroke, Fragile-X syndrome, traumatic brain injury, and spinal cord injury. In certain embodiments, the pharmaceutical composition described herein comprises a compound, or a pharmaceutically acceptable salt thereof, and a pharmaceutically acceptable excipient. In certain embodiments, the compound is selected from a group consisting of kinase inhibitors, Feline McDonough sarcoma-like tyrosine kinase 3 (FLT3) inhibitors, glycogen synthase kinase 3 (GSK3) inhibitors, gamma-aminobutyric acid (GABA) inhibitors, GABA reuptake inhibitors, monoamine oxidase inhibitors (MAOI), norepinephrine reuptake inhibitor (NRI), dopamine antagonist, Sirtuin 1 (SIRT1) activators, transient receptor potential cation channel subfamily V member 1 (TRPV1) activators, monoamine transporter activators, tropomyosin receptor kinase B (TrkB) agonists, ampakines, and salts thereof. In certain embodiments, the compound is selected from a group consisting of (E)-(4-(2-(1H-indazol-3-yl)vinyl)phenyl)(piperazin-1-yl)methanone (KW-2449), 2Z,3E)-6'-bromo-3-(hydroxyimino)-[2,3'-biindolinylidene]-2'-one (KIN 001-043), N-(2-diethylaminoethyl)-5-[(Z)-(5-fluoro-2-oxo-1H-indol-3-ylidene)methyl]-2,4-dimethyl-1H-pyrrole-3-carboxamide (Sunitinib), 1-(2-(5-(2-(3-methyloxetan-3-yl)ethyl)-1H-benzo[d]imidazol-1-yl)quinolin-8-yl)piperidin-4-amine (Crenolanib), N'-[4-[(6,7-dimethoxy-4-quinolinyl)oxy]phenyl]-N-(4-fluorophenyl)-1,1-cyclopropanedicarboxamide (XL-184), 3-((6-(3-aminophenyl)-7H-pyrrolo[2,3-d]pyrimidin-4-yl)methyl)phenol (TWS-119), (2Z,3E)-3-(hydroxyimino)-[2,3'-biindolinylidene]-2'-one (Indirubin-monoxime), resveratrol, piperine, and salts thereof. In certain embodiments, the compound is selected from the group consisting of, MET proto-oncogene, receptor tyrosine kinase (MET) inhibitors. In certain embodiments the compound is selected from the group of compounds listed in Table 2 and salts thereof. In certain embodiments the compound is selected from the group of compounds listed in Table 3 and salts thereof.

In certain embodiments, the compound described herein is provided in an amount in the pharmaceutical composition effective to treat and/or prevent ASD, RTT, epilepsy, schizophrenia, mental retardation, stroke, Fragile-X syndrome, traumatic brain injury, and spinal cord injury. In certain embodiments, the effective amount is a therapeutically effective amount. In certain embodiments, the effective amount is a prophylactically effective amount. In certain embodiments, the effective amount is an amount effective for treating a neurological disease in a subject in need thereof. In certain embodiments, the effective amount is an amount effective for preventing a neurological disease in a subject in need thereof. In certain embodiments, the effective amount is an amount effective for treating a psychiatric disorder in a subject in need thereof. In certain embodiments, the effective amount is an amount effective for preventing a psychiatric disorder in a subject in need thereof. In certain embodiments, the effective amount is an amount effective for reducing the risk of developing a disease (e.g., neurological disease or psychiatric disorder) in a subject in need thereof. In certain embodiments, the effective amount is an amount effective for treating a central nervous system injury in a subject in need thereof. In certain embodiments, the effective amount is an amount effective for enhancing the gene expression of KCC2 in a subject or cell.

In certain embodiments, the subject is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In some embodiments, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs).

Pharmaceutical compositions described herein can be prepared by any method known in the art of pharmacology. In general, such preparatory methods include bringing the compound described herein into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 μg and 1 μg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, in reducing the risk to develop a disease in a subject in need thereof, and/or in inhibiting the activity of a protein kinase in a subject or cell), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., neurological disease or psychiatric disorder) or central nervous system injury. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. In certain embodiments, the kits are useful for treating a disease (e.g., neurological disease or psychiatric disorder) or central nervous system injury in a subject in need thereof. In certain embodiments, the kits are useful for preventing a disease (e.g., neurological disease or psychiatric disorder) or central nervous system injuryin a subject in need thereof. In certain embodiments, the kits are useful for reducing the risk of developing a disease (e.g., neurological disease or psychiatric disorder) or central nervous system injuryin a subject in need thereof. In certain embodiments, the kits are useful for enhancing the gene expression of KCC2 in a subject or cell.

In certain embodiments, a kit described herein further includes instructions for using the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease (e.g., neurological disease or psychiatric disorder) or central nervous system injury in a subject in need thereof. In certain embodiments, the kits and instructions provide for preventing a disease (e.g., neurological disease or psychiatric disorder) or central nervous system injury in a subject in need thereof. In certain embodiments, the kits and instructions provide for reducing the risk of developing a disease (e.g., neurological disease or psychiatric disorder) or central nervous system injury a subject in need thereof. In certain embodiments, the kits and instructions provide for enhancing the gene expression of KCC2 in a subject or cell. A kit described herein may include one or more additional pharmaceutical agents described herein as a separate composition.

The collection of novel and specific KCC2 enhancing chemical compounds identified from the screening method will provide the basis of novel therapies that stimulate KCC2 expression to treat ASD, RTT, neurological diseases, psychiatric disorders, and central nervous system injuries. The screening for increased KCC2 expression in neurons may provide a readout for improved neuronal function through pathways affected by hit compounds. Moreover, increased KCC2 expression itself may have direct therapeutic benefits to ASD, RTT, neurological diseases, psychiatric disorders, and central nervous system injuries. In some aspects, a method of treating a subject comprises diagnosing a subject as having or being at risk of developing a neurologic, psychiatric, or central nervous system disorder and administering a KCC2 expression enhancing compound to the subject.

EXAMPLES

In order that the invention described herein may be more fully understood, the following examples are set forth. The examples described in this application are offered to illustrate the methods, compositions, and systems provided herein and are not to be construed in any way as limiting their scope.

Example 1. Identification of KCC2 Expression Enhancing Compounds.

Results

The development of a compound screening platform with RTT KCC2-2A-luciferase reporter neurons to identify KCC2 expression enhancing compounds are outlined in FIGS. 1A to 1D. The compounds screened were selected from LINCS (Library of Integrated Network-based Cellular Signatures) kinase inhibitor library and IRSF (International Rett Syndrome Foundation) SMART (Selected Molecular Agents for Rett Therapy) compound library. The compounds within both libraries include compounds that belong to one or more of the following compound classes: Feline McDonough sarcoma-like tyrosine kinase 3 (FLT3) inhibitors, glycogen synthase kinase 3 (GSK3) inhibitors, gamma-aminobutyric acid (GABA) inhibitors, GABA reuptake inhibitors, monoamine oxidase inhibitors (MAOI), norepinephrine reuptake inhibitor (NRI), dopamine antagonist, Sirtuin 1 (SIRT1) activators, transient receptor potential cation channel subfamily V member 1 (TRPV1) activators, monoamine transporter activators, tropomyosin receptor kinase B (TrkB) agonists, or ampakines.

The RTT KCC2-2A-luciferase reporter neurons were treated with the test compounds from the LINCS kinase inhibitor library and IRSF SMART compound library and incubated before being lysed. The cell lysate was divided into two parts to measure luciferase signal (KCC2 translation) and Cell-Titer Glow (CTG, amount of ATP). The luciferase signal was normalized to CTG for each well, and the Luc/CTG ratio was normalized to the in-plate DMSO negative control to calculate fold change ratio.

The list of hit compounds identified from the compound screening with RTT KCC2 reporter neurons are given in Table 1.

TABLE 1

List of hit compounds identified from compound screening with RTT KCC2 reporter neurons.

| Compound Name | Cellular Effect |
|---|---|
| KW-2449 | FLT3 inhibitor |
| KIN 001-043 | GSK3 inhibitor |
| AR-A014418 | GSK3 inhibitor |
| Nipecotic acid | GABA reuptake inhibitor |

TABLE 1-continued

List of hit compounds identified from compound screening with RTT KCC2 reporter neurons.

| Compound Name | Cellular Effect |
|---|---|
| Methysticin | Neuroprotective, MAOI, NRI |
| Trifluoperazine dihydrochloride | Dopamine Antagonist |
| Resveratrol | SIRT1 activator |
| Piperine | TRPV1 activator |
| Luteolin, Flacitran | Monoamine transporter activator |
| 7,8-Dihydroxyflavone | TrkB agonist |
| CX-614, BDP37 | Ampakine, Antidepressant |

The measure of KCC2 levels in cultured female ESC-derived human RTT neurons after Western blot analysis are shown in FIGS. 2A to 2D. Treatment with KW-2449, KIN 001-043, resveratrol, and piperine is shown to increase KCC2 expression in RTT neurons at varying concentrations. Further, FIGS. 3A to 3F show the molecular pathways through which hit compounds regulate KCC2 expression with cultured human RTT neurons derived from gene-targeted ESC.

Figure 6A:
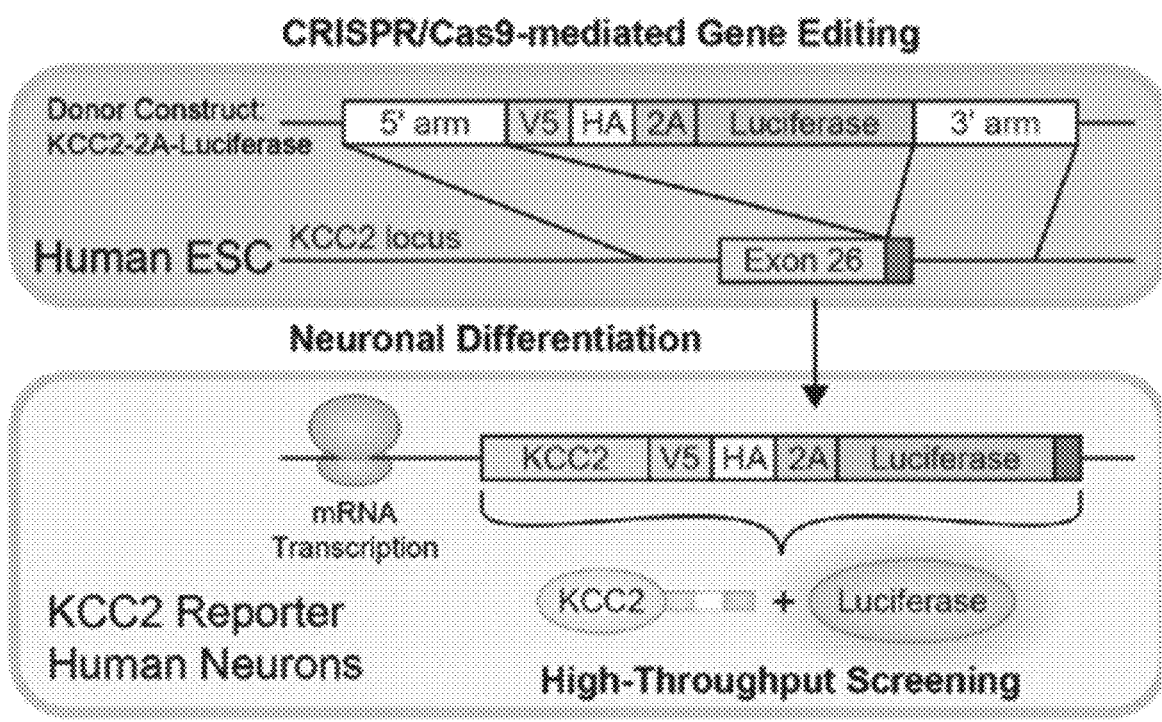
FIGS. 6A to 6I show development of a high-throughput screening platform with human KCC2 reporter neurons to identify a group of KCC2 expression-enhancing compounds and demonstrate that chemical compounds that are functionally analogous to primary hit KEECs increase KCC2 expression in cultured WT human neurons.
Figure 7A:
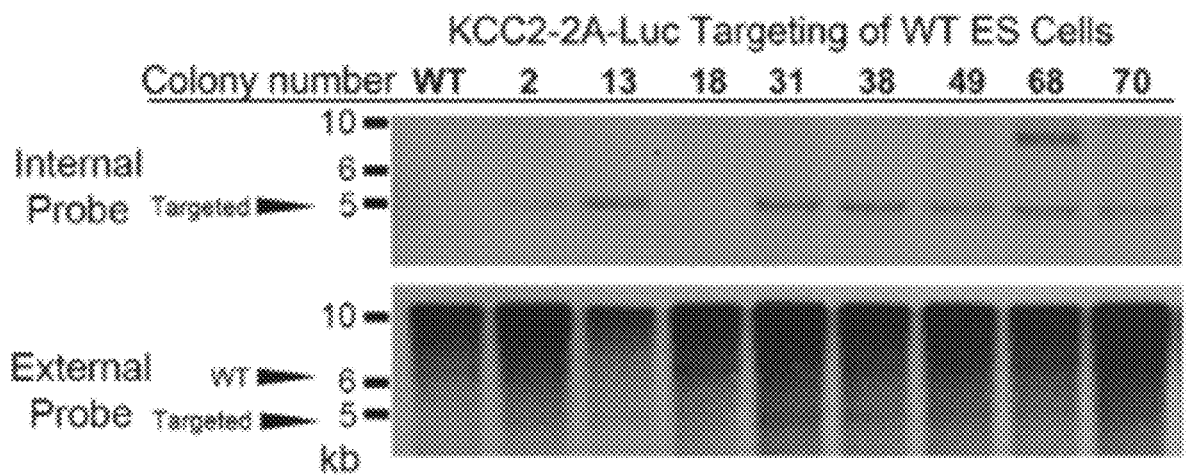
FIG. 7A shows a Southern blot assay confirming the correct insertion of luciferase to the KCC2 locus. The blot demonstrates that the luciferase reporter is inserted uniquely into the KCC2 locus for ES cell lines #13 and #31.
Figure 7B:
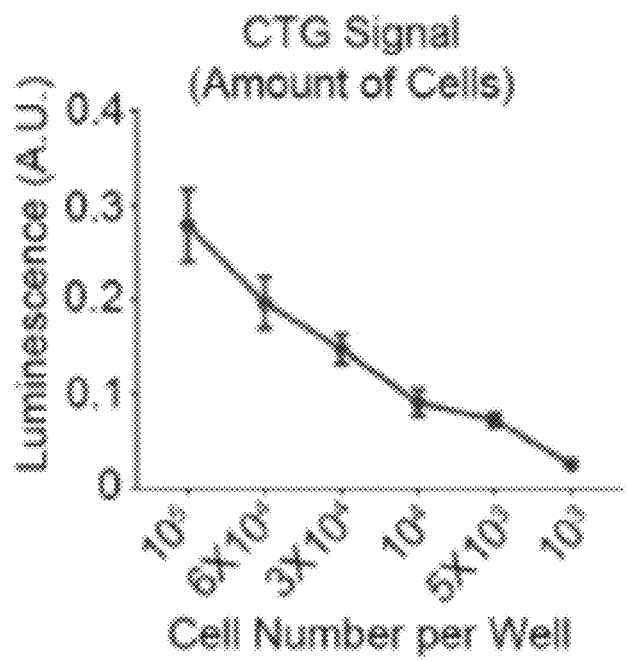
FIG. 7B shows results of assay development experiments with neurons derived from #13 and #31 KCC2 reporter ES cells support the successful insertion of luciferase reporter into the KCC2 locus.
Figure 7C:
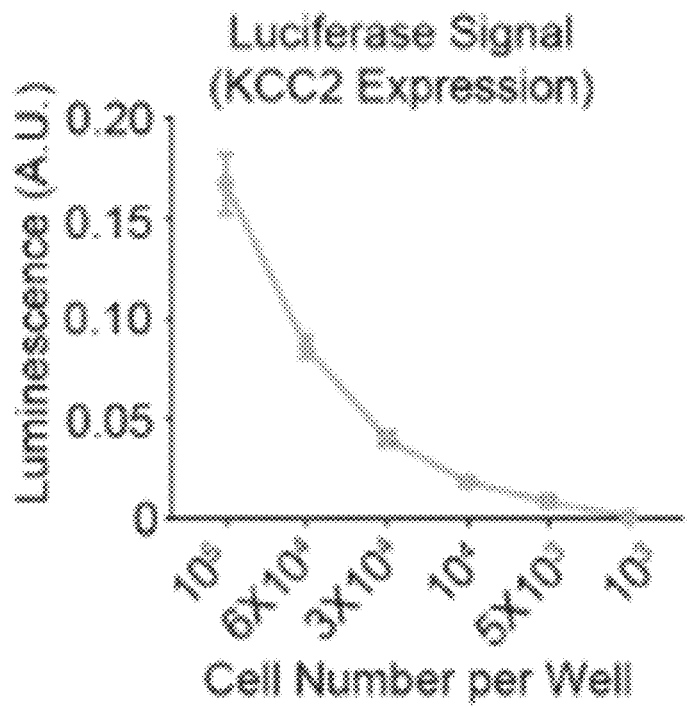
Figure 7D:
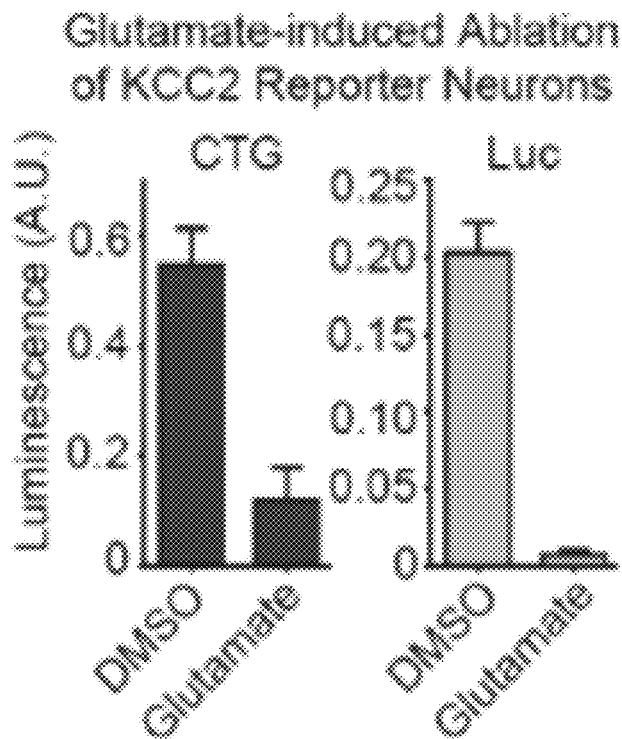
FIG. 7D shows that treatment of KCC2 reporter neurons with glutamate lead to neuronal death and vertically abolishes KCC2 luciferase signal, while some astrocyte population preserved as indicated by the remaining CTG signal.

In addition, CRISPR/Cas9 genome editing technology was utilized to insert a 2A-luciferase reporter gene directly before the stop codon of the endogenous KCC2 locus in human ES cells, thus creating wild type (WT) cells isogenic to the MECP2-null RTT human KCC2 reporter neurons. KCC2 expression reporter human neurons were differentiated from the gene-targeted ES cells and utilized as the substrate for unbiased compound screening (FIG. 6A; see also FIG. 1A). Sanger sequencing and Southern blot analyses were used to confirm correct editing (FIG. 7A), and assay development experiments were conducted to optimize the parameters for screening (FIG. 7B, 7C, 7D).

Figure 1B:
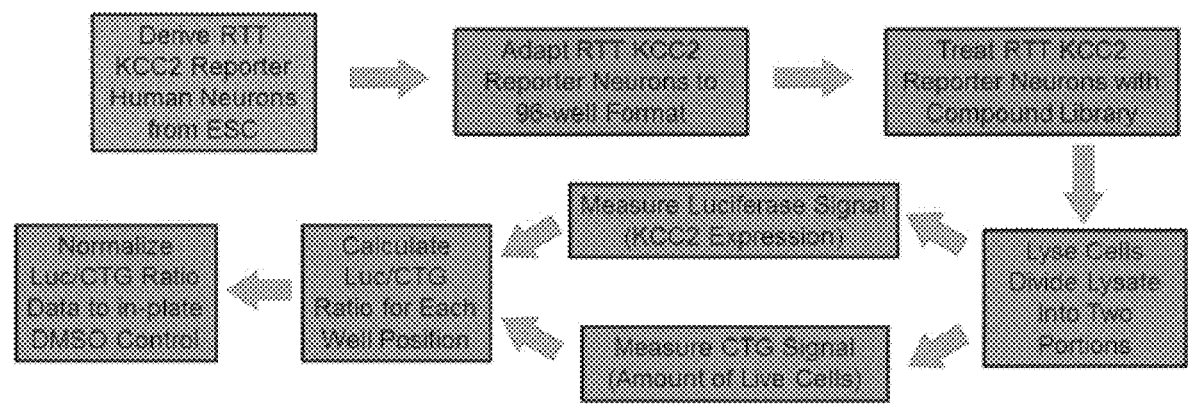
Figure 1C:
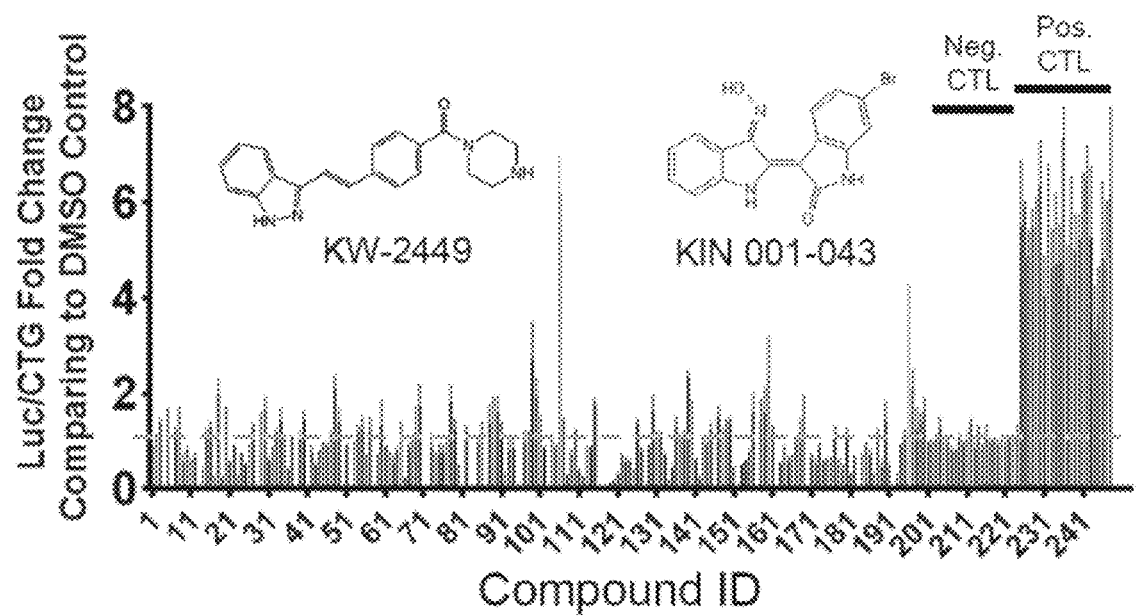
Figure 1D:
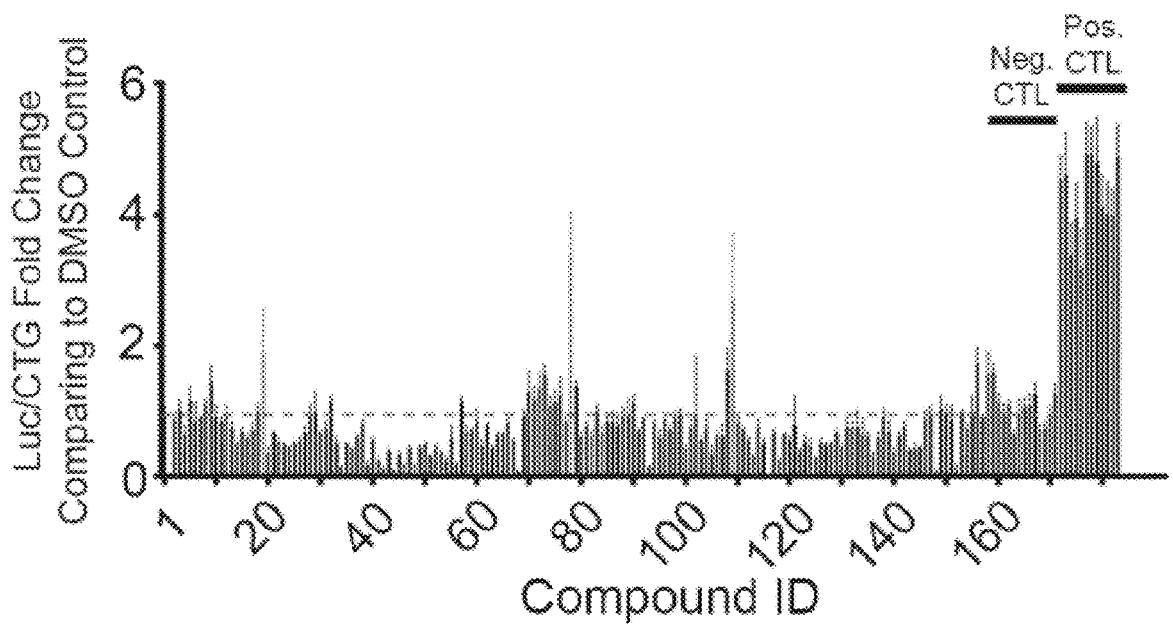
Figure 2A:
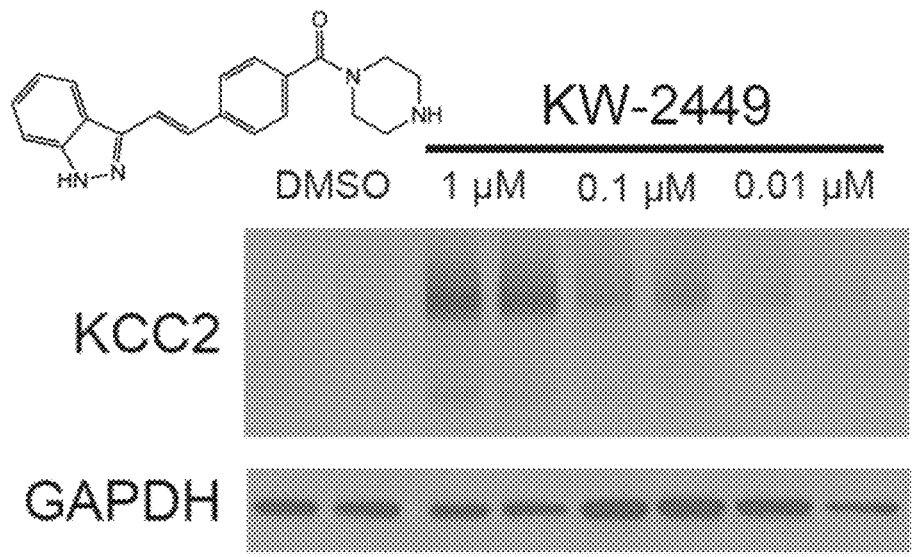
FIGS. 2A to 2D show validation of KCC2 expression enhancing compounds with cultured female ESC-derived human RTT neurons and the measurements of KCC2 levels in cultured RTT neurons.
Figure 2B:
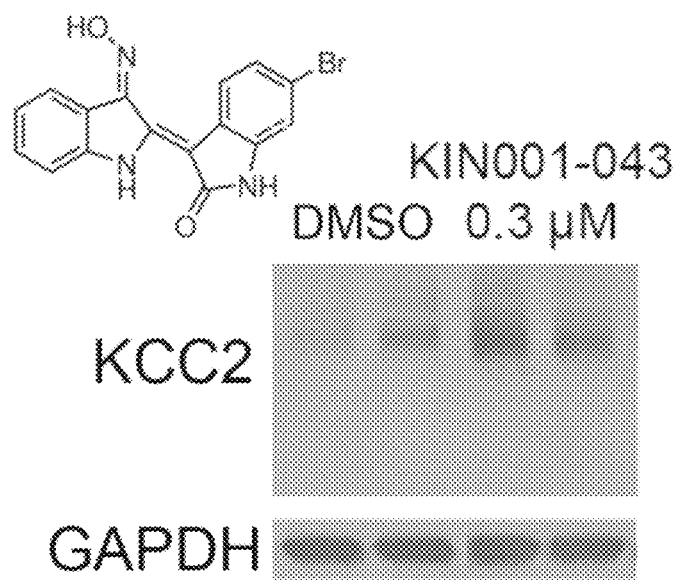
Figure 2C:
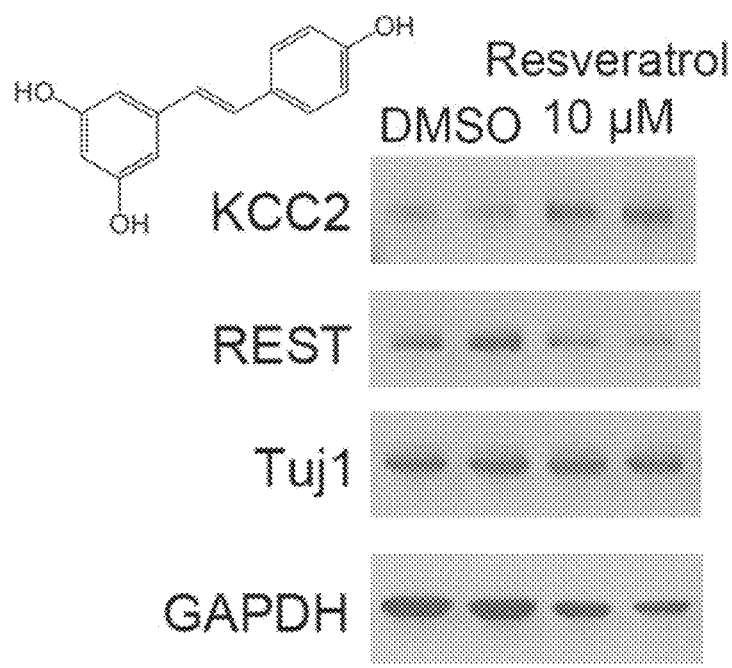
Figure 2D:
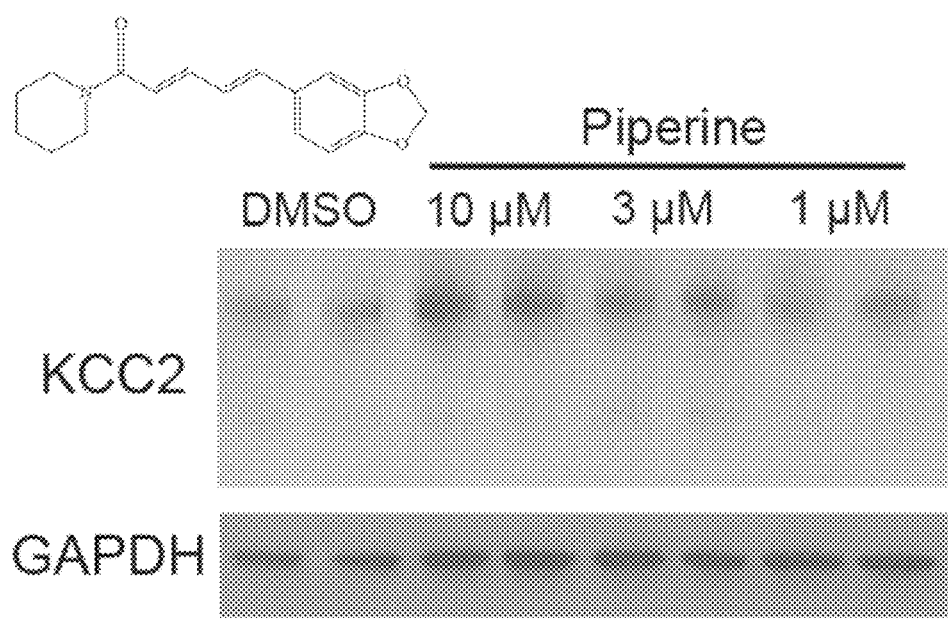
Figure 6B:
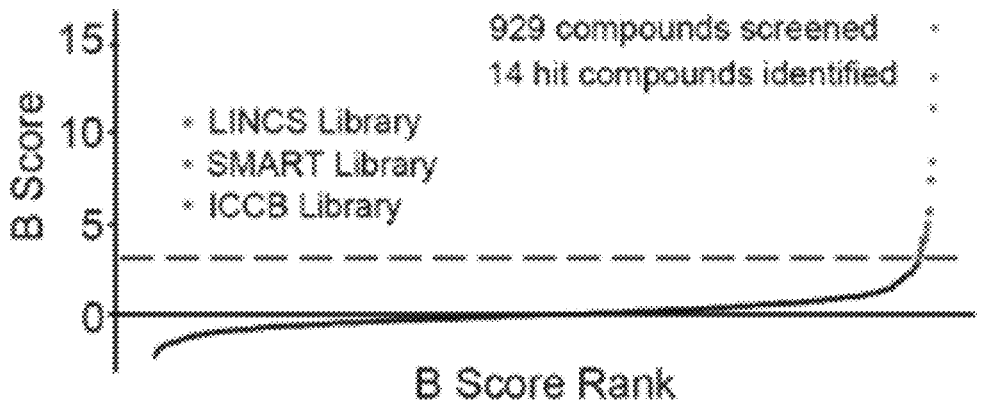
Figure 6C:
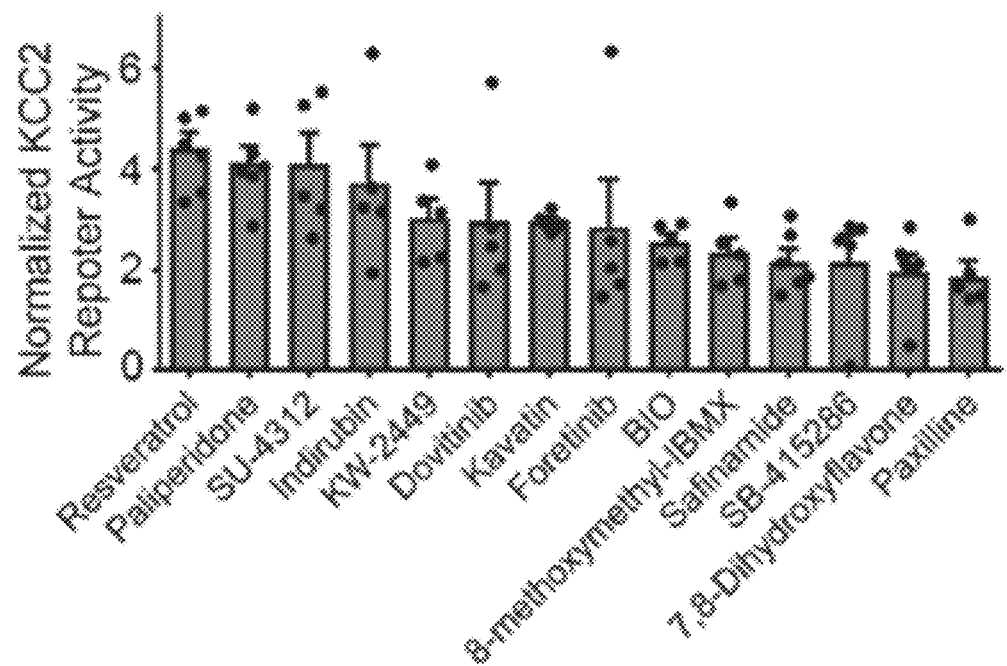

Gene-targeted KCC2 reporter cells were used in a HTS pipeline to screen for small molecule compounds that enhance KCC2 gene expression (FIG. 1B; note that reporter neurons were adapted to 384 well format for some screens, and the same workflow was used both for WT KCC2 reporter neurons and RTT KCC2 reporter neurons). Six replicate screens were performed in WT KCC2 reporter neurons using the LINCS and SMART libraries as well as the ICCB known bioactive library (FIG. 6B). From these screens, a total of 14 compounds were identified as hit KCC2 expression-enhancing compounds (KEECs, B score >3), including KW-2449, BIO (6-bromoindirubin-3'-oxime) and Resveratrol (FIG. 6C). Most KEECs that enhanced KCC2 expression in WT neurons, including KW-2449, BIO, and Resveratrol, were among the hits that had been found to induce a significant increase of KCC2 reporter activity in RTT neurons. A list of the top 14 hit compounds identified in the screens using WT human KCC2 reporter neurons is provided in Table 2.

TABLE 2

List of hit compounds identified from compound screening with wild type KCC2 reporter neurons (and certain analogs).

| Name | IUPAC Name | B Score | Class | Major targets |
|---|---|---|---|---|
| 7,8-Dihydroxyflavone | 7,8-Dihydroxyflavone | 4.01 | TrkB agonist | TrkB |
| 8-methoxymethyl-IBMX | 8-(Methoxymethyl)-1-methyl-3-(2-methylpropyl)-7H-purine-2,6-dione | 4.8 | Phosphodiesterase inhibitor | PDE1 |
| BIO | 2H-Indol-2-one, 6-bromo-3-[(3E)-1,3-dihydro-3-(hydroxyimino)-2H-indol-2-ylidene]-1,3-dihydro-, (3Z)- | 3.42 | GSK-3α/β inhibitor | GSK3 |
| Dovitinib | 1-amino-5-fluoro-3-(6-(4-methylpiperazin-1-yl)-1H-benzo[d]imidazol-2-yl)quinolin-2(1H)-one | 4.44 | RTK inhibitor | FLT3/c-Kit, FGFR1/3, VEGFR1, VEGFR4 |
| Foretinib | N1'-[3-fluoro-4-[[6-methoxy-7-(3-morpholinopropoxy)-4-quinolyl]oxy]phenyl]-N1-(4-fluorophenyl)cyclopropane-1,1-dicarboxamide | 4.05 | Kinase inhibitor | c-Met, VEGFR2;F FLT3 is also a target |
| Indirubin | (3Z)-3-(3-Oxo-1,3-dihydro-2H-indol-2-ylidene)-1,3-dihydro-2H-indol-2-one | 3.73 | N.A. | PLK1, PIN1, CDC25B |
| KW-2449 | (E)-(4-(2-(1H-indazol-3-yl)vinyl)phenyl)(piperazin-1-yl)methanone | 5.45 | Multi-target inhibitor | FLT3, ABL, ABL-T315I, Aurora kinase |
| Methysticin | (2R)-2-[(E)-2-(1,3-Benzodioxol-5-yl)ethenyl]-4-methoxy-2,3-dihydropyran-6-one | 7.17 | MAOI, NRI | CYP1A1 |
| Paliperidone | 9-Hydroxyrisperidone | 11.03 | D2 and 5HT2A receptor antagonist | Dopamine receptor, 5-HT2A, a 1/2 adrenergic receptors, H1 histaminergic |

TABLE 2-continued

List of hit compounds identified from compound screening with wild type KCC2 reporter neurons (and certain analogs).

| Name | IUPAC Name | B Score | Class | Major targets |
|------|------------|---------|-------|---------------|
| Paxilline | (2R,4bS,6aS,12bS,12cR,14aS)-5,6,6a,7,12,12b,12c,13,14,14a-Decahydro-4b-hydroxy-2-(1-hydroxy-1-methylethyl)- 12b,12c-dimethyl-2H-pyrano[2",3":5',6']benz[1',2':6,7]indeno[1,2-b]indol-3(4bH)-one | 4.1 | Potassium channel blocker | Potassium channels |
| Resveratrol | 3,5,4'-trihydroxy-trans-stilbene | 12.65 | MAOI, Anti-oxidant | Sirtuin1, PGC-1α |
| Safinamide | (2S)-2-14-103-fluorophenyl)methoxy]phenyl]methylamino]propanamide | 4.82 | MAOI | MAO, Sigma receptor |
| SB-415286 | 3-[(3-Chloro-4-hydroxyphenyl)-amino]-4-(2-nitrophenyl)-1H-pyrrol-2,5-dione | 5.58 | GSK-3 inhibitor | GSK-3 |
| SU-4312 | 3-(4-Dimethyl aminobenzylidenyl)-2-indolinone, 3-[[(4-Dimethyl-amino)phenyl] methylene] -1,3-dihydro-2H-indol-2-one | 3.55 | Kinase inhibitor | FLT1, VEGF, PDGF, neuronal NOS |
| Crenolanib | 1-(2-{5-[(3-Methyloxetan-3-yl)methoxy]-1H-benzimidazol-1-yl}quinolin-8-yl)piperidin-4-amine | N/A | Kinase inhibitor | FLT3, PDGFRα/β |
| Sunitinib | N-[2-(Diethylamino)ethyl]-5-[(Z)-(5-fluor-1,2-dihydro-2-oxo-3H-indol-3-yliden)-methyl]-2,4-dimethyl-1H-pyrrol-3-carboxamid | N/A | RTK inhibitor | PDGFRs, VEGFRs, c-KIT |
| XL184 (Cabozantinib) | N-(4-((6,7-Dimethoxyquinolin-4-yl)oxy)phenyl)-N'-(4-fluorophenyl)cyclopropane-1,1-dicarboxamide | N/A | Kinase inhibitor | c-Met, VEGFR2, AXL, RET |
| TWS-119 | 3-[6-(3-Amino-phenyl)-7H-pyrrolo[2,3,-d]pyrimidin-4-yloxy]-phenol | N/A | GSK3 inhibitor | GSK3P |
| Indirubin-monoxiome | 3-[1,3-dihydro-3-(hydroxyimino)-2H-indol-2-ylidene]-1,3-dihydro-2H-indol-2-one | N/A | GSK3 inhibitor | GSK3, CDK1/5 |

Note:
The compounds with the description 'N/A' in the B-score field are analog compounds of primary hit compounds identified from screening.

Figure 4A:
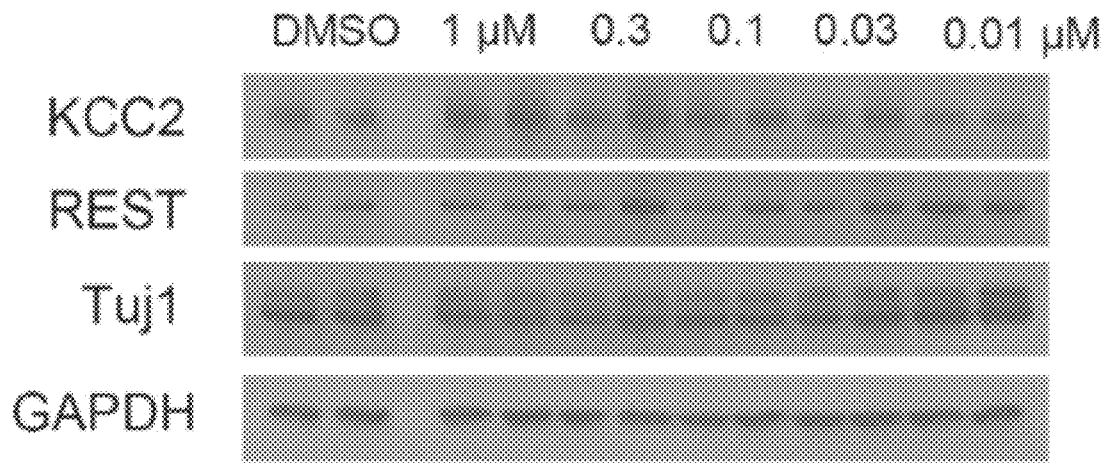
FIGS. 4A to 4E show that treatment with identified KEECs increases KCC2 expression in cultured human WT neurons.
Figure 4B:
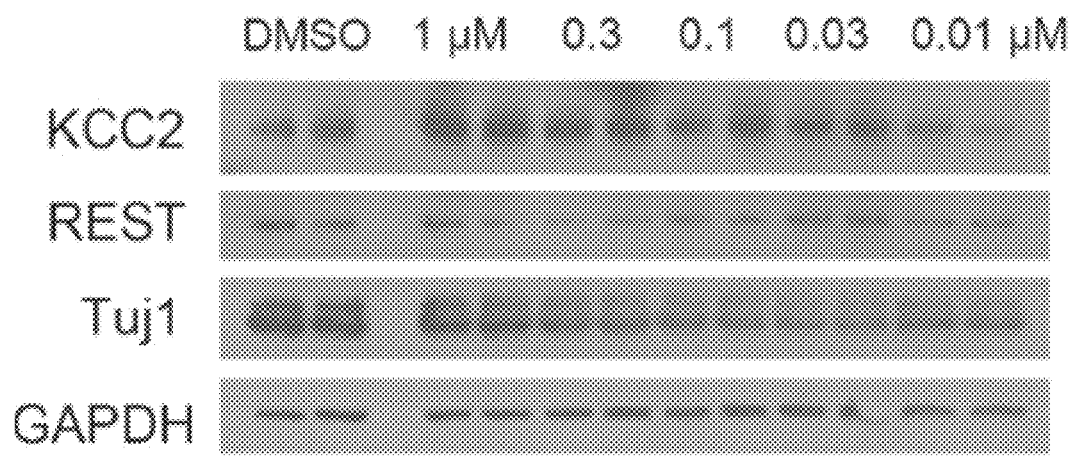
Figure 4C:
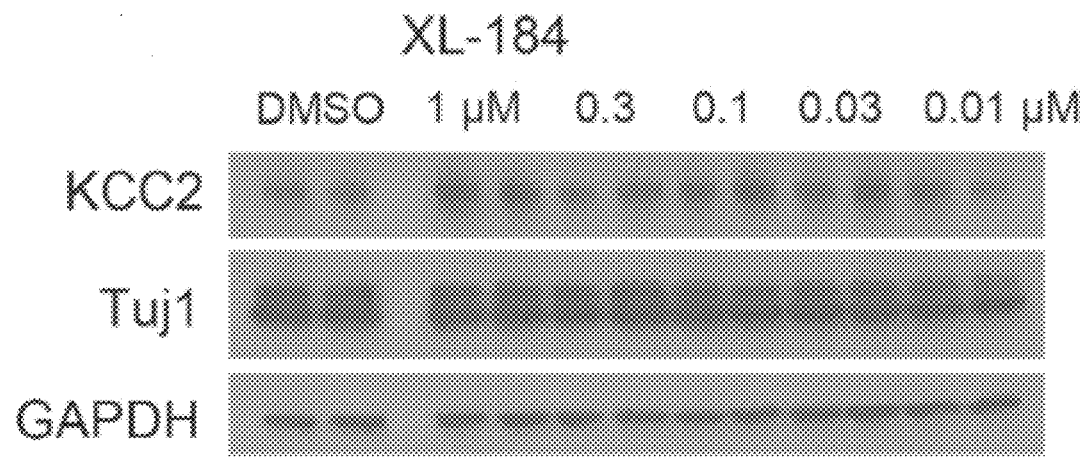
Figure 4D:
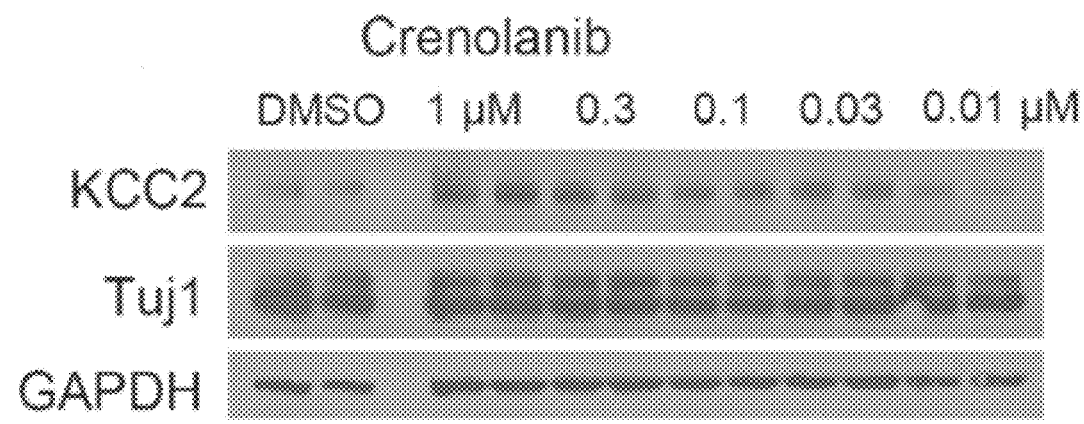
Figure 4E:
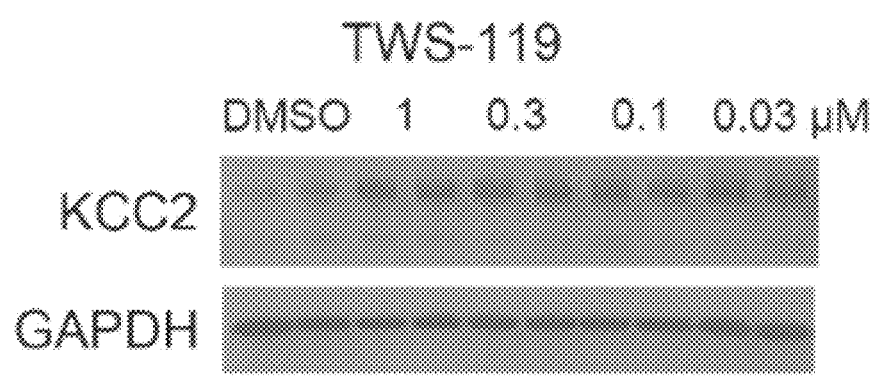
Figure 6D:
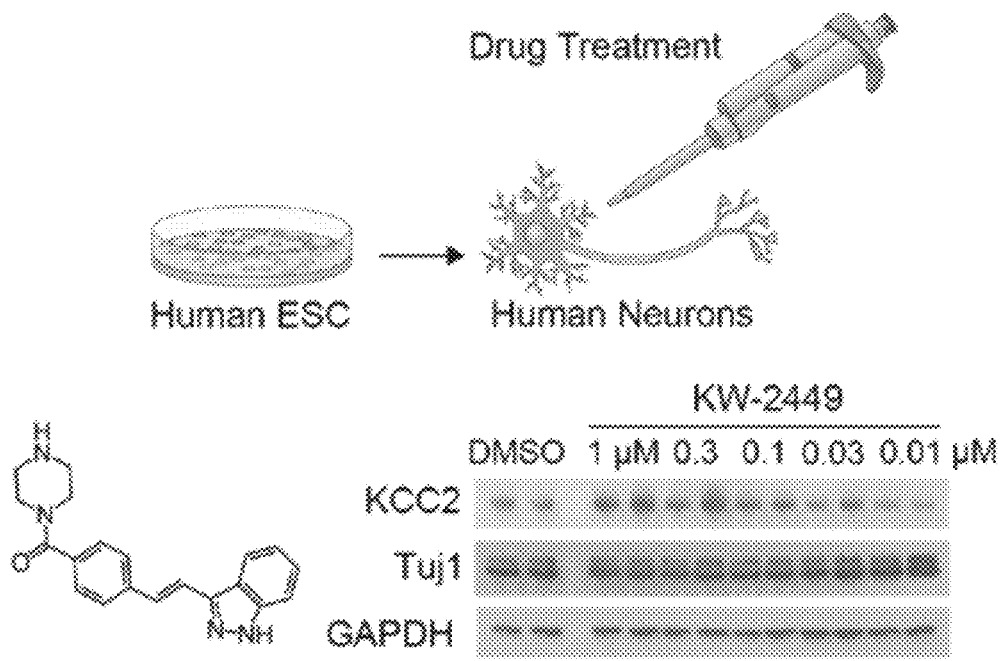
Figure 6E:
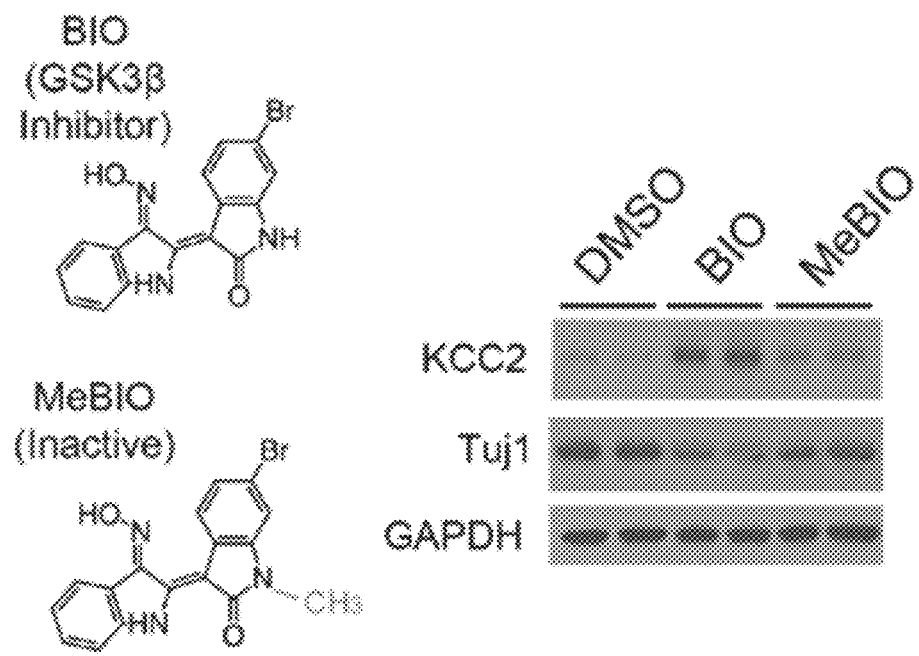
Figure 6F:
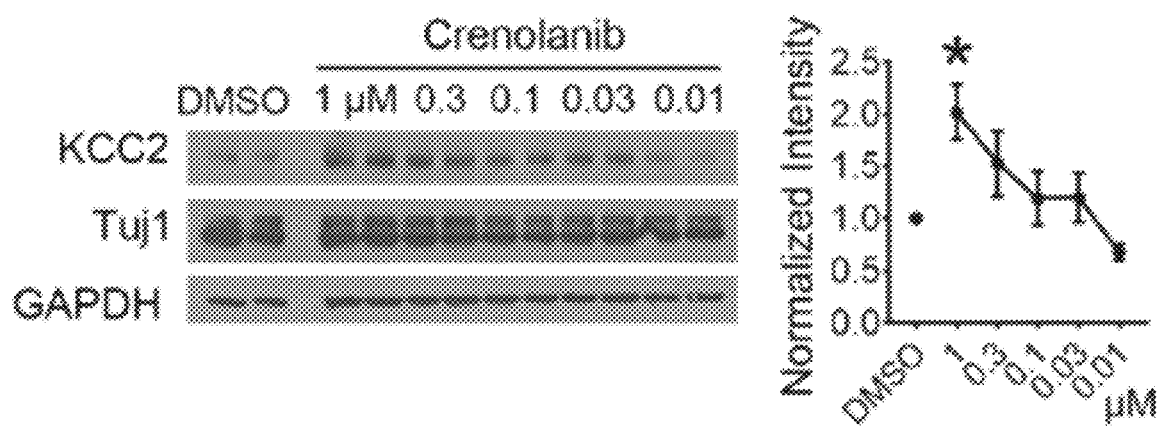
Figure 6G:
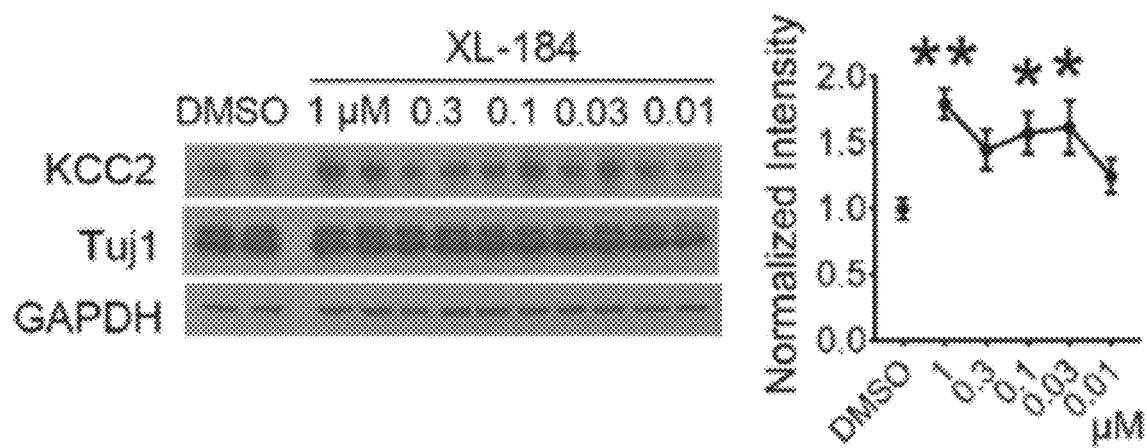
Figure 6H:
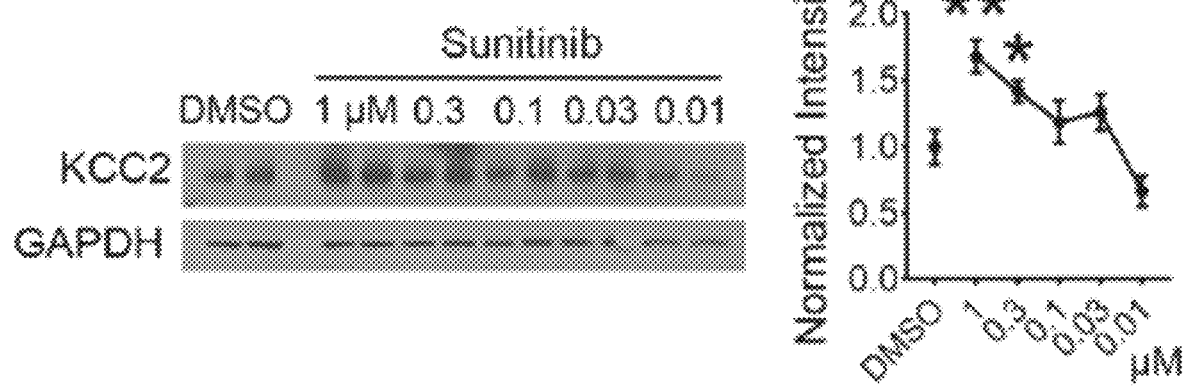
Figure 6I:
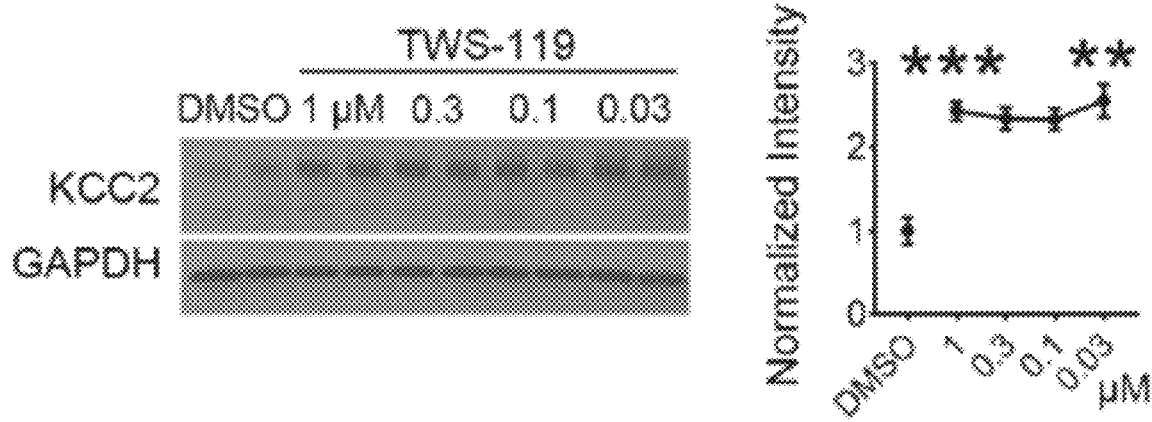

To validate the KEECs, human neurons derived from WT ES cells (WIBR1 male ES cell line) were treated with KEECs, and conducted Western blot experiments were conducted to measure changes in KCC2 expression. Treatment of cultured WT human neurons with KW-2449, a potent inhibitor of fms-like tyrosine kinase-3 (FLT3) (41), induced a significant increase in KCC2 expression in a dose-dependent manner (FIG. 6D; see also FIG. 4A). BIO, an inhibitor of the glycogen synthase kinase 3 β (GSK3β) pathway (42), significantly increased KCC2 expression, while the inactive analog compound MeBIO failed to activate KCC2 expression (FIG. 6E). To elucidate the molecular mechanisms through which hit KEECs regulate KCC2 expression, additional chemical compounds that are structurally different, but functionally analogous to the primary hit compounds KW-2449 and BIO were tested. The results demonstrated significant enhancement of KCC2 expression in human neurons treated with a number of structurally diverse FLT3 kinase inhibitors including Crenolanib, XL-184, and Sunitinib (FIGS. 6F to 6H; see also FIGS. 4D, 4C, and 4B). TWS-119 is a GSK3β inhibitor that is structurally unrelated to the primary hit compound BIO. The results show that treatment of WT neurons with TWS-119 robustly increased KCC2 expression by more than two-fold even at the relatively low concentration of 0.03 µM (FIG. 6I; see also FIG. 4E).

Figure 5A:
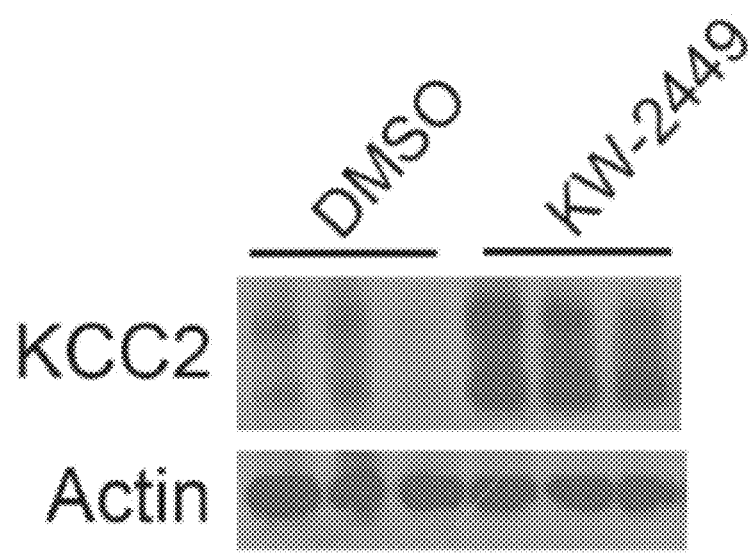
FIGS. 5A to 5C show the treatment of identified KEECs to the organotypical brain slices prepared from WT mice increase KCC2 expression.
Figure 8A:
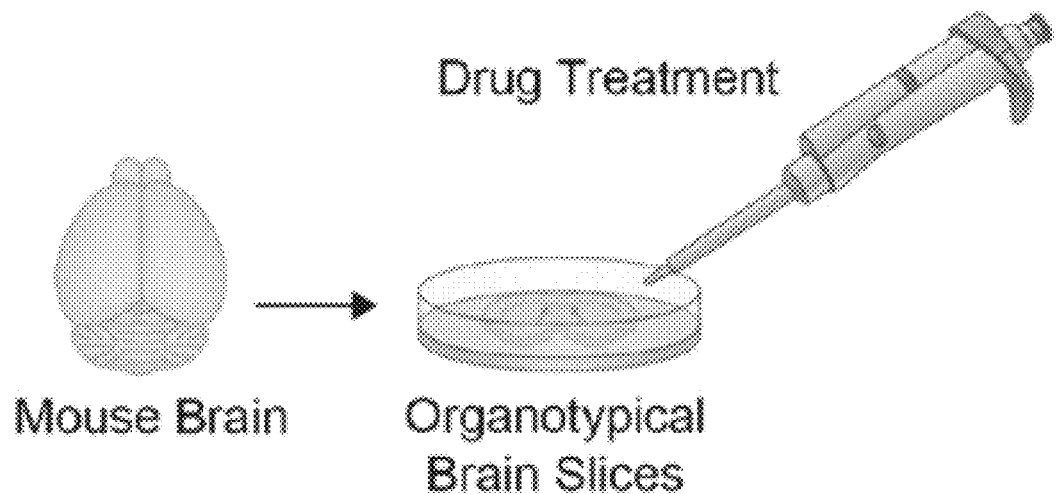
FIGS. 8A to 8H show that KEECs enhance KCC2 protein and mRNA expression levels in cultured organotypic mouse brain slices, and render a hyperpolarizing $E_{GABA}$ shift in cultured neurons.
Figure 8B:
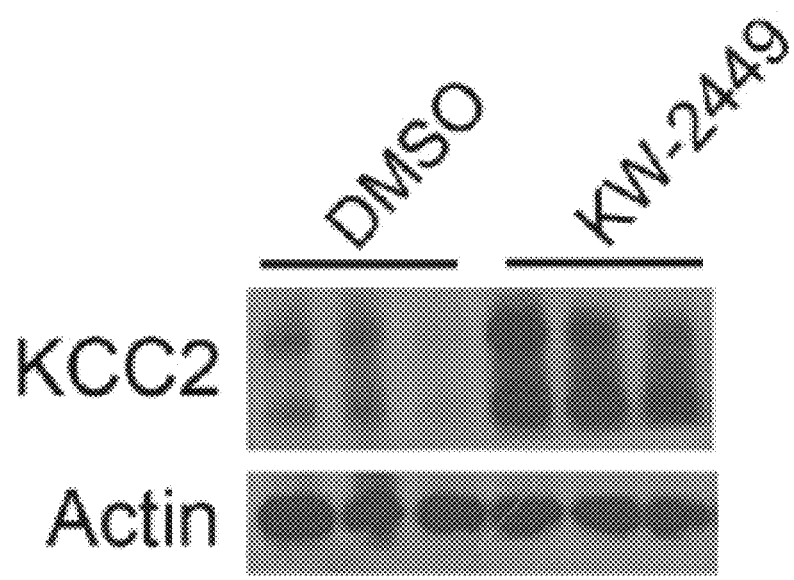
Figure 8C:
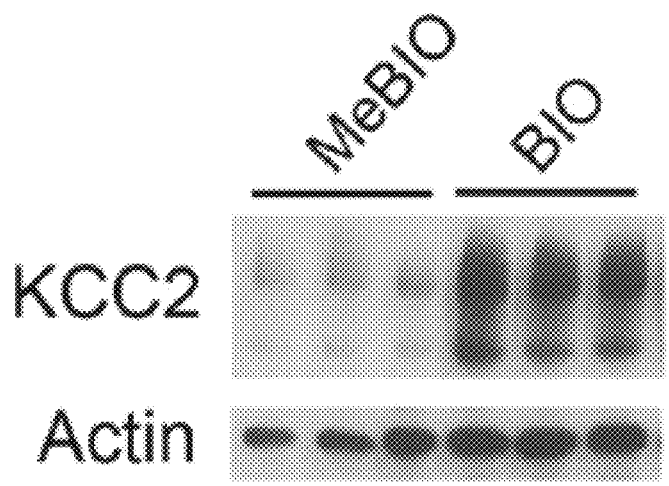

Example 2: KEECs Increase KCC2 mRNA and Protein Expression in Organotypic Brain Slices and Induce Hyperpolarizing Shift in $E_{GABA}$ in Immature Neurons The organotypic mouse brain slice preserves the cellular architecture and cell-cell contact environment of the brain and, accordingly, is considered a suitable model system to investigate drug-induced changes in brain-specific gene expression (43). Organotypic brain slices were treated with identified KEECs and analyzed KCC2 protein level by Western blot analysis (FIG. 8A). Treatment of mouse brain slices with the FLT3 kinase inhibitor KW-2449 (FIG. 8B) or the GSK3β inhibitor BIO (FIG. 8C) enhanced KCC2 expression levels, as compared to a DMSO-treated control and an inactive analog of BIO (MeBIO), respectively. See also FIGS. 5A and 5C.

Figure 5B:
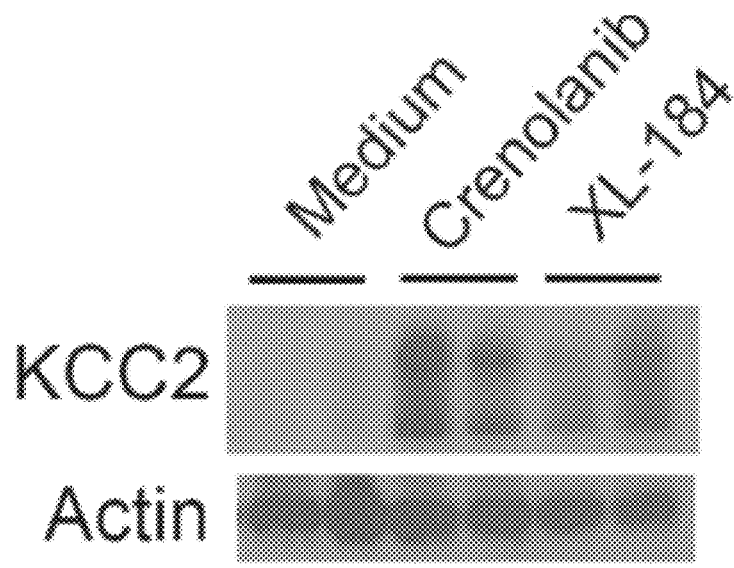
Figure 5C:
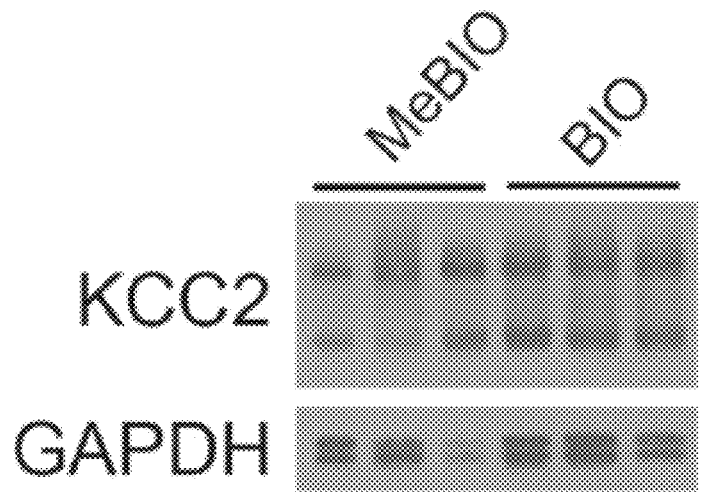
Figure 8D:
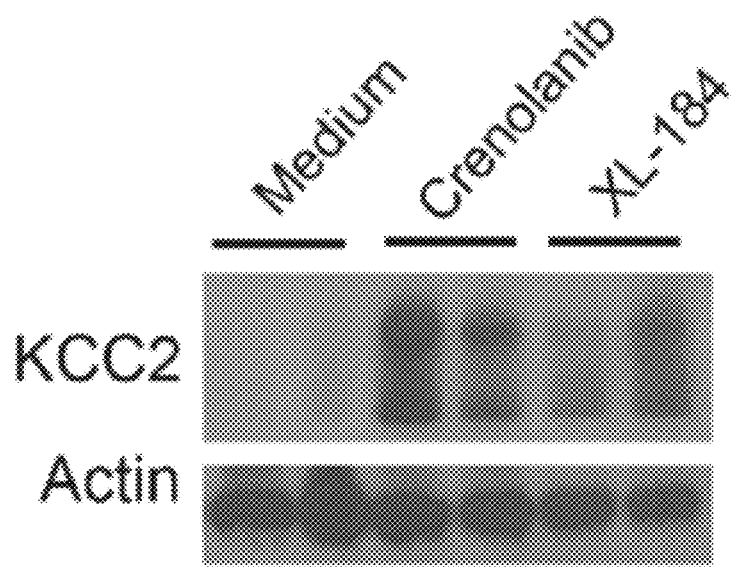
Figure 8E:
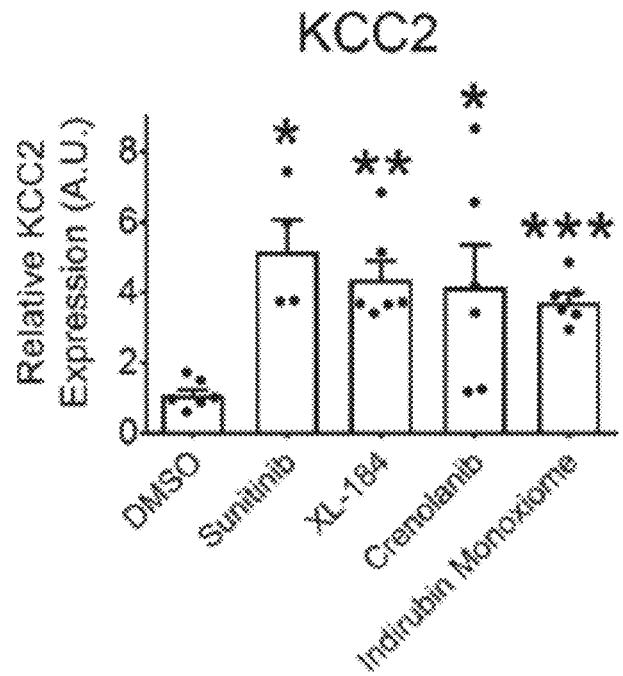
Figure 8F:
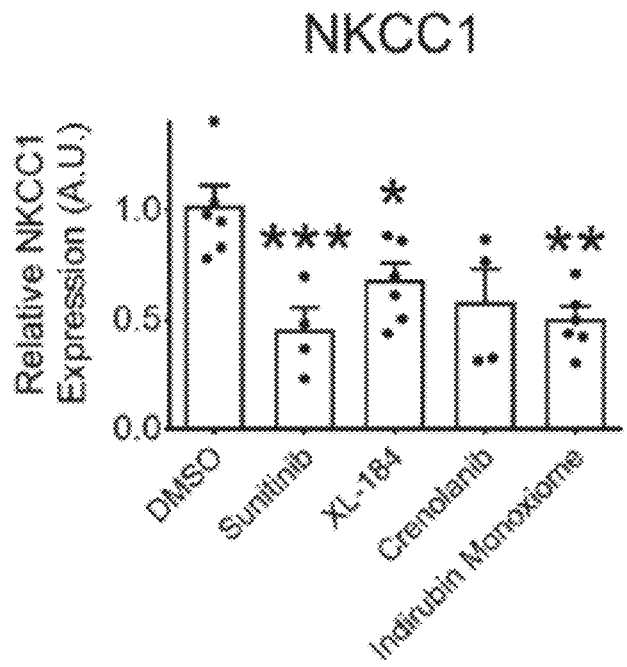

Brain slices were also treated with the FLT3 inhibitors Crenolanib and XL-184. Both compounds significantly increased the KCC2 protein level as compared to culture medium-only control slices (FIG. 8D; see also FIG. 5B). To assess whether increased KCC2 protein levels were due to increased gene transcription or enhanced protein stability, quantitative RT-PCR experiments were performed to measure the KCC2 mRNA level in KEEC-treated brain slices. As shown in FIG. 8E, treatment of the brain slices with the FLT3 inhibitors Sunitinib, XL-184, Crenolanib, or GSK3β inhibitor indirubin monoxiome significantly increased KCC2 expression. In contrast, the expression of NKCC1, a chloride transporter that antagonizes KCC2 activity by shuttling Cl⁻ into the cell (44), was decreased by treatment with KEEC compounds (FIG. 8F).

Figure 8G:
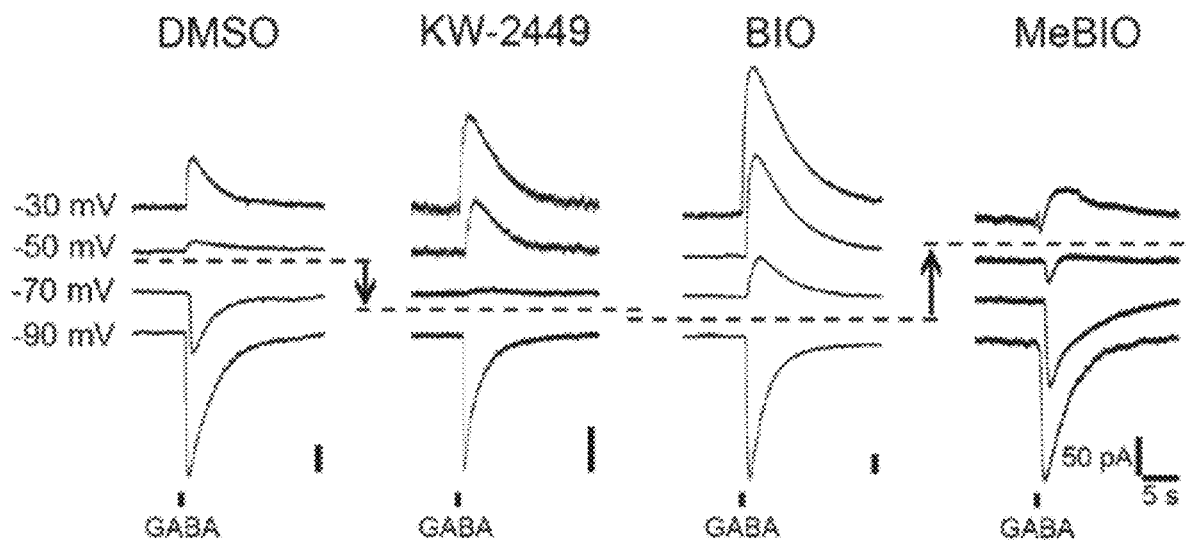
Figure 8H:
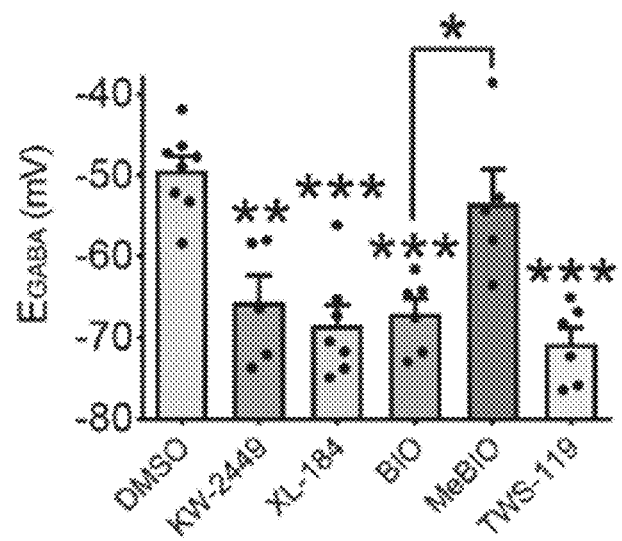
Figure 9A:
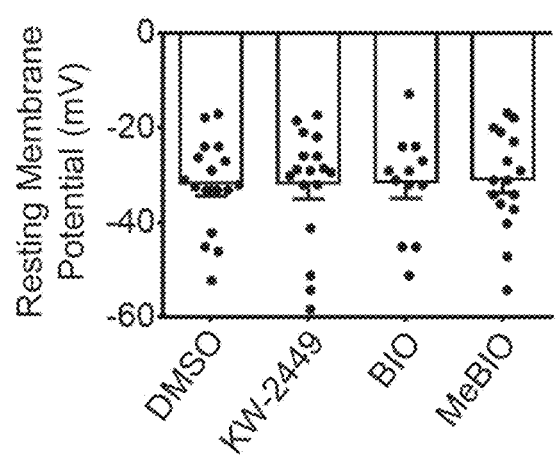
FIG. 9 shows that treatment of DIV6 immature mouse neurons with KW-2449 or BIO does not significantly alter the resting membrane potential (panel A, $p>0.5$, determined by one-way ANOVA). On the contrary, KW-2449 treatment significantly increase the membrane capacitance of mouse neurons comparing to DMSO control (panel B, $p<0.05$, determined by one-way ANOVA).
Figure 9B:
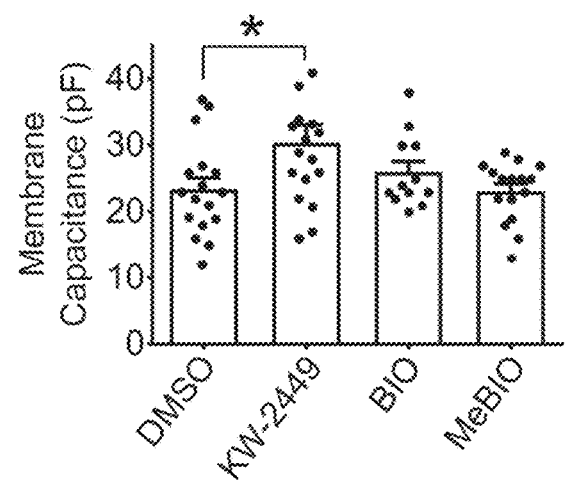

Since treatment with KEECs induces a notable increase in the ratio of KCC2/NKCC1 levels in organotypic brain slices, we investigated whether treatment with KEECs would result in a hyperpolarizing shift in the GABA reversal potential ($E_{GABA}$), an indicator of the efficacy of GABAergic inhibition in neurons (45). Previous work reports that mouse neurons cultured for 6-7 days in vitro (DIV6-7) have not undergone the GABA functional switch; thus, $E_{GABA}$ remains at the depolarized level of about −50 mV (46). $E_{GABA}$ from DIV6-7 immature mouse neurons treated with KEECs or controls were recorded. The results show that treatment with KEECs KW-2449, XL-184, TWS-119, or BIO, but not the DMSO vehicle nor the inactive compound MeBIO, induce a significant hyperpolarizing shift in the $E_{GABA}$ in the immature mouse neurons to levels of about −70 mV (FIGS. 8G, 8H). Meanwhile, the resting membrane potential levels, which are mainly set by K⁺ conductances, were not changed by KEEC treatment in immature neurons (FIG. 9A), suggesting, without wishing to be bound by any theory, that the hyperpolarizing shifts in the $E_{GABA}$ are likely a result of the reductions in neuronal [Cl⁻] and enhanced efficacy of GABAergic inhibition.

Example 3: Further Screens Identify Additional KEECs

Figure 10A:
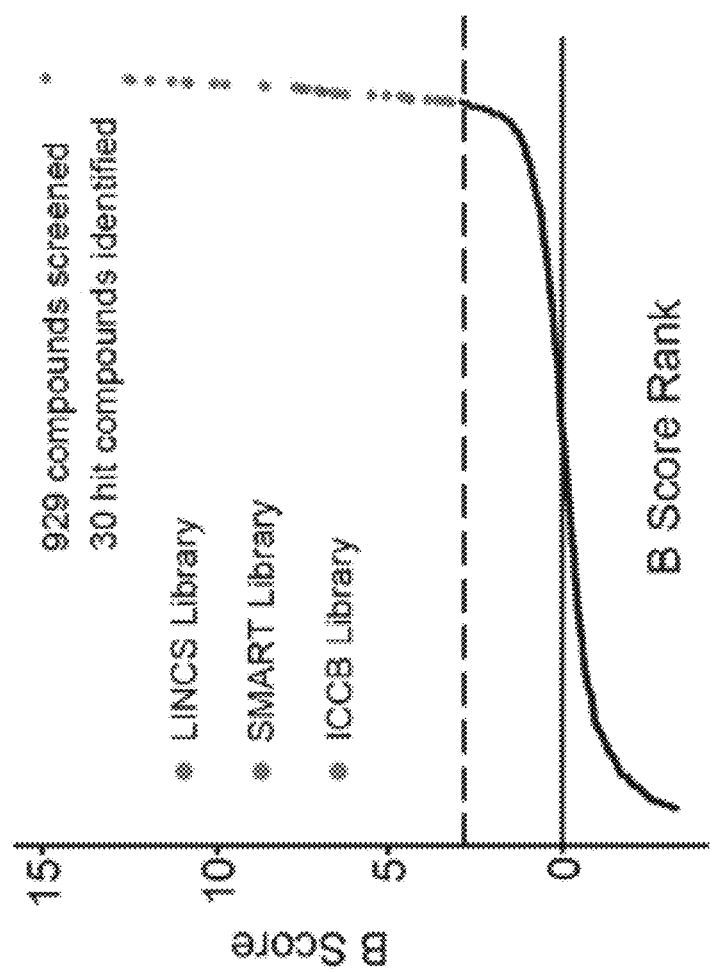
FIGS. 10A to 10K show identification of KEECs that increase KCC2 expression in human RTT neurons.
Figure 10B:
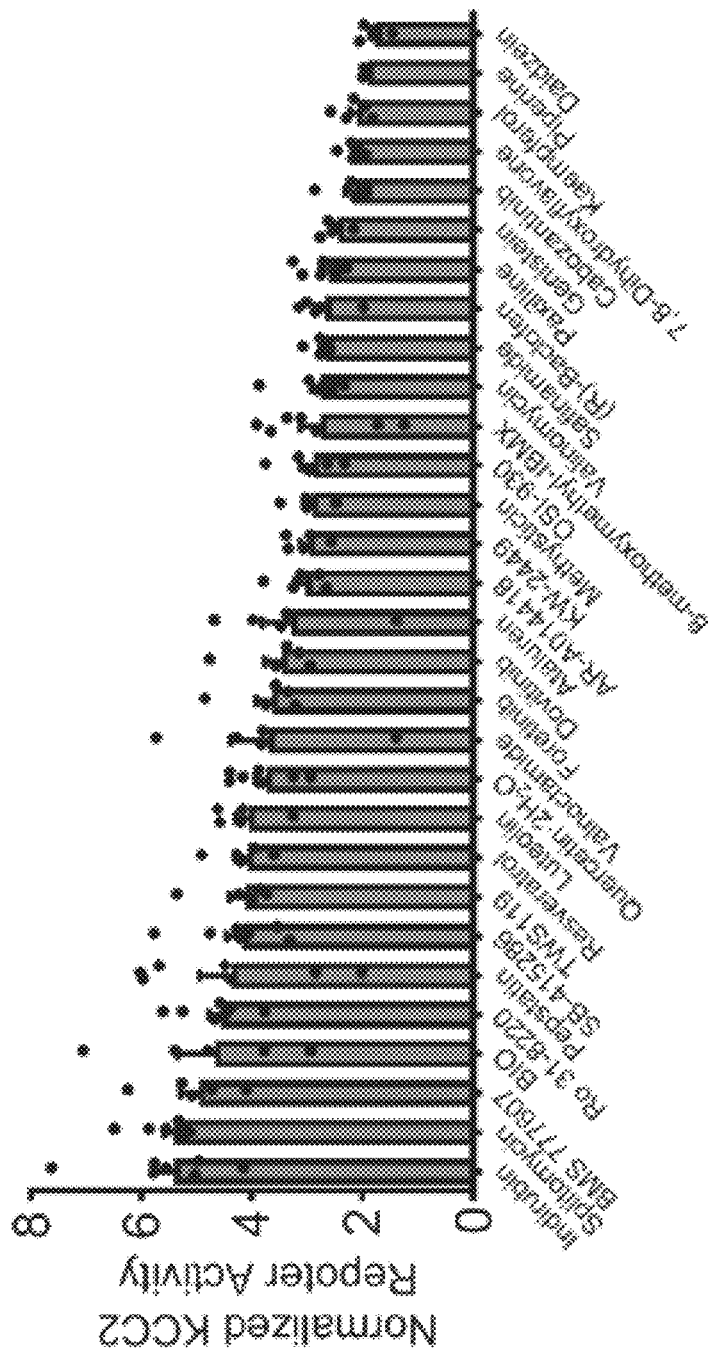

Additional screens for reporter activation in the MECP2-null RTT human KCC2 reporter neurons (isogenic to the WT reporter cells used above) were performed with the LINCS and SMART libraries as well as the ICCB known bioactive library and identified hits as compounds with B score >3. Most KEECs that enhanced KCC2 expression in WT neurons, including KW-2449, BIO, Resveratrol, also induced a significant increase of KCC2 reporter activity in RTT neurons, as described in Example 1 (FIGS. 10A and 10B). A list of the top 30 hits identified in these additional rounds of screens with RTT KCC2 reporter neurons is given in Table 3.

TABLE 3

List of hit compounds identified from expanded compound screening with RTT KCC2 reporter neurons (and certain analogs)

| Name | IUPAC Name | B Score | Class/ Cellular Effect | Major targets |
|---|---|---|---|---|
| (R)-Baclofen | Benzenepropanoic acid | 6.65 | GAB A$_B$ agonist | GAB A$_B$ receptor |
| 7,8-Dihydroxy-flavone | 7,8-Dihydroxyflavone | 4.01 | TrkB agonist | TrkB |
| 8-methoxymethyl-IBMX | 8-(Methoxymethyl)-1-methyl-3-(2-methylpropyl)-7H-purine-2,6-dione | 4.8 | Phosphodiesterase inhibitor | PDE1 |
| AR-AO14418 | N-(4-Methoxybenzyl)-N'-(5-nitro-1,3-thiazol-2-yl)urea | 8.69 | GSK3 inhibitor | GSK3 |
| Ataluren | 3-[5-(2-Fluorophenyl)-1,2,4-oxadiazol-3-yl]benzoic acid | 7.43 | nonsense-suppressing agent | CTFR mutation causal for CF |
| BIO | (2'Z,3'E)-6-Bromoindirubin-3'-oxime | 3.42 | GSK-3α/β inhibitor | GSK3α/β |
| BMS 777607 | N-(4-(2-amino-3-chloropyridin-4-yloxy)-3-fluorophenyl)-4-ethoxy-1-(4-fluorophenyl)-2-oxo-1,2-dihydropyridine-3-carboxamide | 11.97 | Met-related protein kinase inhibitor | e-Met, Axl, Ron, Tyro3 |
| XL-184 (Cabozantinib) | N-(4-(6,7-dimethoxyquinolin-4-yloxy)phenyl)-N-(4-fluorophenyl)cyclopropane-1,1-dicarboxamide | 3.25 | Kinase inhibitor | FLT3, MET, VEGFR, RET, GAS6 receptor (AXL), KIT |
| Daidzein | 7-hydroxy-3-(4-hydroxyphenyl)-4H-chromen-4-one | 4.64 | Antioxidant | GPER |
| Dovitinib | 1-amino-5-fluoro-3-(6-(4-methylpiperazin-1-yl)-1H-benzo[d]imidazol-2-yl)quinolin-2(1H)-one | 4.44 | Multi-target RTK inhibitor | FLT3/c-Kit, FGFR1/3, VEGFR1-4 |
| Foretinib | N1'-[3-fluoro-4-[[6-methoxy-7-(3-morpholinopropoxy)-4-quinolyl]oxy]phenyl]-N1-(4-fluorophenyl)cyclopropane-1,1-dicarboxamide | 4.05 | Kinase inhibitor | c-Met, VEGFR-2; FLT3 is also a target |
| Genistein | 4',5,7-Trihydroxyisoflavone | 5.11 | Nrf2 + PPAR activator, EGFR inhibitor | ERβ, GPER, PPARs, tyrosine kinases, |

TABLE 3-continued

List of hit compounds identified from expanded compound screening with RTT KCC2 reporter neurons (and certain analogs)

| Name | IUPAC Name | B Score | Class/ Cellular Effect | Major targets |
|---|---|---|---|---|
| Indirubin | (3Z)-3-(3-Oxo-1,3-dihydro-2H-indol-2-ylidene)-1,3-dihydro-2H-indol-2-one | 3.73 | Kinase inhibitor | topoisomerase, AAADs GSK3 PLK1, PIN1, CDC25B |
| Kaempferol | 3,5,7-Trihydroxy-2-(4-hydroxyphenyl)-4H-chromen-4-one | 3.92 | SIRTI activator, Antidepressant | Sirtuin1, MAO, PGC-1α, ERRα/β |
| KW-2449 | (E)-(4-(2-(lH-indazol-3-yl) vinyl)phenyl)(piperazin-1-yl)methanone | 5.45 | Kinase inhibitor | FLT3, ABL, ABL-T315I, Aurora kinase |
| Luteolin | 2-(3,4-Dihydroxyphenyl)-5,7-dihydroxy-4-chromenone | 11.34 | Mono amine transporter activator | NFκB |
| Methysticin | (2R)-2-[(E)-2-(1,3-Benzodioxol-5-yl)ethenyl]-4-methoxy-2,3-dihydropyran-6-one | 7.17 | Neuroprotective, MAOI, NRI | CYP1A1 |
| OSI-930 | 3-[(4- quinolinylmethyl)amino]-N-[4- (trifluoromethoxy)phenyl] -2-thiophenecarboxamide | 5.55 | Kinase inhibitor | Kit, KDR, CSF-1R, Flt-1, c-Raf Lek. PDGFRα/β, Flt-3, Abl |
| Paxilline | (2R,4bS,6aS,12bS,12cR,14aS)-4b-hydroxy-2-(1-hydroxy-1-methylethyl)-12b,12c-dimethyl-5,6,6a,7,12,12b,12c,13,14,14a-decahydro-2H-chromeno[5',6':6,7]indeno[1,2-b]indol-3(4bH)-one | 4.1 | Potassium channel blocker | Potassium channels |
| Pepstatin | Isovalery-Val-Val-Sta-Ala-Sta [Sta = statine = (3S,4S)-4-amino-3-hydroxy-6-methylheptanoic acid] | 8.64 | Aspartyl peptidases | Acidic proteases e.g. pepsin, renin, cathepsin D, bovine chymosin, protease B |
| Piperine | (2E,4E)-5-(Benzo[d][1,3]dioxol-5-yl)-1-(piperidin-1-yl)penta-2,4-dien-1-one | 4.69 | TRPV1 activator, tyrosine protein kinases inhibitor | TRPV1, TRPA1, P-Gylco-protein, CYP450, CYP3A4 |
| Quercetin-2H$_2$O | 2-(3,4-dihydroxyphenyl)-3,5,7-trihydroxy-4H-chromen-4-one | 7.76 | Polar auxin transport inhibitor, phosphodi-esterase inhibitor | ER a/b, GPER, PI3-kinase, mitochondria 1 ATPase |
| Resveratrol | 3,5,4'-trihydroxy-trans-stilbene | 12.65 | MAOI, Antioxidant | Sirtuin1, PGC-1α |
| Ro 31-8220 | 2-{1-[3-(Amidinothio)propyl]-1H-indol-3-yl}-3-(1-methylindol-3-yl)maleimide methanesulfonate salt | 10.11 | Kinase inhibitor | GRK-5, PKC, MAPKAP kinase |
| Safinamide | (2S)-2-[[4-[(3-fluorophenyl)methoxy]phenyl]methylamino] propanamide | 4.82 | MAO inhibitor | MAO, σ receptor |
| SB-415286 | 3-[(3-Chloro-4-hydroxyphenyl)-amino]-4-(2-nitrophenyl)-1H-pyrrol-2,5-dione | 5.58 | GSK-3 inhibitor | GSK-3 |
| Splitomycin | 1,2-Dihydro-3H-naphtho[2,1-b]pyran-3-one | 9.79 | N.A | Sir2p, HDAC, SIRT1 |

TABLE 3-continued

List of hit compounds identified from expanded compound screening with RTT KCC2 reporter neurons (and certain analogs)

| Name | IUPAC Name | B Score | Class/ Cellular Effect | Major targets |
|---|---|---|---|---|
| TWS119 | 3-[6-(3-Amino-phenyl)-7H-pyrrolo[2,3,-d]pyrimidin-4-yloxy]-phenol | 3.64 | GSK-3β inhibitor | GSK-3β |
| Valinomycin | Cyclo-(L-Val-D-HyIva-D-Val-L-Lac-)3 [Hylva = a-Hydroxy isovaleric acid, lac = Lactic acid] | 4.49 | Cyclo-dodeca-depsipeptide ionophore 1 antibiotic | Biological, artificial lipid membranes |
| Valnoctamide | 2-ethyl-3-methyl-pentanamide | 14.99 | Anti-convulsan, indirect GABA agonist | GABA trans-amination |
| Crenolanib | 1-(2-{5-[(3-Methyloxetan-3-yl)methoxy ]-1H-benzimidazol-1-yl}quinolin-8-yl)piperidin-4-amine | N/A | Kinase inhibitor | FLT3, PDGFRα/β |
| Sunitinib | N-[2-(Diethylamino)ethyl]-5-[(Z)-(5-fluor-1,2-dihydro-2-oxo-3H-indol-3-yliden)-methyl]-2,4-dimethyl-1H-pyrrol-3-carboxamid | N/A | RTK inhibitor | PDGFRs, VEGFRs, c-KIT; FLT3 is also a target |
| XL-184 (Cabozantinib) | N-(4-((6,7-Dimethoxyquinolin-4-yl)oxy)phenyl)-N'-(4-fluorophenyl)cyclopropane-1,1-dicarboxamide | N/A | Kinase inhibitor | c-Met, VEGFR2, AXL, RET |
| TWS-119 | 3-[6-(3-Amino-phenyl)-7H-pyrrolo[2,3,-d]pyrimidin-4-yloxy]-phenol | N/A | GSK3 inhibitor | GSK3P |
| Indirubin monoxiome | 3-[1,3-dihydro-3-(hydroxyimino)-2H-indol-2-ylidene]-1,3-dihydro-2H-indol-2-one | N/A | GSK3 inhibitor | GSK3, CDK1/5 |
| FLT inhibitor-1 (Calbiochem 343020) | 2-(3,4-dimethoxybenzamido)-5,6-dihydro-4H-cyclopenta[b]thiophene-3-carboxamide | N/A | FLT3 inhibitor | FLT3 |

Note:
The compounds with the description 'N/A' in the B-score field are analog compounds of primary hit compounds identified from screening.

Figure 10C:
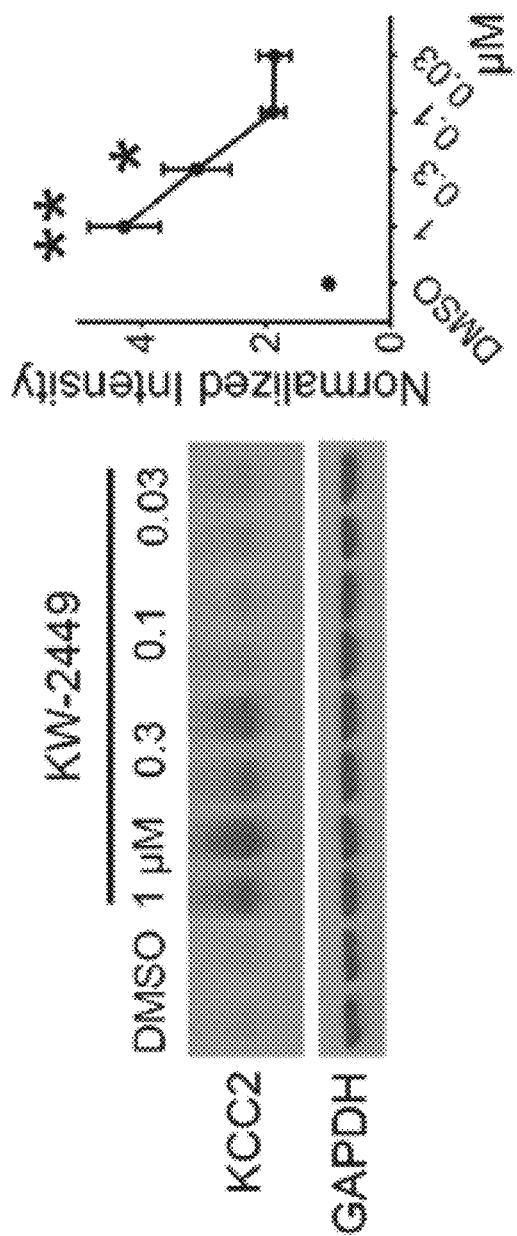
Figure 10D:
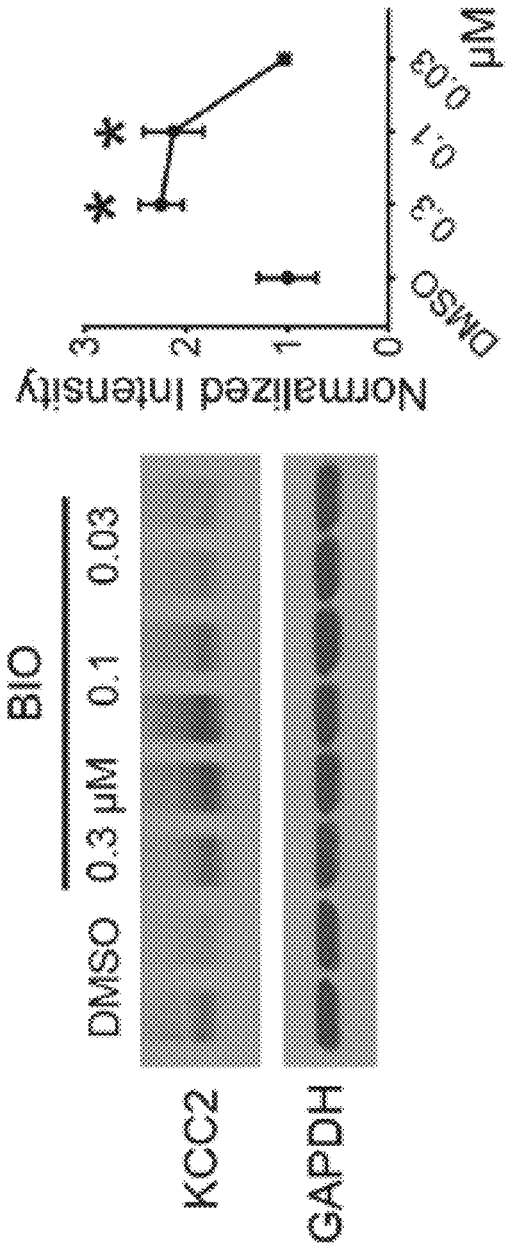
Figure 10E:
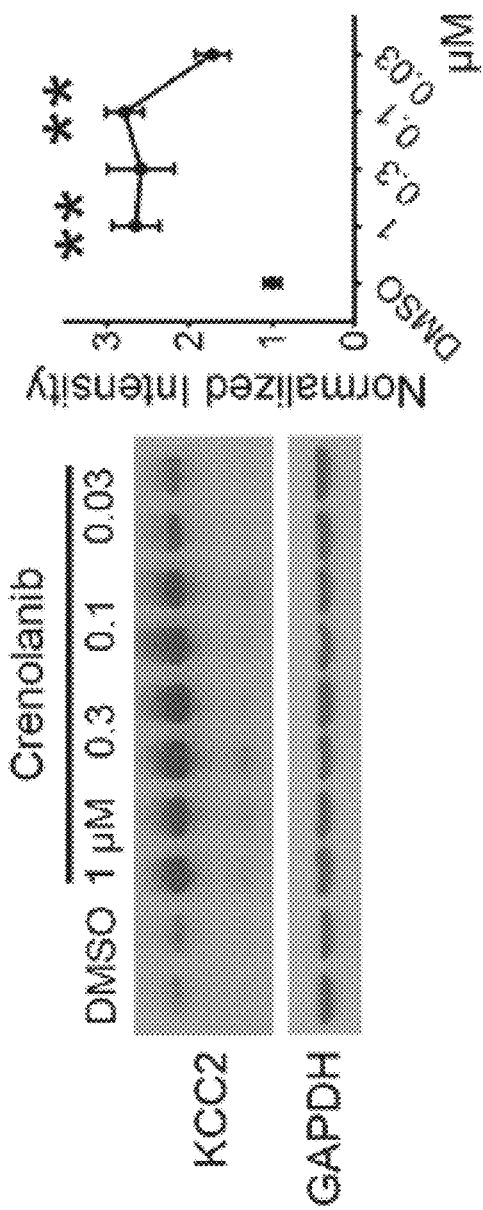
Figure 10F:
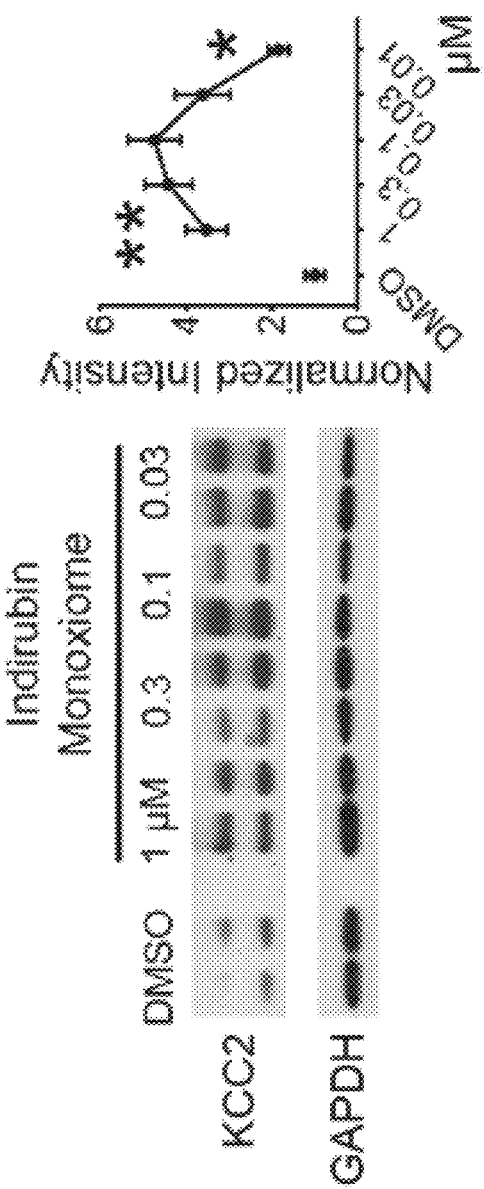
Figure 10G:
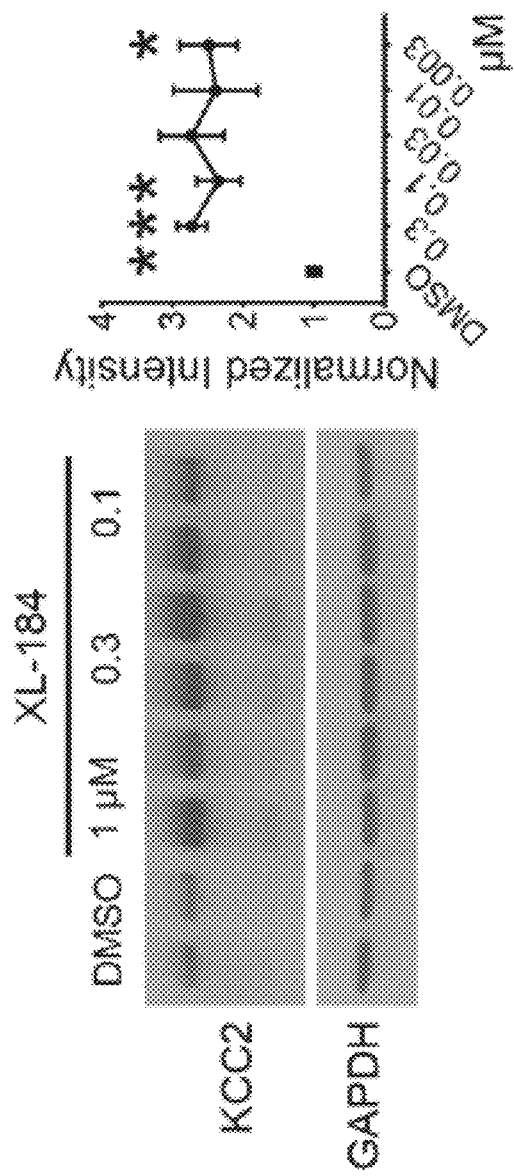
Figure 10H:
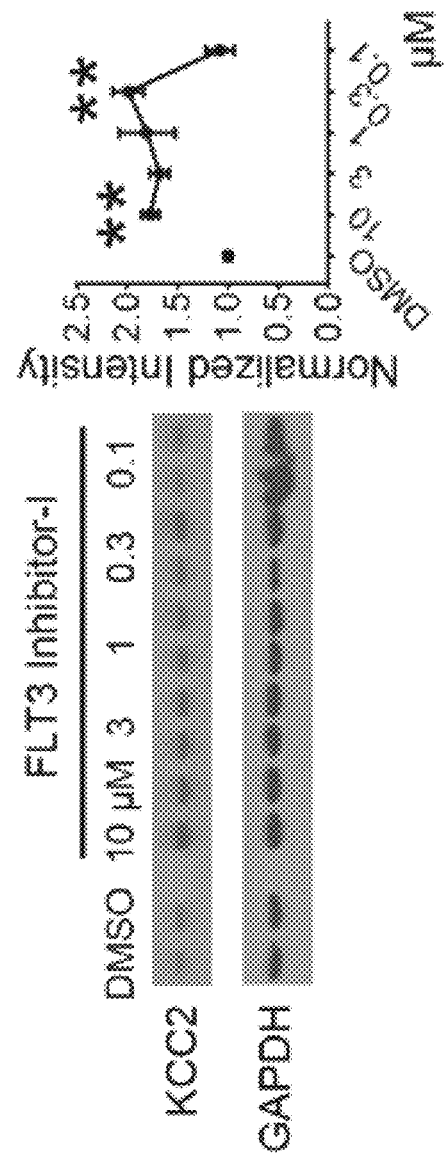

Almost all of the compounds identified in the screens described in Example 1 were also identified as hits in these screens. A number of additional compounds were also identified. As described in Example 1, a significant enhancement of KCC2 expression was detected in human RTT neurons treated with FLT3 kinase inhibitors, including KW-2449 (FIG. 10C), Crenolanib (FIG. 10E; see also FIG. 3A), XL-184 (FIG. 10G; see also FIG. 3B), and FLT3 Inhibitor-1 (FIG. 10H). The GSK3β inhibitor BIO (FIG. 10D), and a structural analog of BIO, indirubin monoxiome (FIG. 10F; see also FIG. 3C), also increased KCC2 expression levels significantly. The increases in KCC2 signal induced by KEECs are higher in RTT neurons than in WT neurons, which is consistent with the previous report that the baseline KCC2 expression level is lower in RTT neurons (7, 48).

Example 4: Further Analysis of KEECs

Figure 11A:
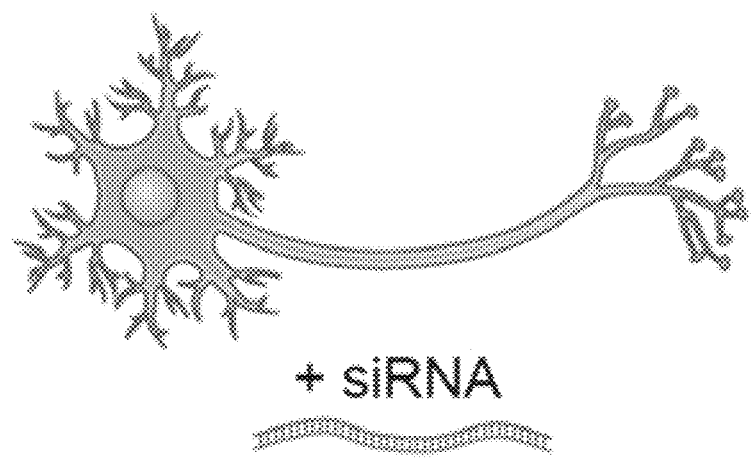
FIGS. 11A to 11F show that knocking-down FLT3 or GSK3β gene with siRNA increase KCC2 expression level in immature mouse neurons or human RTT neurons.
Figure 11B:
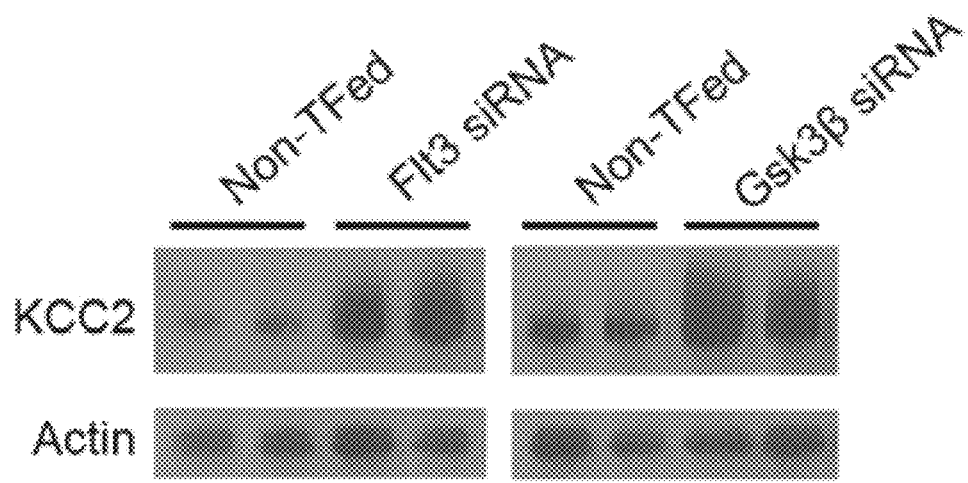
Figure 11C:
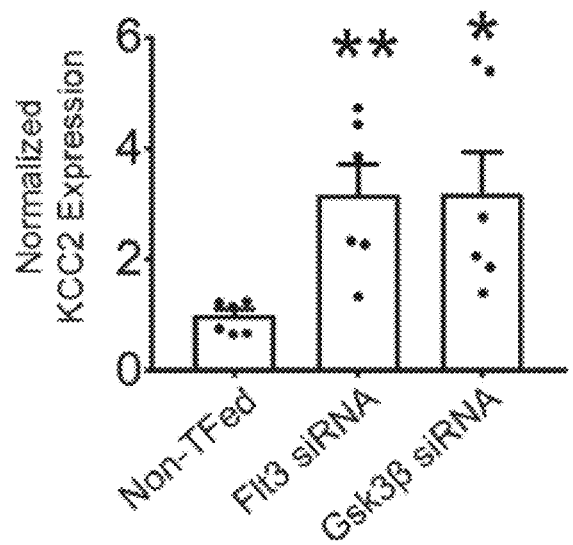
Figure 11D:
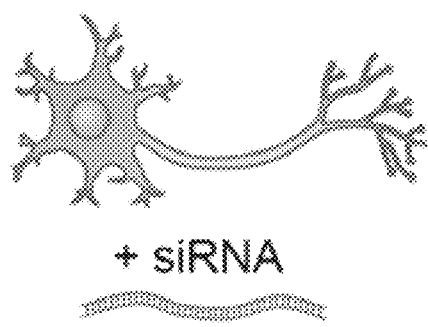
Figure 11E:
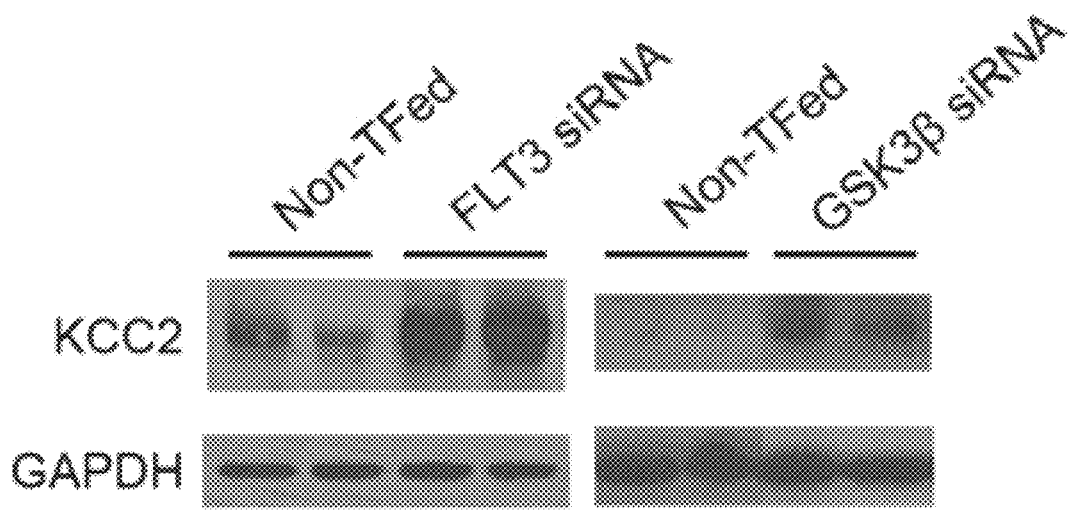
Figure 11F:
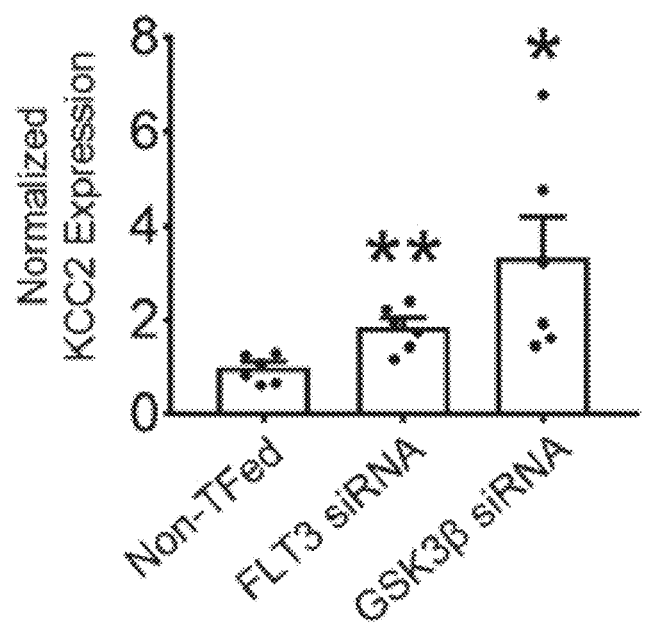

To further corroborate the finding that inhibition of the FLT3 or GSK3β pathways lead to increase in KCC2 expression, we have carried out experiments that utilize small interfering RNA (siRNA) to directly silence the expression of target genes were carried out. Transfection of siRNA against the mouse Flt3 or Gskβ gene into immature mouse neurons significantly increase the KCC2 gene expression (FIGS. 11A to 11C). Similarly, transfection of siRNA against the human FLT3 or GSK3β genes significantly increases the KCC2 gene expression in cultured human RTT neurons (FIGS. 11D to 11F). The results establish the causal relationship between a reduction in the activities of FLT3 or GSK3β signaling pathways and the resulting increase in KCC2 expression.

Figure 3A:
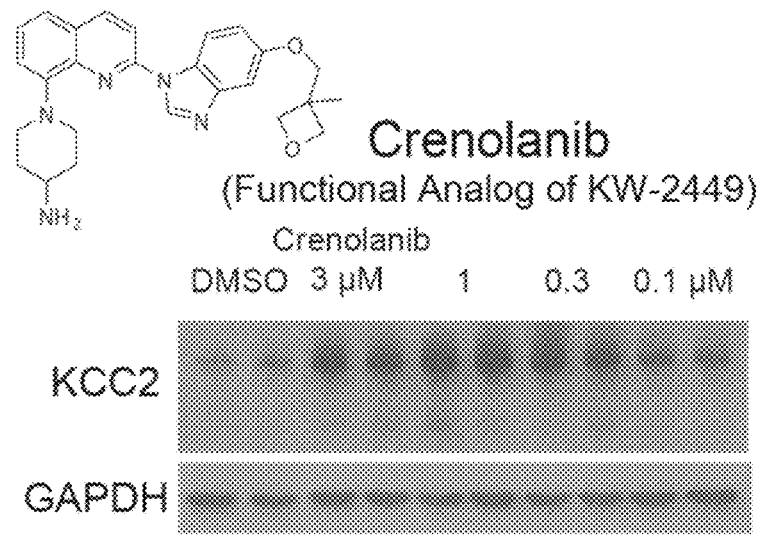
FIGS. 3A to 3F show the use of structural and functional analogs of KW-2449 and KIN 001-043 to elucidate the molecular pathways through which KEECs increase KCC2 expression in cultured RTT human neurons.
Figure 3B:
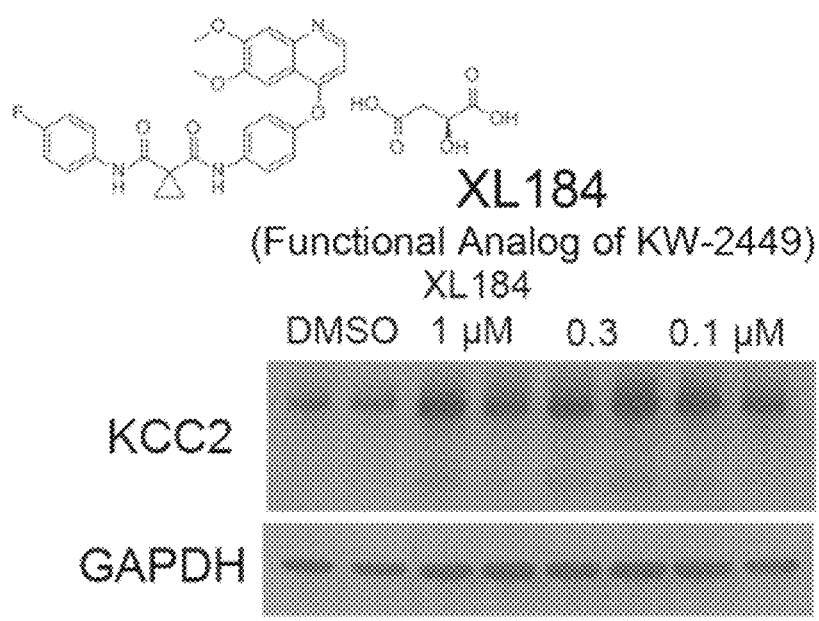
Figure 3C:
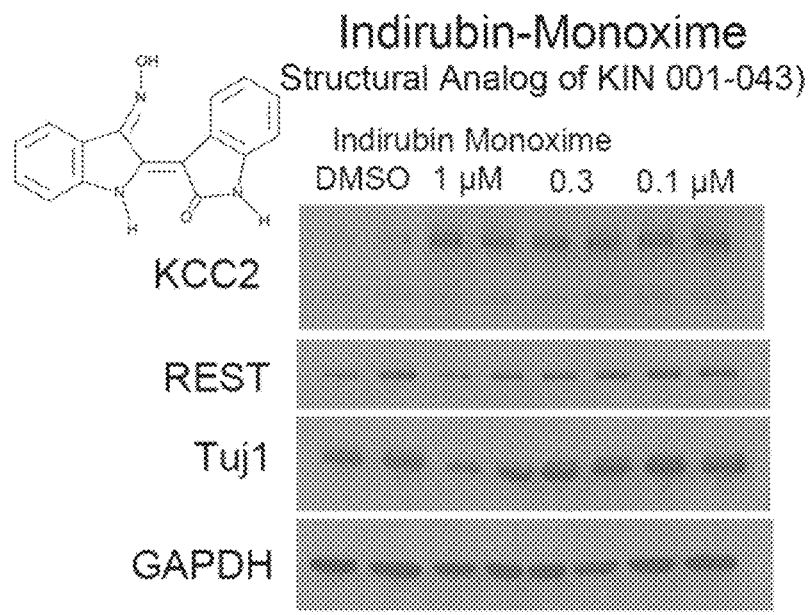
Figure 3D:
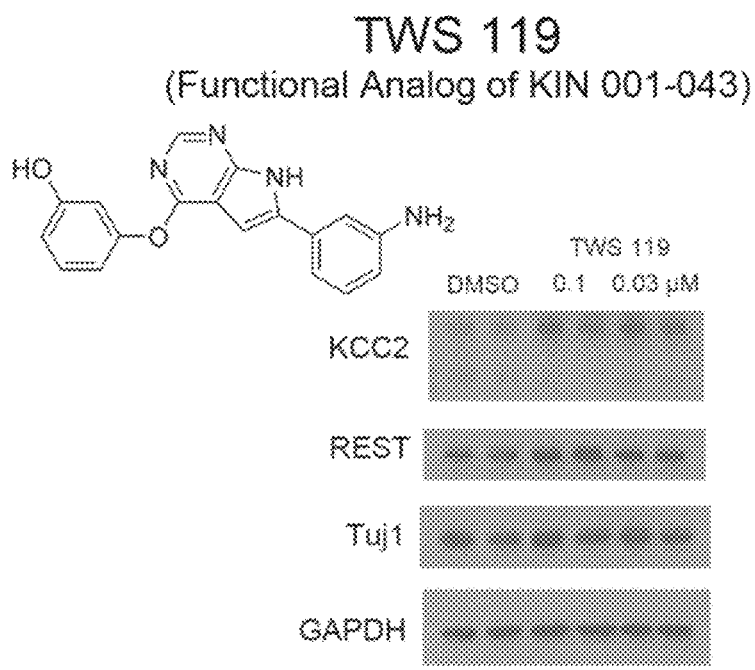
Figure 3E:
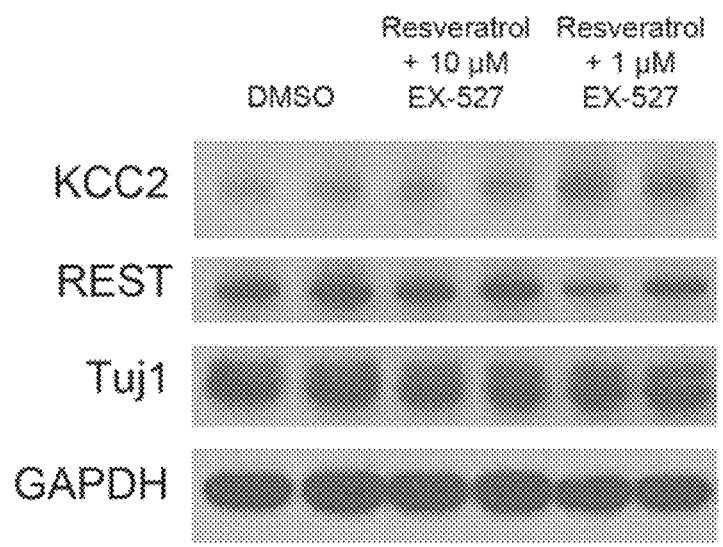
Figure 3F:
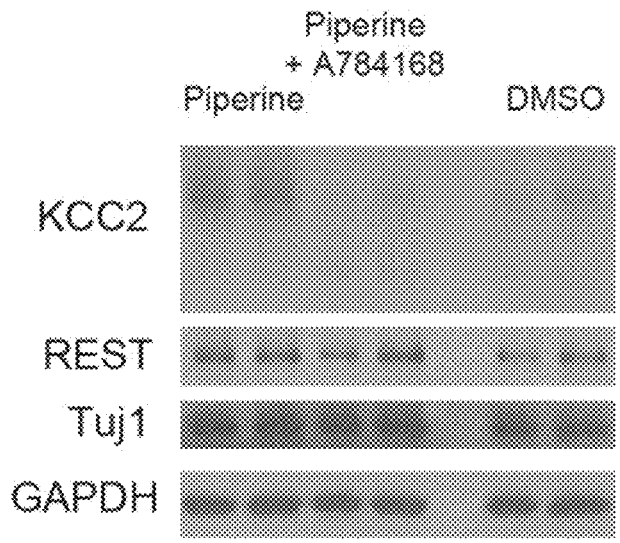
Figure 10I:
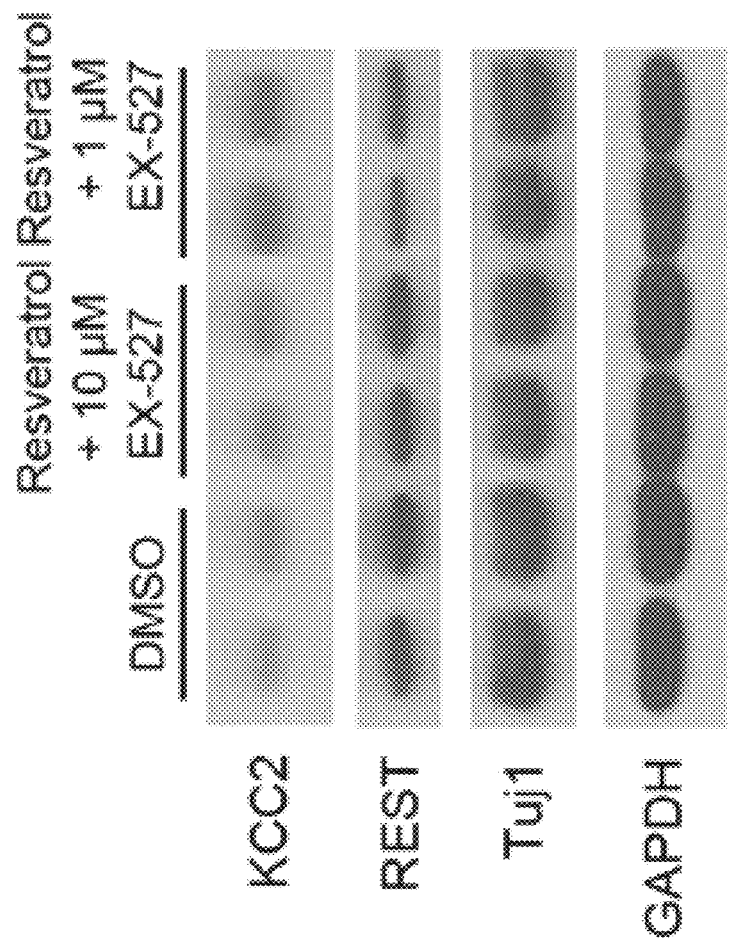
Figure 10J:
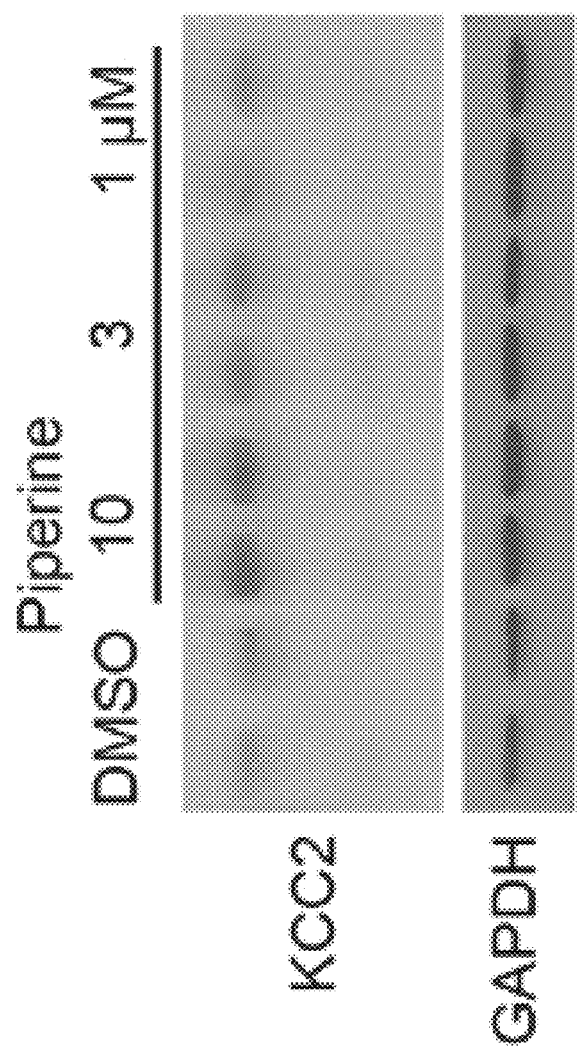
Figure 10K:
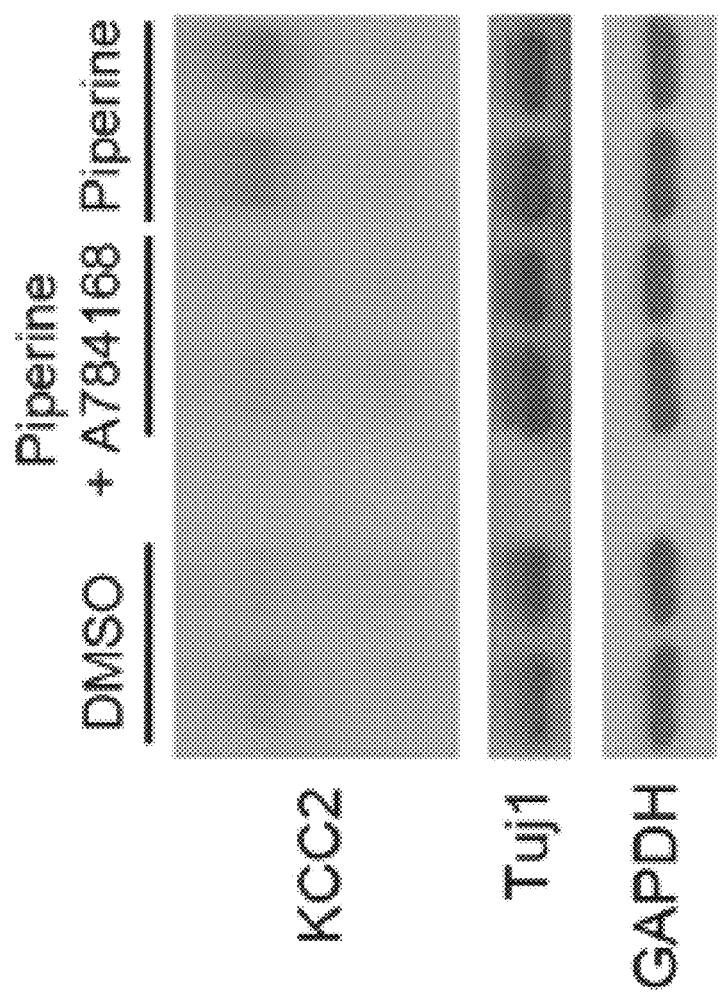

Two hit compounds Resveratrol and Piperine act on different pathways than the kinase inhibitors, activating the Sirtuin 1 (SIRT1) (49) and the transient receptor potential cation channel subfamily V member 1 (TRPV1) (50) signaling pathways, respectively. A study using a glioblastoma cell line has shown that treatments with Resveratrol activate the SIRT1 pathway, which reduces expression of the neuronal gene repressor NRSF/REST (49), an inhibitor of KCC2 expression (51). When Resveratrol was applied to cultured neurons in the presence of a high concentration of SIRT1 pathway blocker EX-527, the expression of neither KCC2 nor REST was changed as compared to the DMSO control (FIG. 10I; see also FIG. 3E). However, when Resveratrol was co-applied with a concentration of EX-527 below the threshold for SIRT1 pathway inhibition, a substantial increase in KCC2 expression and concurrent reduction in the level of REST was observed. Without wishing to be bound by any theory, these results support that SIRT1-mediated reduction in REST level is likely a link between Resveratrol treatment and the resulting increase in KCC2 expression. Treatment with Piperine, an activator of the TRPV1 channel (50), induced a significant increase in KCC2 expression in cultured human neurons (FIG. 10J), whereas blocking the TRPV1 channel with the TRPV1 antagonist A784168 eliminated the KCC2-inducing effect of Piperine (FIG. 10K; see also FIG. 3F). Thus, these data demonstrate that activation of the SIRT1 or TRPV1 pathways enhances KCC2 expression in RTT human neurons.

Figure 12A:
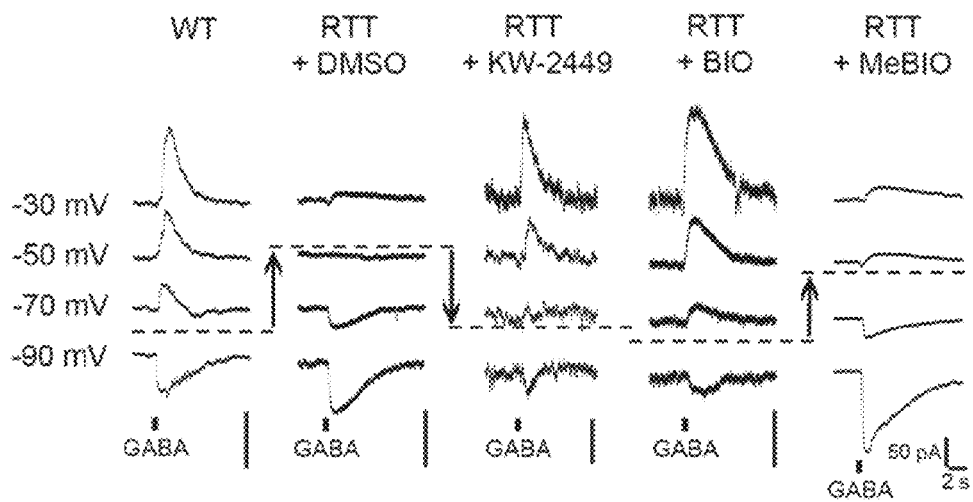
FIGS. 12A to 12H show that treatment of cultured human RTT neurons with KW-2449 or BIO rescue deficits in $E_{GABA}$ and in excitatory neurotransmission to levels comparable to isogenic WT control neurons.
Figure 12B:
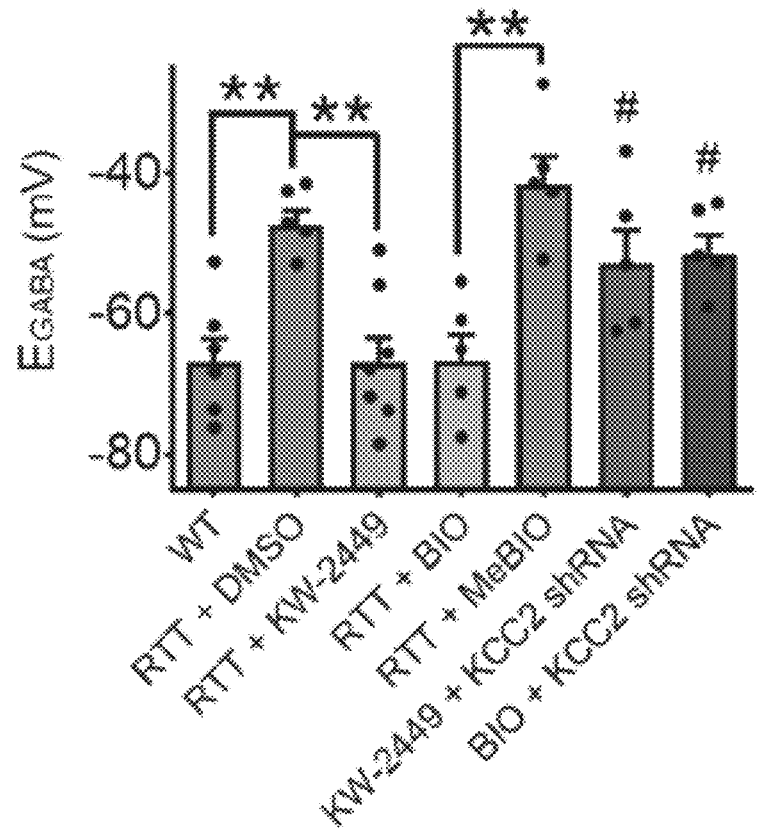
Figure 12C:
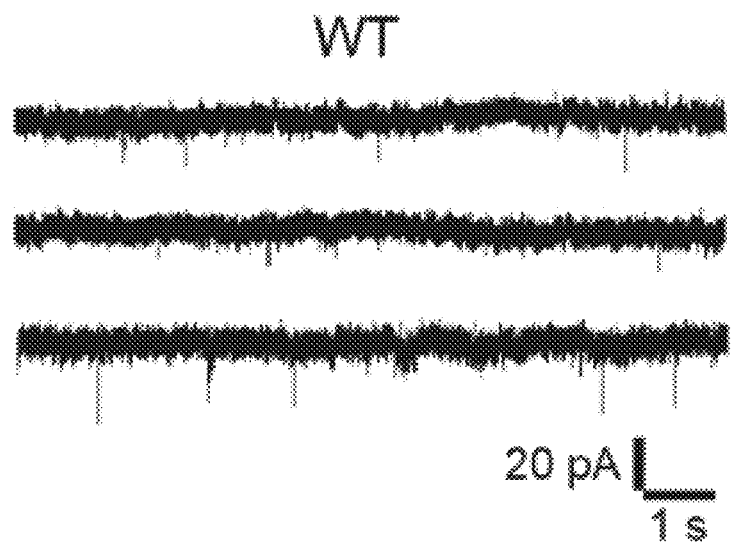
Figure 12D:
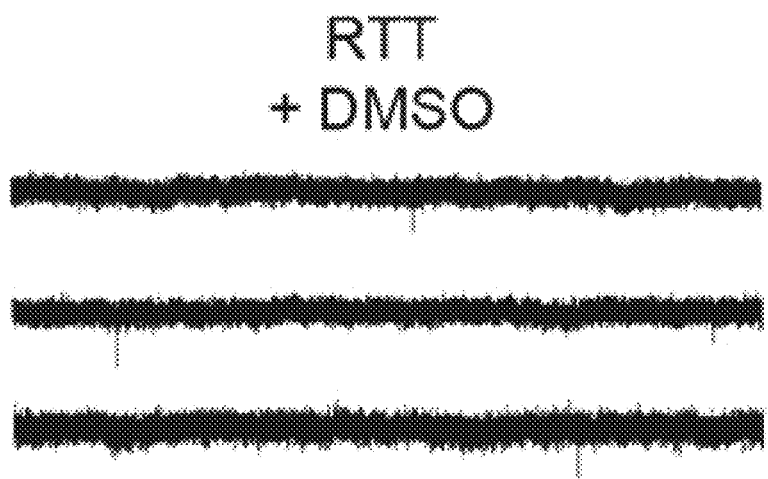
Figure 12E:
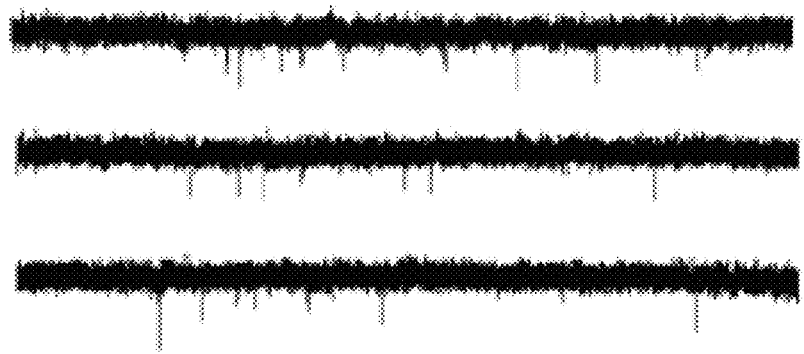
Figure 12F:
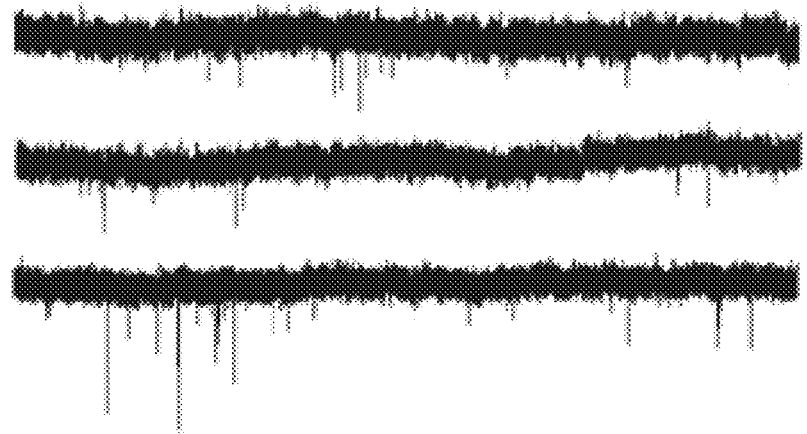
Figure 12G:
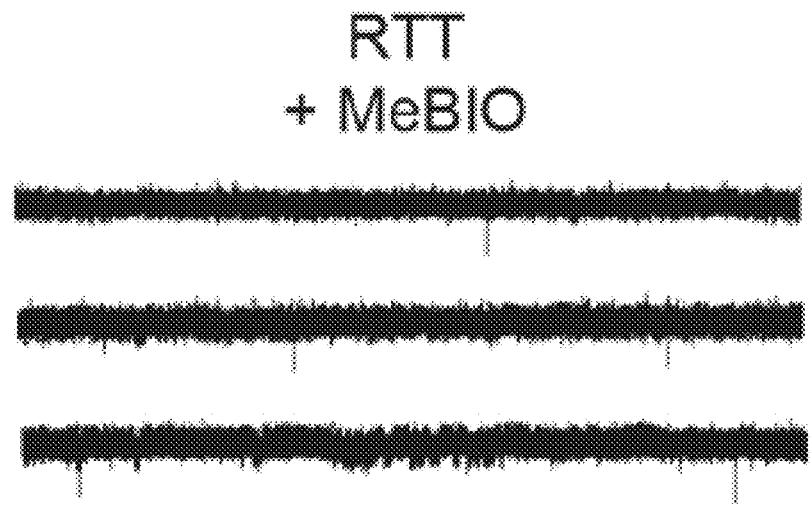
Figure 12H:
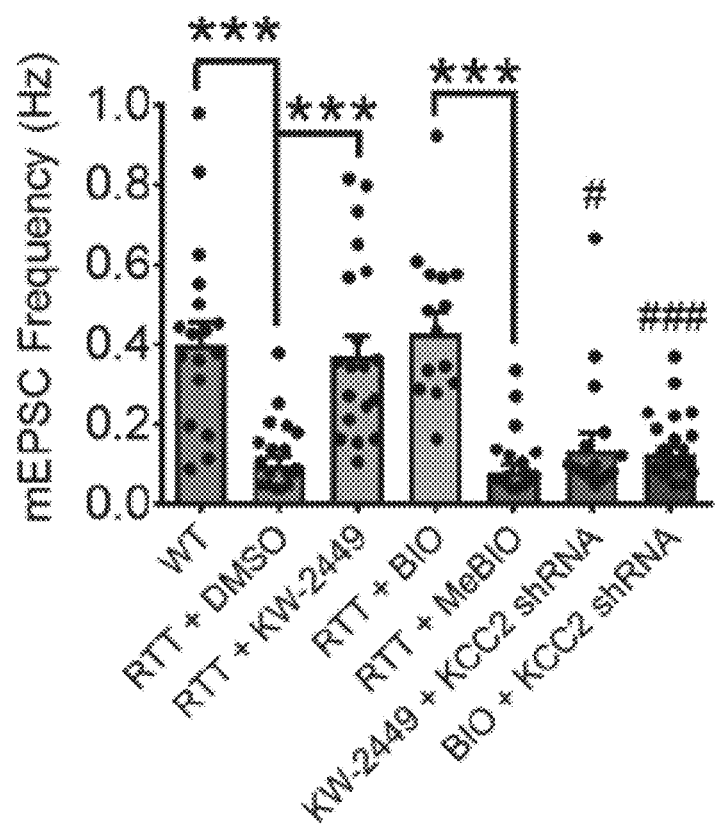
Figure 13A:
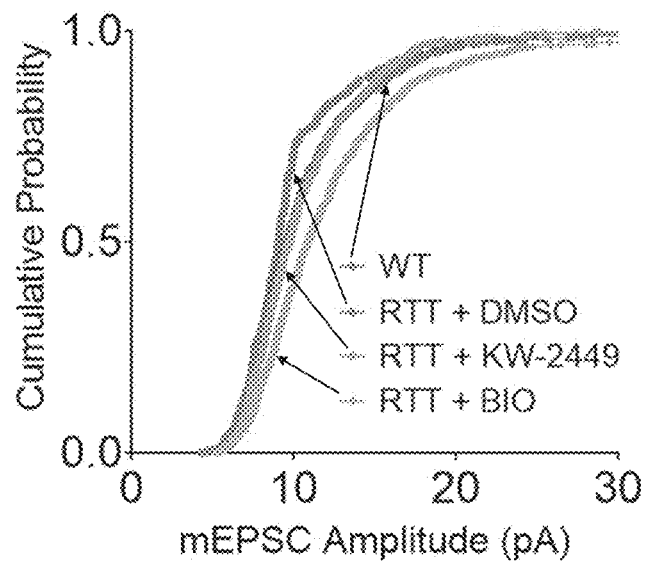
FIG. 13A shows that the amplitudes of mEPSCs are significantly smaller in RTT neurons (red trace) compared to WT neurons (green trace). Treatment of RTT neurons with KW-2449 (orange trace) or BIO (blue trace) rescued the deficit in mEPSC amplitude in RTT neurons ($p<0.001$ comparing to the RTT+DMSO group, determined by Kolmogorov-Smirnov test).
Figure 13B:
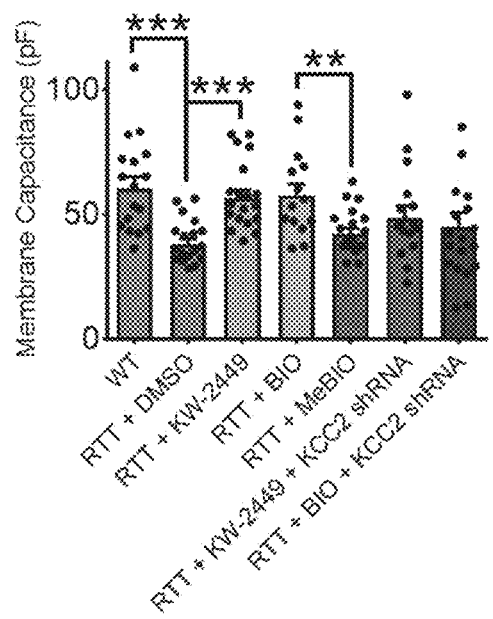
FIG. 13B shows that the membrane capacitance (Cm) values are significantly reduced in RTT neurons comparing to WT neurons. Treatment of RTT neurons with KW-2449 or BIO rescues the reduction in Cm, while the inactive analog MeBIO failed to change Cm. Transfection of RTT neurons with KCC2 shRNA abolished the capability of KW-2449 and BIO to increase neuronal Cm ($p>0.5$ comparing to the RTT+DMSO group). Data shown as mean±SEM.  $p<0.01$, * $p<0.001$, determined by one-way ANOVA.
Figure 14A:
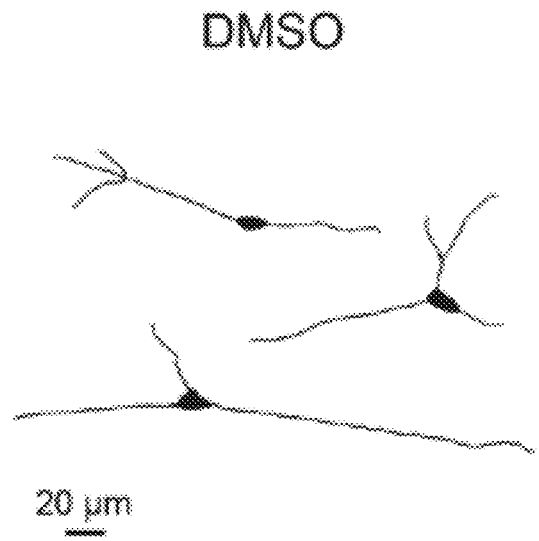
FIGS. 14A to 14H show that treatment of cultured human RTT neurons with KW-2449 or BIO rescue morphological deficits.
Figure 14B:
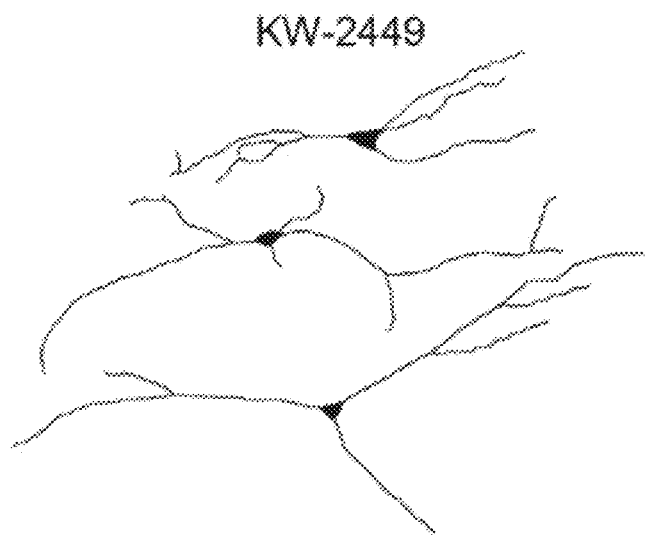
Figure 14C:
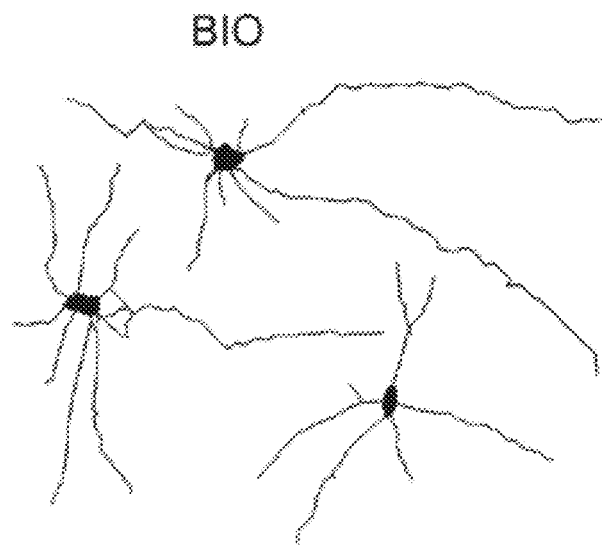
Figure 14D:
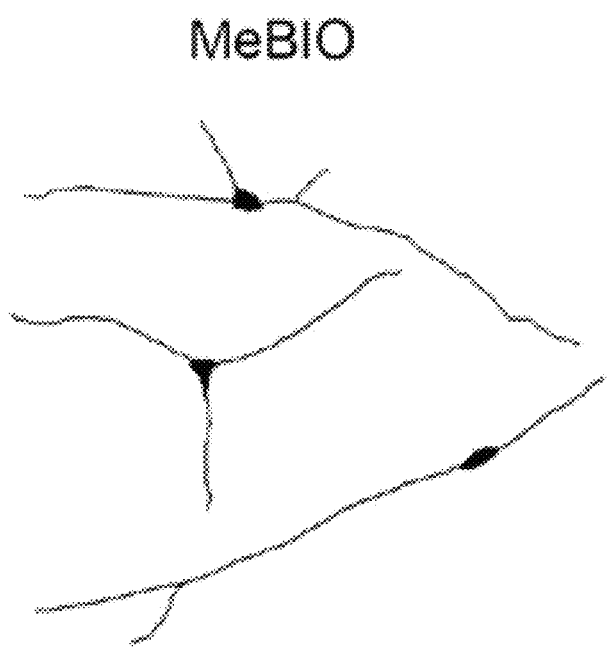
Figure 14E:
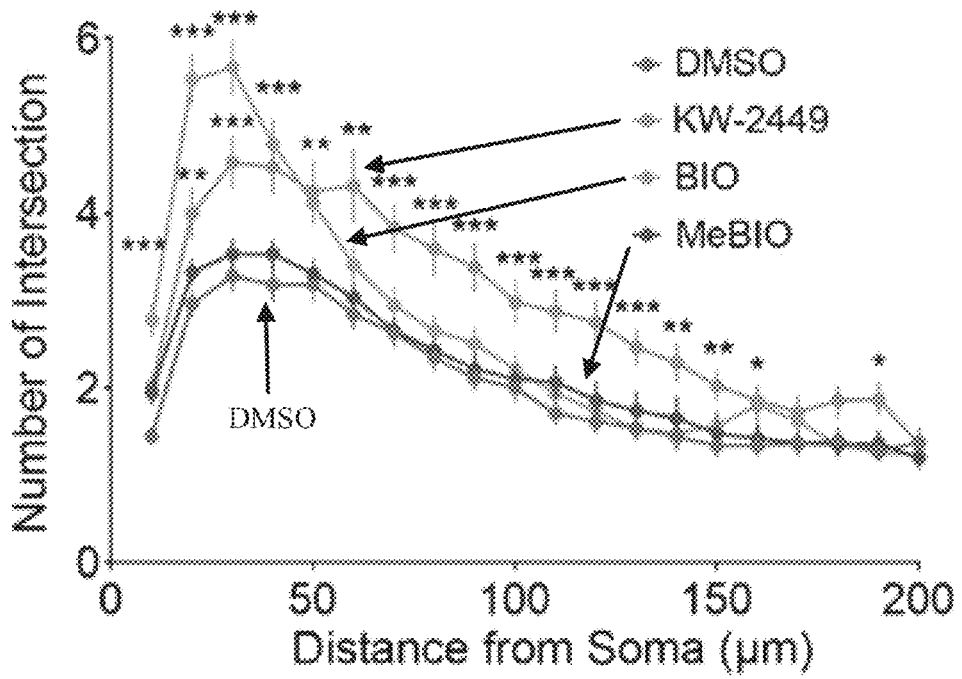
Figure 14F:
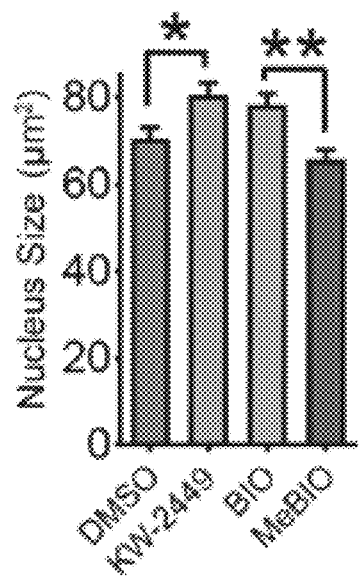
Figure 14G:
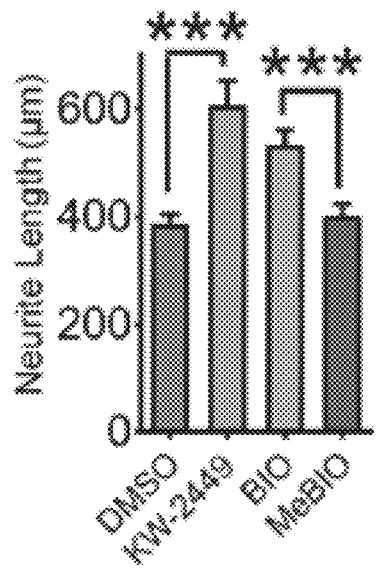
Figure 14H:
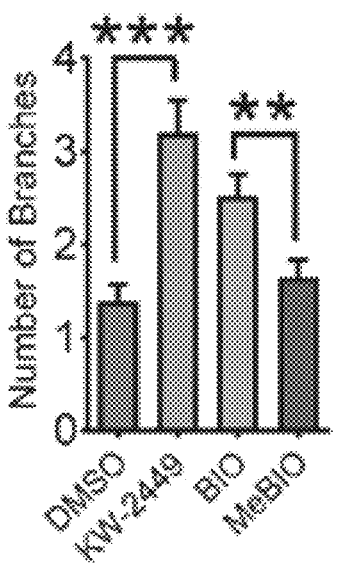

Example 5: Rescue of the Morphological and Functional Deficits in RTT Neurons by KEECs Previous work demonstrated that a reduction in the expression of KCC2 expression in the RTT neurons leads to a depolarizing shift in $E_{GABA}$, which indicates an impairment in GABAergic inhibition (7, 52). Moreover, a reduction in the number or the strength of excitatory glutamatergic synapses in RTT neurons has been observed in postmortem RTT patient brain samples (30), mouse models of RTT (53), and human stem cell-derived RTT neurons (54). Electrophysiology recording was utilized to assess whether KEECs could rescue the deficits in $E_{GABA}$ and excitatory synaptic transmission of RTT neurons. Results from gramicidin perforated patch recording experiments indicated that the cultured human RTT neurons treated with DMSO has $E_{GABA}$ values of about −50 mV, which represents a significant depolarizing shift compared to the average value of −70 mV in WT neurons (FIG. 12A). Treatment of RTT neurons with KEECs including KW-2449 and BIO, but not the inactive compound MeBIO, induced a significant hyperpolarizing shift in $E_{GABA}$ to levels comparable to WT neurons (FIG. 12B). Compared to WT human neurons, DMSO-treated RTT neurons showed a severe reduction in the frequency of miniature excitatory postsynaptic currents (mEPSCs), indicating reductions in the number of excitatory synapses (FIGS. 12C, 12D). Treatment of RTT neurons with KW-2449 (FIG. 12E) or BIO (FIG. 12F), however, significantly increased the frequency of mEPSCs to levels equivalent to WT control, while treatment with the inactive compound MeBIO failed to rescue synaptic deficits in RTT neurons (FIGS. 12G, quantified data shown in FIG. 12H). Statistical analyses revealed that treatment with KW-2449 or BIO significantly increased mEPSC amplitude, an indicator of synaptic strength (FIG. 13A, p<0.001 for both KW-2449 and BIO groups compared to DMSO control). We further investigated whether the beneficial effect of KEECs is a direct result of the increases in neuronal KCC2 gene expression. In RTT neurons transfected with a shRNA construct that knocks down KCC2 gene expression, treatment with KEECs KW-2449 or BIO failed to hyperpolarize the $E_{GABA}$ (FIG. 12B). Similarly, KCC2 shRNA transfection abolished the effect of KW-2449 or BIO to enhance mEPSC frequency (FIG. 12H). Thus, our results demonstrate that KEECs rescue the deficits in GABAergic and glutamatergic signaling through upregulation of KCC2 gene expression. Deficits in a number of morphological measurements, including nuclei size and neurite complexity and branching, are hallmarks of RTT neurons (54-56). These morphological metrics were quantified in cultured human RTT neurons treated with KEECs including KW-2449 or BIO, as well as DMSO or MeBIO as controls (FIGS. 14A to 14D). Comparing KEECs or control compounds-treated groups, a significant increase in the size of neuronal nucleus (FIG. 14F), and an enhancement in the length and complexity of MAP2+neurites (FIGS. 14E, 14G, 14H) were observed in KEEC-treated RTT neurons. To validate the morphological measurements, electrophysiological measurements of the neuronal membrane capacitance (Cm), an indicator of neuronal cell size (57) that is reduced in RTT neurons, were conducted. KW-2449- or BIO-treated RTT neurons display a significantly higher Cm, at levels comparable to isogenic WT human neurons, than RTT human neurons treated with DMSO or MeBIO control, suggesting a recovery of neuronal cell size and dendritic arborization in KEEC-treated RTT neurons (FIG. 13B). Interestingly, knocking down KCC2 with a shRNA construct abolishes the increase in Cm induced by KEECs (P>0.5 comparing to the DMSO control group). In summary, the data demonstrate that KEECs treatment significantly improves both morphological and functional deficits in RTT neurons to levels equivalent to those seen in WT neurons.

Figure 15A:
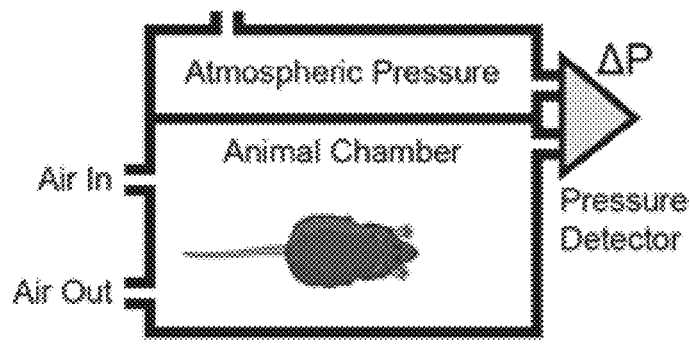
FIGS. 15A to 15N show that treatment of Mecp2 mutant animal model of RTT with KW-2449 or Piperine rescue RTT disease-related breathing pauses and locomotion deficits.
Figure 15B:
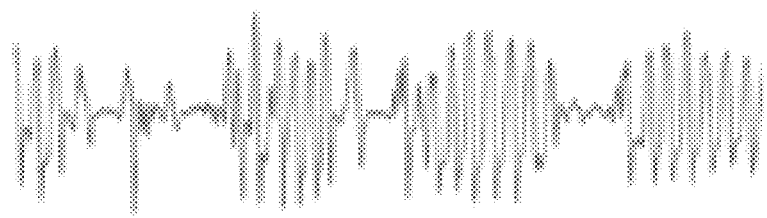
FIGS. 15B to 15D show representative breathing traces from DMSO (FIG. 15B) and KEEC KW-2449 (FIG. 15C)-injected Mecp2 mutant animals. Injection of KW-2449 induces a significant reduction in breathing pause frequency comparing to DMSO control (FIG. 15D).
Figure 15C:
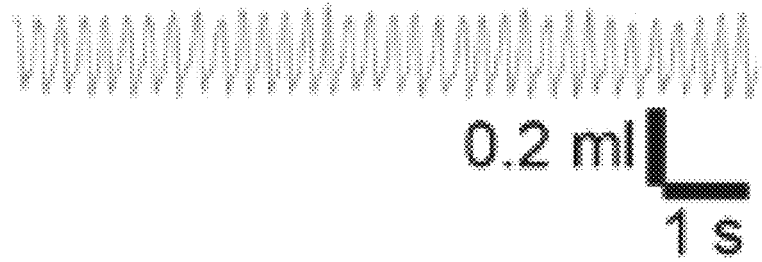
Figure 15D:
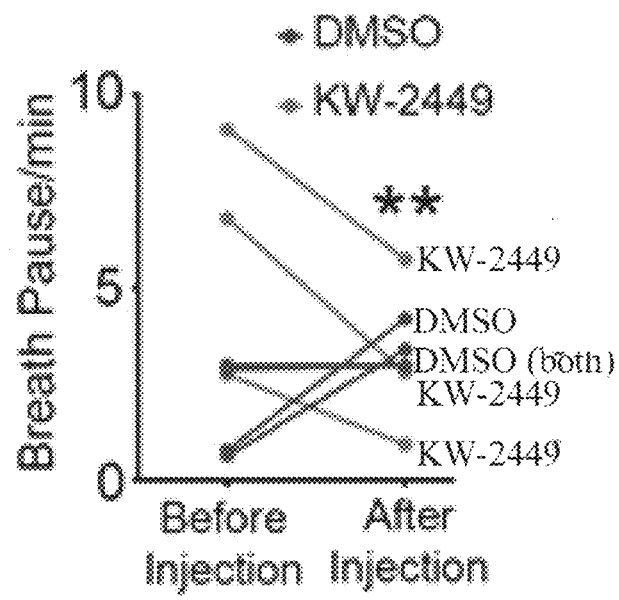
Figure 15E:
FIGS. 15E to 15G show representative breathing trace from EtOH injected (FIG. 15E) and KEEC Piperine injected (FIG. 15F) Mecp2 mutant animals. Injection of Piperine induces a significant reduction in breathing pause frequency comparing to EtOH control (FIG. 15G).
Figure 15F:
Figure 15G:
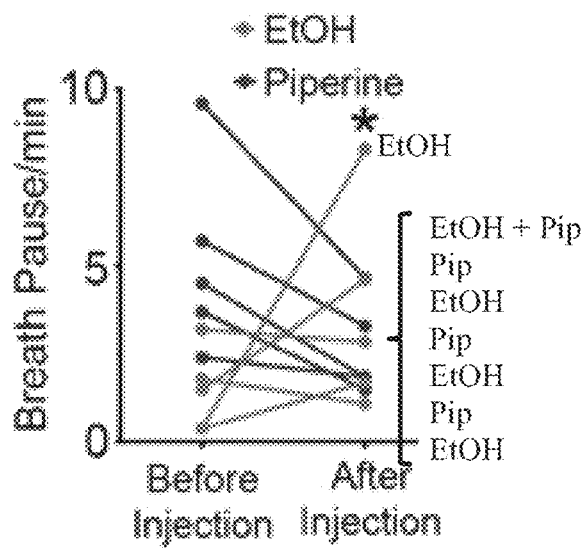
Figure 15H:
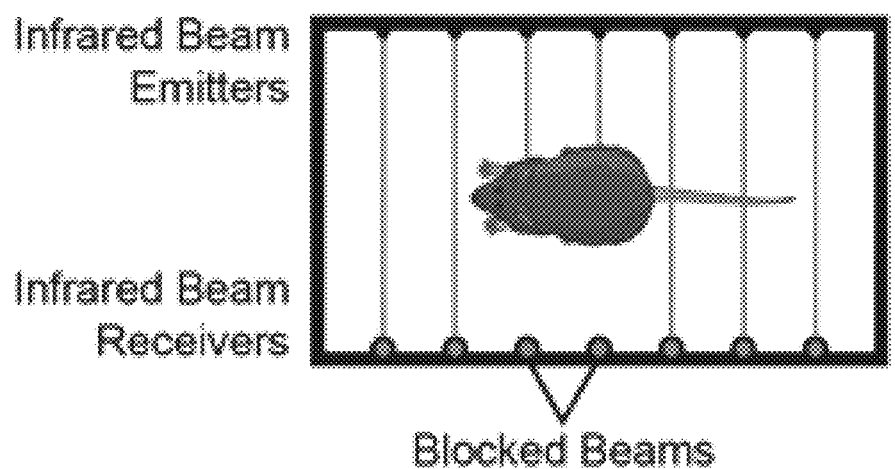
FIG. 15H is a diagram depicting the locomotion behavior experiments.
Figure 15I:
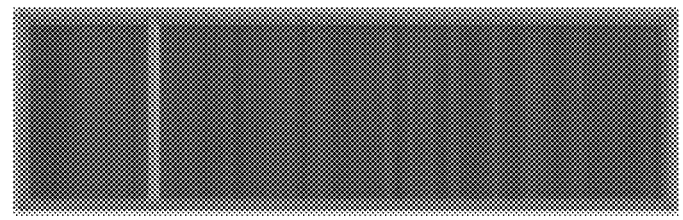
FIGS. 15I to 15K show representative night-time locomotion activity time series heatmap for DMSO injected (FIG. 15I) and KEEC KW-2449 injected (FIG. 15J) Mecp2 mutant animals. Injection of KW-2449 significantly increased nighttime locomotion in Mecp2 mutant animals, measured as infrared beam break frequency in home cage, comparing to DMSO control (FIG. 15K).
Figure 15J:
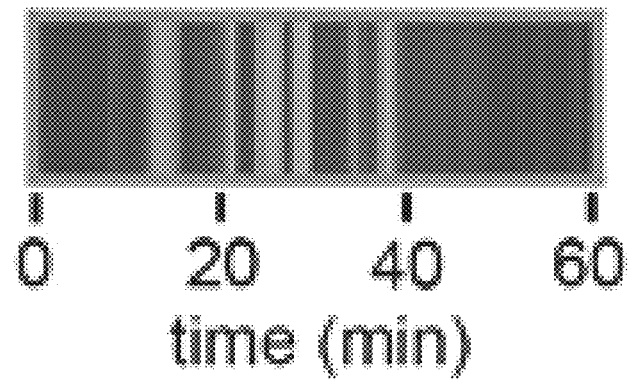
Figure 15K:
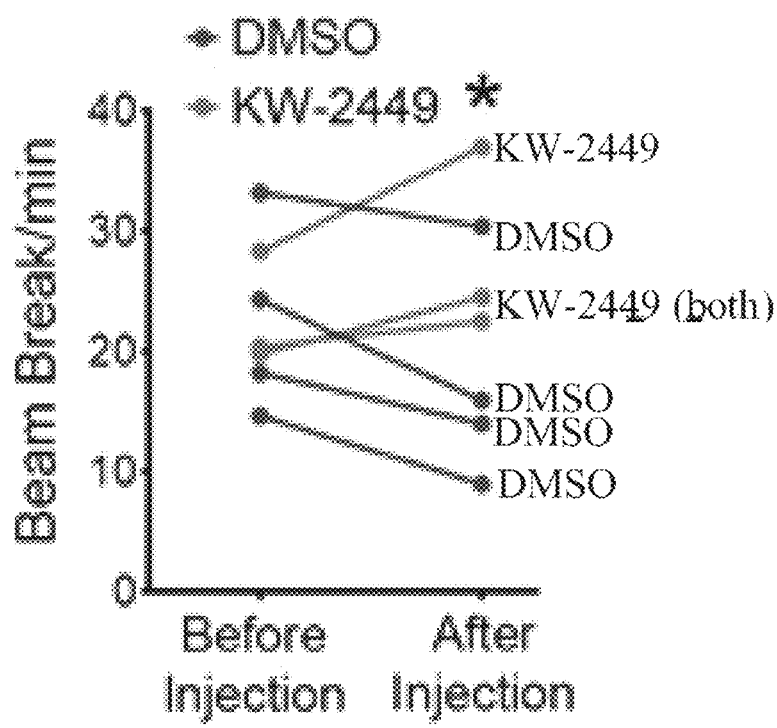
Figure 15L:
Figure 15M:
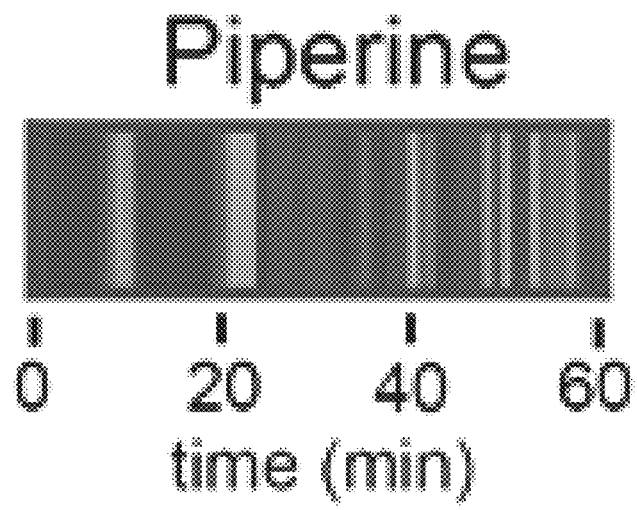
Figure 15N:
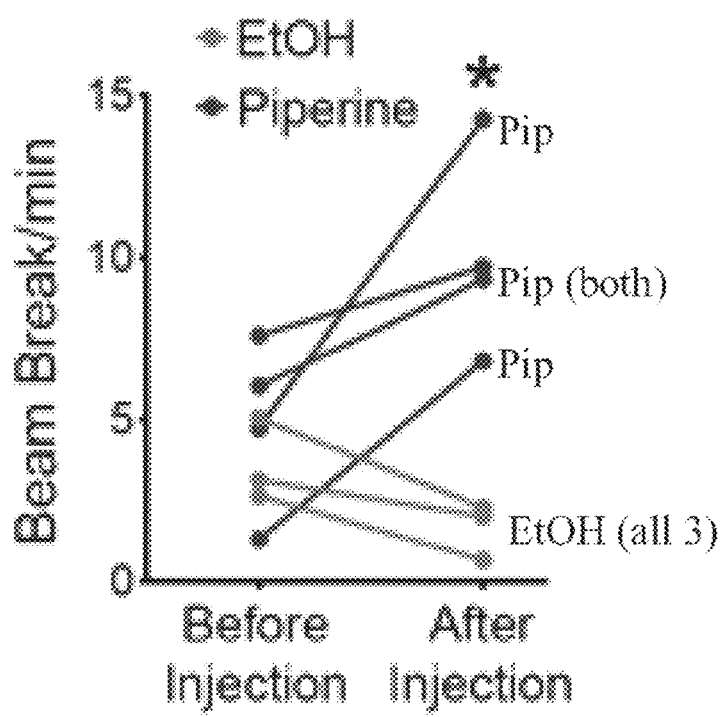

Example 6: KEECs Ameliorate Behavioral Deficits in a Mecp2 Mutant Mouse Model of RTT We assessed the in vivo efficacy of KEECs by treating RTT disease-related symptoms such as breathing pauses and reduced locomotion (58) in a Mecp2 mutant mouse model of RTT. The results shown in FIG. 10C and FIG. 10J indicate that KW-2449 or Piperine treatment of cultured RTT neurons induced a significant increase in KCC2 expression. Because previous work had demonstrated that intraperitoneal (IP) injection of Piperine improved symptoms in mouse models of autism and depression (59, 60), we assessed whether injection with KEECs including KW-2449 or Piperine could rescue breathing and locomotion deficits, which had been shown to reflect impaired GABAergic signaling (61). Plethysmograph and locomotion measurements were made in 4-6 week-old male Mecp2 mutant animals as a pre-treatment control time point and were then injected daily with KEECs KW-2449 or Piperine. Injection of the solvent DMSO or ethanol (EtOH) served as vehicle controls (FIG. 15A). The same two behavioral measurements in vehicle or KEEC-injected Mecp2 mutant animals were performed again two weeks after the start of daily injections. Each animal's 'after injection' data were compared to the 'before injection' level to assess behavioral changes. As a result of disease progression, DMSO-injected control Mecp2 mutant animals showed an increase in breathing pause rate (FIG. 15D, red lines, n=4 animals) and a decrease in locomotion activity (FIG. 15K, red lines). In contrast, treatment of Mecp2 mutant animals with KW-2449 significantly reduced the frequency of breathing pauses (representative Plethysmograph traces are shown in FIGS. 15B, 15C, quantified data shown in FIG. 15D), and induced a remarkable increase in locomotive activities (FIGS. 15I to 15K, n=3 animals), compared to DMSO-injected control. Similarly, treatment of Mecp2 mutant animals with Piperine significantly reduced the frequency of breathing pauses (FIGS. 15E to 15G), and increased locomotive activities (FIGS. 15L to 15N, n=3 for EtOH, n=4 animals for Piperine group), compared to EtOH-injected control. These in vivo experiment results demonstrate that KEECs treatment ameliorates disease-related behavioral pathologies in Mecp2 mutant animals, and thereby attest to the therapeutic potential of KEECs.

Discussion

As described herein, CRISPR/Cas9 gene editing technology was utilized to develop a compound-screening platform that provides a robust and convenient readout of the transcriptional and translational level of KCC2 from its endogenous locus in human neurons. Unbiased chemical screening approaches led to the identification of a group of small molecule KCC2 expression enhancer compounds (KEEC) that significantly increased the KCC2 reporter signal. The ability for KEECs to increase KCC2 expression levels was validated by mRNA and protein quantification performed both in cultured human neurons and organotypic mouse brain slices. Previous data showed that neurons in the RTT brain exhibit reduced KCC2 expression, which led to a depolarizing shift in GABA reversal potential, and impaired excitatory synapse development (7, 54). We demonstrate here that treatment with KEECs significantly increased KCC2 expression, and rescued the deficits in GABA functional switch and excitatory synapse development in RTT neurons to levels equivalent to their isogenic WT control in a KCC2-dependent manner. We also show that KEECs treatment rescues the immaturity in morphological development in RTT neurons. Without wishing to be bound by any theory, this is likely a secondary effect of the enhanced neuronal functional maturation levels. We further show that injection of KW-2449 or Piperine into Mecp2 mutant animal model of RTT ameliorated apnea and lethargy, two disease-related phenotypes of Mecp2 mutant animals associated with impairments in KCC2 expression and GABAergic inhibition (62, 63). The KEECs identified herein suggest a novel strategy for brain disease therapy aimed at restoring the impaired E/I balance in the neural circuitry through enhancement of KCC2 expression. Our target gene-specific reporter approach that robustly detects the transcriptional and translational levels of a therapeutic target gene, KCC2, in neurons allowed us to assess the effects of KEECs on relevant neuronal phenotypes. In cultured RTT neurons, treatment with KEECs KW-2449 and BIO restored the impaired KCC2 expression and rescued deficits in both GABAergic and glutamatergic neurotransmissions. Previous data suggested that disrupted Cl⁻ homeostasis in the brainstem causes abnormalities in breathing pattern (62) consistent with breathing abnormalities seen in animals carrying a conditional Mecp2 deletion in GABAergic neurons (65). The reduction in locomotion activity observed in the Mecp2 mutant animals has also been attributed to abnormalities in the GABAergic system (63). Therefore, without wishing to be bound by any theory, treatment with the KEECs KW-2449 or Piperine may ameliorate disease phenotypes in Mecp2 mutant animal model of RTT through restoration of the impairments in KCC2 expression and GABAergic inhibition.

KEECs described herein may, among other things, help to elucidate the molecular mechanisms that regulate KCC2 expression in neurons. A previous study conducted with a glioma cell line showed that KEEC Resveratrol activates the SIRT1 pathway and reduces the level of NRSF/REST (66), a transcription factor that suppresses KCC2 expression (51). Our results demonstrate that Resveratrol increases KCC2 expression by a similar mechanism, which could contribute to the therapeutic benefit of Resveratrol on a number of brain disease conditions (67, 68).

We also identified a group of GSK3β pathway inhibitors as KEECs. Overactivation of the GSK3β pathway has been reported in a number of brain diseases (69). Thus, our results suggest that GSK3β pathway inhibitors could exert beneficial effects on brain function through stimulating KCC2 expression. Another major KEEC target pathway, the FLT3 kinase signaling, has been investigated as a cancer therapy target (70, 71). Although FLT3 is expressed in the brain (72), drugs that target FLT3 pathway have not been extensively studied as potential treatments for brain diseases. Our results provide what we believe is the first evidence that FLT3 signaling in the brain is critical for the regulation of key neuronal genes such as KCC2.

As described herein, we investigated the efficacy of KEECs to rescue a number of well-documented cellular and behavior phenotypes of RTT, including impaired GABA functional switch, reductions in excitatory synapse number and strength, immature neuronal morphology (53, 54), as well as an increase in breathing pauses and a decrease in locomotion (83). Impairment in KCC2 expression has been linked to many brain diseases (2, 84) including epilepsy (85-87), schizophrenia (4, 5, 88), brain and spinal cord injury (6, 89), stroke and ammonia toxicity conditions (90-92), as well as the impairments in learning and memory observed in the senile brain (25). Thus, a phenotypically diverse array of brain diseases may benefit from enhancing expression of KCC2 can be of benefit in a phenotypically diverse array of brain diseases.

Materials and Methods

Generation of KCC2-2A-luciferase Reporter Cell Lines

Male WT ES colonies #22 (from the WIBR1 hESC line (Lengner, C. J. et al., Cell, 2010, 141, 872-83) and its isogenic RTT ES colony #493 (created by knocking out one exon of MeCP2, resulting in absence of MeCP2 protein) were used for gene targeting. One confluent 6-well plate of ES cells were dissociated with 0.05% trypsin (Gibco, Catalog number: 25300054) for 5 minutes. Cells were rigorously triturated in PBS to achieve single-cell suspension, and filtered through a 40 µm cell strainer to get rid of undissociated ES cell chunks and MEF aggregates. The cells were then spun down, resuspended with 500 µl ice-cold PBS, and mixed with 30 µg DNA constructs (10 µg guide RNA construct, 20 µl targeting template). The sgRNA sequence for CRISPR/Cas9-mediated targeting of the KCC2 locus is: ACCATCTACTCCTGAGAACC. The link between the exon 26 of KCC2 gene and firefly luciferase reporter is a V5-HA-P2A sequence: GGCAAACCGATTCCGAATCCGCTGCTGGGCCTGGATTCCACCTACC-CATACGATG TTCCAGATTACGCTgccactaacttetecetgtt-gaaacaagcagggggatgtcgaagagaatcceggcca (SEQ ID NO: 1, wherein the P2A sequence is shown in lower case. The cell-DNA mix was transferred to an electroporation cuvette (Bio-Rad, Catalog number: 165-2088). A Bio-Rad Gene Pulser Xcell electroporator was used to deliver electroporate DNA constructs into ES cells. The cells were immediately collected (into medium containing ROCK inhibitor) and seeded onto one plate of MEF cells.

Two days after the electroporation, the cells were dissociated with trypsin and sorted based on the GFP fluorescence (from the PX330 guide RNA backbone). Typically from 3,000 to 10,000 cells were collected from the FACS sorting. The GFP+single ES cells were seeded into 6-well MEF wells at a density of <5,000 cells per well (typically about 1,000 cells/well). After 10-14 days, individual ES cell colonies emerged. Individual colonies were picked into 12-well plates. Gene-targeted ES colonies were genotyped with PCR, followed by Southern blot analysis to confirm luciferase insertion into the correct genetic locus. Two homozygously targeted colonies (#13, #31) were generated from WT #22 ESC, and one homozygously targeted colony (#35) was generated from RTT #493 ESC.

Culture of Human Embryonic Stem Cell, Neuroprogenitor, and Neurons

Embryonic Stem (ES) Cell Culture

Human female WT ES cells #396 were derived in the Whitehead Institute (WIBR3) and isogenic MeCP2 mutant ES cell lines #913 were generated through TALEN genome-editing (93). Only one of the MeCP2 copy was targeted by TALEN, therefore the mutant clone is heterozygous for MeCP2 mutation. Since the WIBR3 ES cells maintain a stable XaXi state (one active and one inactive X chromosome) in culture, the targeted MeCP2 allele is on the active chromosome while the wild-type allele is on the inactive chromosome, resulting in complete loss of MeCP2 in mutant ES cells and differentiated cells.

ES cells were maintained on mouse embryonic fibroblast (MEF) feeder cells in hES medium. Once ES cells reached approximately 70% confluence, enzymatic dissociation was performed using collagenase V (Invitrogen, 1 mg/1 ml) for 30 minutes and the cells were split 1:3 onto MEF cells for each passaging.

Neural Progenitor Cell (NPC) Generation

Human female ES cells (WIBR3) and human male ES cells (WIBR1) were derived in the Whitehead Institute (Lengner, C. J. et al., Cell, 2010). MeCP2 mutant ES cell lines (clone #913) were generated through TALEN genome-editing (93).

First, on the day before NPC derivation, a 6-well plate coated with growth factor-reduced Matrigel (BD Bioscience, 47743-720) and diluted 1:40 with DMEM. On day 1, the ES cell culture was washed with PBS, and the ES cell colonies were dissociated with 1 mg/ml collagenase V (Life Technologies) for 30 minutes. Next, the ES colonies were collected into a 15 ml Falcon tube. The ES colonies were separated using gravity-sediment method and washed twice with hES medium. Then the ES colonies were digested with 1 ml Accutase for 15 minutes in a 37° C. incubator. A P1000 pipet was used to rigorously triturate the digested ES colonies (approximately 20 times). The fully dissociated hES colonies were resuspended with 10 ml mTeSR medium. Then, the cell suspension was filtered through a 100 µm cell strainer to acquire single cell suspension. Next, the cells were counted with Countess automated cell counter (Invitrogen). Two million cells were seeded into one well in a six-well plate coated with Matrigel and Rock Inhibitor was added to the ES cell suspension to reduce cell death. On day 2, the culture medium was changed with mTeSR. This was performed on a daily basis after seeding. On day 3 and after, the cell density was monitored after plating. Once the cells were fully confluent, the mTeSR medium was changed gradually (¼ volume increment per day) into NPC medium with 2 µM Dorsormorphin (Stemgent, Cat #: 04-0024). Next, when NPC Rosettes were apparent (usually 4-7 days after switching to NPC medium), NPC cultures were passaged with Accutase and with the addition of rock inhibitor to reduce cell death. The cells were split 1:2 onto Matrigel-coated plates. Then, when the NPC cells were stably expanding, the Dorsormorphin was removed from the NPC medium. Next, 20 ng/ml of human recombinant FGF2 (Life Technologies, PHG0263) was added to promote NPC self-renewal and maintain multipotency. Two to three rounds of expansion/passaging yielded sufficient amount of cells for conducting experiments and establishing frozen stock. Once NP cells reached confluence, the number of cells seeded per well (6-well plate) was 10-15 million.

Neuronal Differentiation

On day 1, two confluent wells were dissociated from the 6-well plate that contained a total of approximately 20 million NPC cells with Accutase for 15 minutes at 37° C. The cells were spun down at 750 rpm for 5 minutes and resuspended with neuronal medium by gentle trituration. Next the cell suspension was filtered through a 100 µm mesh to get rid of clumps. The resulting single-cell suspension was cell-counted using a Countess apparatus (Invitrogen Countess Automated Cell Counter, Catalog no. C10227) and resuspended with Neuronal medium to reach a density of 1 million cells/ml. The number of neurons that can be obtained from a T75 flask is roughly 20 million. The dissociated NP cells were plated with 20 ml neuronal medium into a T75 flask coated with Matrigel. On day 2, the culture medium was completely changed with neuronal medium. On day 3 through day 30, the neuronal medium was changed fully on weekly basis (or when medium seemed acidified).

Screening Setup

35 RTT KCC2 reporter ESC is generated by targeting the KCC2 locus of #493 RTT ESC generated by knocking out MECP2 gene in the WIBR1 ESC line (93) to insert a 2A-luciferase reporter. #35 ESC that has both KCC2 alleles targeted with luciferase reporter were differentiated into #35 NPC, then #35 RTT KCC2 reporter neurons. The cells were dissociated with Accutase and resuspended in 10 ml neuronal differentiation medium to count cells. The cells were then diluted to the final density of 200,000 to 500,000 cells/ml. Matrigel was added to the cell suspension at a dilution ratio of 1:300 to promote cell adhesion after plating. AraC was added to cell suspension at the concentration of 2 µM to inhibit cell division. The cells were plated into 96-well plates with an automated cell seeding machine using the following protocol: The neuron flask was washed with PBS. The neurons were digested off the plate with Accutase for 30 minutes at 37° C. Next, the dissociated cells were collected and spun down at 750 rpm for 5 minutes. The cell pellet was dissociated by gentle trituration with P1000 pipet and the cells were resuspended with 10 ml of neuronal medium. Then, the cells were filtered through a 40 µm cell strainer (Falcon) to get rid of clumps. The resulting single-cell suspension was counted using a Countess automated cell counter (Invitrogen Countess Automated Cell Counter, Catalog no. C10227). The neurons were resuspended with neuronal medium to 10× of the destination density (100,000 cells to 400,000 cells per ml). The cells were plated with a multichannel pipette, or proceeded to the machine-plating protocol described below:

For the machine-plating protocol, the plating machine (Multidrop 384, Labsystems) tubings were washed 2× with 70% EtOH. Then, the plating machine tubings were washed 2× with PBS. Next, the plating machine was used to dispense 100 µl cell solution/well to the destination areas in 96-well plates. A typical cell seeding area consisted of a total of 6 rows, 11 columns, which required a 6.6 ml cell suspension per plate.

The day after cell seeding, small molecule compounds from the IRSF (International Rett Syndrome Foundation) library were prepared at a concentration of 1 mM and dispensed into a blank V-bottomed test plates at 2 µl per well. Compound solvent DMSO was included in every plate as control. Using a liquid handling robot, about 80 µl of culture medium were discarded. Neuronal medium in the volume of 200 µl was added to the V-bottom test plate that contained 2 µl of 1 mM compounds, and mixed with compounds by pipetting up-and-down 3 times. The medium that contained the 10 µM compounds was then applied to the neuronal cell culture and incubated for 2 weeks before cell lysis and luciferase assay were performed.

A method to seed neurons in 100 µl medium on the first day was also tested successfully. On the second day, the compounds were dissolved at 5× concentration in neuronal culture medium, then 25 µl of compound-containing medium was added to the original medium to reach 1× compound concentration to treat cells.

For some screens, human WT (clone #13 or #31) or RTT (clone #35) KCC2 reporter neurons were differentiated in T75 flasks for 4 weeks from NPC with the method similar to previously described protocol (93). The cells were dissociated with Accutase, resuspended in 10 ml neuronal differentiation medium to count cells. the final cell seeding density was 20 k-40 k cells per well for 96-well plates, and ~10 k cells per well for 384-well plates. Matrigel was added to the cell suspension at a dilution ratio of 1:300 to promote cell adhesion after plating. AraC were added to the cell suspension at the concentration of 0.5 µM to inhibit astroglial cell division. The cells were dispensed into 96-well or 384-well plates (Coming) using a BioTek EL406 plate dispenser. One day after neuronal cell seeding, small molecule compounds from the IRSF library, ICCB known bioactive library (Enzo, Cat #BML-2840), or LINCS kinase inhibitor libraries were added to the cells at the final concentrations of 10 µM, 10 µM, and 0.5 µM, respectively, using a V&P pin transfer tool mounted on the MCA96 head of a Tecan Freedom Evo 150 liquid handling robot. The neurons were incubated with the compounds at 37° C./5% $CO_2$ for a week before the luciferase assay.

Luciferase Assay

The cells used for luciferase assay were KCC2 reporter neurons differentiated for 4 weeks, and treated with drug in 96-well format for 2 weeks. Cell density was between 20 k-40 k cells per well.

On the day of the luciferase assay, the cells were washed with PBS for two times, and 100 µl of cell lysis buffer was applied to the washed cells. The cell plates were transferred to a rocker to shake for 10 minutes in order to fully lyse the cells. A liquid-handling robot was used to transfer 30 µl of lysate to a different blank white plate for Cell Titer Glo (CTG) reading. First, the cells were washed twice with PBS. Then, the cells were lysed for 10 minutes at room temperature with 100 ul 1× passive lysis buffer (Promega, E1941, 1:5 diluted with water). Then, 30 ul of lysate was transferred to a copy plate for CTG reading. Next, 20 ul of the luciferase assay buffer (Promega, E1501, diluted with provided buffer) was injected to the original plate which has 70 ul lysate, and the luciferase signal was read immediately on a Thermo Fischer Fluoroskan Ascent plate reader. Finally, 70 ul of diluted CTG buffer (Promega, G7572, 2:5 diluted with water) was added to a copy plate with 30 ul of lysate and incubated for 10 minutes before the CTG signal was read.

A Thermo-Fischer Ascent Luminoskan plate reader was used to read luciferase luminescence. An injection volume of 20 µl was chosen because dose-response experiment showed that 20 µl was already sufficient to elicit maximal response in a luciferase activity. For each well, 1 second after the luciferase reagent injection, the luminescence signals were integrated for 1 second. For the CTG reading, the CTG reaction agent was diluted with water 2:5, and a volume of 70 µl was injected to 30 µl of cell lysate. CTG assay plates were put on a rocker for 10 minutes and then read with the Luminoskan plate reader with the integration time of 100 ms. The luciferase signals were normalized to the CTG signal as control and the data was normalized to the in-plate DMSO control.

For some screens, on the day of the luciferase assay, the cells were washed with PBS three times using a BioTek EL406 plate washer. Cell lysis buffer (Promega, E1941, 1:5 diluted with water) was added at a volume of 100 µl per well for 96-well plates and 30 µl per well for 384-well plates, and incubated at room temperature for 10 minutes to lyse the cells. A fraction of the cell lysate (30 ul for 96-well, 5 ul for 384-well) was transferred to a new white, opaque plate and Cell Titer-Glo (CTG, Promega, G7572, diluted 2:5 in water) was added and incubated for 20 minutes at room temperature. CTG measures cellular ATP levels as a surrogate for cell viability. The reporter luciferase signal was assayed in the original source plate using Bright-Glo reagent per the manufacturer's protocol (Promega, E1501, 10 ul for 96-well plates, 3 ul for 384-well plates). Assay readouts were performed on a Tecan M1000 Infinite plate reader. For data analysis, the luciferase signal was normalized to the CTG signal to control for number of live cells per well. The Luc/CTG ratio data were then normalized to the in-plate DMSO control to calculate the signal induction fold change. Screening data were processed with CellHTS2 software package to calculate B-score (94)

Brain Slice Culture and Drug Treatment

Brain slice cultures were prepared from P1 neonatal mouse according to a protocol described by Antonio del Rio et al., Nature Protocols, 2010. Cerebrum slices (1 mm in thickness) were prepared from neonatal mouse brain, and were transferred to 6-well culture inserts with the pore size of 0.4 µm. The insert was placed in 6-well plates with 1 ml of culture medium. Three days after the initial culture, compounds and DMSO control were added to the medium. Alternately, in some experiments, brain slice cultures were prepared from P3 neonatal mouse according to a protocol described by Antonio del Rio et al., Nature Protocols, 2010. Cerebrum slices (1 mm in thickness) were prepared from neonatal mouse brain, and were transferred to 6-well culture inserts with the pore size of 0.4 µm. The insert was placed in 6-well plates with 1 ml of culture medium. The day after the initial culture, compounds and DMSO control were added to the medium. The medium with fresh compounds was used to replace old medium every other day. One week after drug treatment, the brain slices were harvested for Western blot or qRT-PCR analysis.

Western Blot

Protein samples were collected from cultured brain slices or cultured neurons in 12-well format with RIPA lysis buffer (in mM: 150 NaCl, 25 Tris-HCl, 1 EDTA, 1% NP-40, 1% sodium deoxycholate, 0.1% SDS, with protein kinase inhibitor and protease inhibitor, pH adjusted to 7.6). A sonication step was applied to homogenize tissue and extract protein, followed by a 10 minute centrifugation at 4° C. The protein samples were mixed with NuPAGE LDS sample buffer, heated at 95° C. for 10 minutes, and then separated on NuPAGE 4-12% Bis-Tris gel and transferred to PVDF membrane. The PVDF membrane was blocked for 30 minutes with 5% milk in TBS+0.1% Tween 20 (TBST), and incubated overnight at 4° C. with primary antibodies diluted in TBST-milk at the following concentrations: KCC2 (1:2000, Millipore), NKCC1 (1:1000, Iowa Hybridoma bank), α-Tubulin (1:4000, Abcam), GAPDH (1:3000, Abcam), Actin (1:2000, Sigma Aldrich #A2066). The membrane was rinsed with TBST three times to wash off excess antibodies, and then incubated in secondary HRP antibodies in TBST-milk at 1:5000 concentration.

Chemiluminescence method (HRP substrate, Millipore) detected clear KCC2 protein monomer (~120 kDa) and dimer (>200 kDa) bands. The PVDF membrane was then stripped using the Re-blot plus strong solution (Millipore), and re-immunoblotted for NKCC1 (~150 kDa) to acquire KCC2/NKCC1 ratio. The area and intensity of protein signal was determined using ImageJ. The relative KCC2 and NKCC1 expression were calculated by normalizing protein signal to GAPDH or Tubulin loading control. Both monomeric and dimeric KCC2 bands were detected in P20 WT and gKO mouse brain, and were combined together while quantifying KCC2 expression. KCC2 expression during early development (P8) remained low and the KCC2 dimer band was faint. Hence, only the monomer band was quantified.

Quantitative RT-PCR Analysis

To prepare RNA samples from cultured organotypic brain slice, tissue samples were homogenized by passing through a 23 gauge needle for a number of times. Total RNA was extracted with Omega Total RNA kit and was reverse-transcribed into cDNA using the Invitrogen Superscript RT system and Oligo dT primer. SYBR green-based quantitative RT-PCR assay was performed to detect for the abundance of specific mRNA transcripts. The primer sequence for the detection of KCC2 expression in mouse brain samples are as follows: KCC2-Forward: CCGTGCCTGCAGAACATCTTTGGTGT (SEQ ID NO: 2); KCC2-Reverse: GCCACCAGCAGGCACAACACCAT-TGG (SEQ ID NO: 3). The primer sequence for detection of NKCC1 mRNA are as follows: NKCC1-Forward: GGCAC-CAAGGATGTGGTAGT (SEQ ID NO: 3); NKCC1-Reverse: TTGCAGTCTTGCCATCCTCT (SEQ ID NO: 4). The gene expression was calculated by normalizing the KCC2 data with the expression of housekeeping gene HDAC2 in every sample. HDAC2 expression was detected using the following primers: HDAC2-Forward: CTTTCCTGGAACAGGAGACTTGAGGG (SEQ ID NO: 5); HDAC2-Reverse: GGCTGGTACATCTCCAT-CACTTTTGAG (SEQ ID NO: 6). Relative gene expression levels were calculated by normalizing KCC2 or NKCC1 expression in drug-treated groups with that in DMSO controls with the housekeeping gene HDAC being used as internal control.

siRNA and Plasmid Transfection

Two different siRNA preparations were ordered per gene from Thermo Fischer with the following catalog numbers: mouse Flt3 (158581, 158583), mouse Gsk3β (185671, 185673), human FLT3 (s5290, s5291), human GSK3β (VHS40271, VHS40279). For the DIV2 mouse neuron or 1-month human RTT neurons cultured in 12-well plates, 20 nMol of siRNA were transfected per well with Lipofectamine RNAiMAX transfection reagent (13778030, Life Technologies). Six days later, protein samples were harvested from transfected cells.

RTT neurons that under KW-2449 or BIO treatment were co-transfected with GFP and a KCC2 shRNA construct (7) with a modified calcium-phosphate transfection method (96). GFP positive neurons that has the KCC2 level knocked down were recorded 6-8 days after transfection.

Neuronal Morphology Analysis

Cultured 2-month RTT neurons were treated with DMSO, KW-2449, BIO, or MeBIO for 1-2 weeks and subjected to PFA fixation and immunostaining with a MAP2 antibody (1:800, Encor). Fluorescent images of randomly-selected neurons were acquired on a Nikon Eclipse Ti epifluorescence microscope equipped with 20× lens. Nucleus size analysis of DAPI-stained neuronal nucleus were performed with ImageJ. Sholl analysis and measurements of the total neurite length and branch points were performed with the Simple Neurite Tracer plugin of the ImageJ software. Morphological analyses were carried out with about 60 randomly-selected neurons per treatment group. Image acquisition and analysis were carried out by different researchers, and automated analysis software pipeline were utilized to reduce human bias.

Electrophysiology

Functionally mature human neuron cultures were obtained by seeding female human WT or isogenic RTT NPCs on a layer of primary mouse astrocyte culture as previously described (57). In the cultured WT human neurons, KCC2 expression reaches mature level between 2-3 months (7). We therefore treated the WT or RTT human neurons 8-12 weeks in culture, with compounds for a duration of two weeks before conducting whole-cell patch-clamp recording. The extracellular bath solution, that perfused the recording chamber, consists of (in mM): 120 NaCl, 30 glucose, 25 HEPES, 5 KCl, 2 $CaCl_2$, 1 $MgCl_2$. The pH was adjusted to 7.3 with NaOH. The high-chloride internal pipette solution consists of (in mM): 147 KCl, 5 Na-phosphocreatine, 2 EGTA, 10 HEPES, 4 MgATP, and 0.5 $Na_2GTP$; the pH 7.3 was adjusted with KOH. To record mini EPSC, the membrane potential was held at −70 mV, and 0.5 μM of TTX and 50 μM Picrotoxin were applied with bath solution to block action potential and GABAergic synaptic transmission.

In order to estimate $GABA_A$ receptor reversal potential, Gramicidin perforated patch recordings were performed as described previously (7). Briefly, Gramicidin (G5002, Sigma) was diluted with high-chloride internal pipette solution to a final concentration of 50 μg/ml to perforate the membrane in a cell-attached recording configuration. If the cell membrane is ruptured during the perforation process, high-chloride pipette solution will immediately replace the cytosol and the $E_{GABA}$ will depolarize to ~+10 mV that is out of the physiological range. Membrane-ruptured neurons and the neurons that failed to perforate (access resistance >30 MΩ after 15 min of perforation) were excluded from the experiment.

To evoke GABA response, a pipette filled with 100 μM GABA solution was positioned 5-10 μm away from the neuronal cell body. Air pulses at the pressure of 10 p.s.i. and duration of 100 ms were generated with a Picrospritzer (Parker Instrumentation) to puff GABA solution onto neuronal cell body. Neuronal response to GABA puffs were recorded at different membrane holding potentials from −90 mV to +30 mV, and the $E_{GABA}$ values were calculated with linear regression. Electrophysiological signals were recorded with Multiclamp 700A patch-clamp amplifier and data were collected with Clamp 9 software (Molecular Devices, Palo Alto, CA), sampled at 10 kHz and filtered at 1 KHz. Off-line data analyses of mEPSC synaptic events were performed with MiniAnalysis software (Synaptosoft, Decator, GA). All experiments were performed at room temperature. A sample size of 5-8 neurons was used for $E_{GABA}$ measurements, while a sample size of 14-19 neurons was used for mEPSC measurements. All data were presented as mean±SEM. ANOVA test followed by the Bonferroni correction were used for statistical analysis. The Kolmogorov-Smirnov test was employed to compare the cumulative distribution between two datasets.

Animal Behavior Experiments

Male Mecp2 mutant mice (Mecp2$^{-/y}$, e.g. the Bird model) between 4-12 weeks of age were used for the in vivo experiments. Subjects were divided into drug treated KO (Piperine/KW-2449), and vehicle treated KO (EtOH/DMSO) groups. Animals were randomly assigned to treatment arms with approximately equivalent numbers in each group.

KW-2449 stock solution was prepared at 10 mg/ml with DMSO, and Piperine stock solution at 30 mg/ml with EtOH. 20 μl of stock solution were diluted with 1 ml saline for injection. Daily drug treatments or sham injections were performed on both groups between P28 and P56, for at least two weeks, as Mecp2 mutant mice start to show symptoms around P28 and die around P60. Both following tests were performed on both groups of mice before the injections start, and repeated at the end of the injection period. The animals' performance was then compared before and after drug/vehicle injections.

A full body plethysmograph chamber (EMKA Inc, PA) was used to measure breathing patterns. The subject was first familiarized with the chamber for 20 minutes before the pre-injection test. For each test, the subject was left in the chamber for 20 minutes, afterwards its breath pattern was recorded for the next 20 minutes, and the estimated amplitude modulation index (eAMI) was calculated from the breath trace to label breath pauses automatically. Only breath pauses longer than 1 second were used to calculate the average breath pause per minute at the time points before and after drug treatment.

To measure the subjects' nighttime locomotion, a 1-D infrared light-beam frame (ActiMot, TSE-systems, MO) was used. Animals were single-housed in new cages with the same setup as their home cages. The infrared monitor was set up for each cage and the beam crossings was recorded between 17:00 and 9:00 the next morning, where the lights were turned off between 19:00 and 7:00. The average beam crossing frequency during the night (21:00-5:00) was used as the subject's activity score, and the average beam crossing frequency after lights on (7:00-9:00) was used as the subject's day time activity score. The time periods where the mouse is stationary for >5 minutes are discarded to reduce artifact caused by the mouse sleeping. As we look at both day-time and night-time locomotion, a bonferroni correction with repeated comparison number of 2 was applied. All behavioral analyses were performed by experimenters who were blind to the treatment condition.

REFERENCES

1. M. R. Kelley. T. Z. Deeb, N. J. Brandon, J. Dunlop. P. A. Davies, S. J. Moss, Compromising KCC2 transporter activity enhances the development of continuous seizure activity. *Neuropharmacology* 108, 103-110 (2016).
2. K. T. Kahle, A. R. Khanna, J. Duan, K. J. Staley, E. Delpire, A. Poduri, The KCC2 Cotransporter and Human Epilepsy: Getting Excited About Inhibition. *Neuroscientist* 22, 555-562 (2016).
3. K. T. Kahle, N. D. Merner, P. Friedel, L. Silayeva, B. Liang, A. Khanna, Y. Shang, P. Lachance-Touchette, C. Bourassa, A. Levert, P. A. Dion, B. Walcott, D. Spiegelman, A. Dionne-Laporte, A. Hodgkinson, P. Awadalla, H. Nikbakht, J. Majewski, P. Cossette, T. Z. Deeb, S. J. Moss, I. Medina, G. A. Rouleau, Genetically encoded impairment of neuronal KCC2 cotransporter function in human idiopathic generalized epilepsy. *EMBO Rep* 15, 766-774 (2014).
4. T. M. Hyde, B. K. Lipska, T. Ali, S. V. Mathew, A. J. Law, O. E. Metitiri, R. E. Straub, T. Ye, C. Colantuoni, M. M. Herman, L. B. Bigelow, D. R. Weinberger, J. E. Kleinman, Expression of GABA signaling molecules KCC2, NKCC1, and GAD1 in cortical development and schizophrenia. *J Neurosci* 31, 11088-11095 (2011).
5. D. Arion, D. A. Lewis, Altered expression of regulators of the cortical chloride transporters NKCC1 and KCC2 in schizophrenia. *Arch Gen Psychiatry* 68, 21-31 (2011).
6. P. Boulenguez, S. Liabeuf, R. Bos, H. Bras, C. Jean-Xavier, C. Brocard, A. Sul, P. Darbon, D. Cattaert, E. Delpire, M. Marsala, L. Vinay, Down-regulation of the potassium-chloride cotransporter KCC2 contributes to spasticity after spinal cord injury. *Nat Med* 16, 302-307 (2010).
7. X. Tang, J. Kim, L. Zhou, E. Wengert, L. Zhang, Z. Wu, C. Carromeu, A. R. Muotri, M. C. Marchetto, F. H. Gage, G. Chen, KCC2 rescues functional deficits in human neurons derived from patients with Rett syndrome. *Proc Natl Acad Sci USA* 113, 751-756 (2016).
8. A. Banerjee, R. V. Rikhye, V. Breton-Provencher, X. Tang, C. Li, K. Li, C. A. Runyan, Z. Fu, R. Jaenisch, M. Sur, Jointly reduced inhibition and excitation underlies circuit-wide changes in cortical processing in Rett syndrome.*Proceedings of the National Academy of Sciences* 113, 7287 (2016).
9. D. G. Glaze, A. K. Percy, S. Skinner, K. J. Motil, J. L. Neul, J. O. Barrish, J. B. Lane, S. P. Geerts, F. Annese, J. Graham, L. McNair, H. S. Lee, Epilepsy and the natural history of Rett syndrome. *Neurology* 74, 909-912 (2010).
10. S. N. Pandis D, Seizures in Alzheimer disease: clinical and epidemiological data. *Epilepsy Curr* September; 12(5):184-7, (2012).
11. O. Yizhar, L. E. Fenno, M. Prigge, F. Schneider, T. J. Davidson, D. J. O'Shea, V. S. Sohal, I. Goshen, J. Finkelstein, J. T. Paz, K. Stehfest, R. Fudim, C. Ramakrishnan, J. R. Huguenard, P. Hegemann, K. Deisseroth, Neocortical excitation/inhibition balance in information processing and social dysfunction. *Nature* 477, 171-178 (2011).
12. O. Marin, Interneuron dysfunction in psychiatric disorders. *Nat Rev Neurosci* 13, 107-120 (2012).
13. C. E. Robertson, E. M. Ratai, N. Kanwisher, Reduced GABAergic Action in the Autistic Brain. *Curr Biol* 26, 80-85 (2016).
14. B. Zikopoulos, H. Barbas, Altered neural connectivity in excitatory and inhibitory cortical circuits in autism. *Front Hum Neurosci* 7, 609 (2013).
15. W. L. Henderson C, Kinoshita M N, Shumway M, Hammond R S, Postma F R, Brynczka C, Rush R, Thomas A, Paylor R, Warren S T, Vanderklish P W, Kind P C, Carpenter R L, Bear M F, Healy A M., Reversal of disease-related pathologies in the fragile X mouse model by selective activation of GABAB receptors with arbaclofen. *Sci Transl Med.* 2012 Sep. 19;4 (152), (2012).
16. A. A. Till S M, Jackson A D, Katsanevaki D, Barnes S A, Osterweil E K, Bear M F, Chattarji S, Wood E R, Wyllie D J, Kind P C., Conserved hippocampal cellular pathophysiology but distinct behavioural deficits in a new rat model of FXS. *Hum Mol Genet.* November 1;24(21):5977-84, (2015).
17. Q. He, T. Nomura, J. Xu, A. Contractor, The developmental switch in GABA polarity is delayed in fragile X mice. *European Journal of Neuroscience* 34, 446-450 (2014).
18. V. S. Dani, Q. Chang, A. Maffei, G. G. Turrigiano, R. Jaenisch, S. B. Nelson, Reduced cortical activity due to a shift in the balance between excitation and inhibition in a mouse model of Rett syndrome. *Proc Natl Acad Sci USA* 102, 12560-12565 (2005).
19. Y. Ben-Ari, J. L. Gaiarsa, R. Tyzio, R. Khazipov, GABA: a pioneer transmitter that excites immature neurons and generates primitive oscillations. *Physiol Rev* 87, 1215-1284 (2007).
20. K. Kaila, T. J. Price, J. A. Payne, M. Puskarjov, J. Voipio, Cation-chloride cotransporters in neuronal development, plasticity and disease. *Nat Rev Neurosci* 15, 637-654 (2014).
21. H. Li, S. Khirug, C. Cai, A. Ludwig, P. Blaesse, J. Kolikova, R. Afzalov, S. K. Coleman, S. Lauri, M. S. Airaksinen, K. Keinanen, L. Khiroug, M. Saarma, K.

Kaila, C. Rivera, KCC2 interacts with the dendritic cytoskeleton to promote spine development. *Neuron* 56, 1019-1033 (2007).
22. M. Puskarjov, P. Seja, S. E. Heron, T. C. Williams, F. Ahmad, X. Iona, K. L. Oliver, B. E. Grinton, L. Vutskits, I. E. Scheffer, S. Petrou, P. Blaesse, L. M. Dibbens, S. F. Berkovic, K. Kaila, A variant of KCC2 from patients with febrile seizures impairs neuronal Cl-extrusion and dendritic spine formation. *EMBO Rep* 15, 723-729 (2014).
23. G. Gauvain, I. Chamma, Q. Chevy, C. Cabezas, T. Irinopoulou, N. Bodrug, M. Carnaud, S. Levi, J. C. Poncer, The neuronal K-Cl cotransporter KCC2 influences postsynaptic AMPA receptor content and lateral diffusion in dendritic spines. *Proc Natl Acad Sci U S A* 108, 15474-15479 (2011).
24. S. P. Janssen, M. Truin, M. Van Kleef, E. A. Joosten, Differential GABAergic disinhibition during the development of painful peripheral neuropathy. *Neuroscience* 184, 183-194 (2011).
25. I. Ferando, G. C. Faas, I. Mody, Diminished KCC2 confounds synapse specificity of LTP during senescence. *Nat Neurosci* 19, 1197-1200 (2016).
26. M. L. Horvath P M. MeCP2 as an Activator of Gene Expression. *Trends Neurosci.* February;41(2):72-74, (2018).
27. M. Chahrour, S. Y. Jung, C. Shaw, X. Zhou, S. T. Wong, J. Qin, H. Y. Zoghbi, MeCP2, a key contributor to neurological disease, activates and represses transcription. *Science* 320, 1224-1229 (2008).
28. S. J. Williams JR, Kumari V G, Wilson M, Payne J A., The neuron-specific K-Cl cotransporter, KCC2. Antibody development and initial characterization of the protein. *J Biol Chem* April 30;274(18):, 12656-12664 (1999).
29. Delpire E, Lu J, England R, Dull C, T. T., Deafness and imbalance associated with inactivation of the secretory Na-K-2Cl co-transporter. *Nat Genet.*, (1999).
30. C. A. Chapleau, G. D. Calfa, M. C. Lane, A. J. Albertson, J. L. Larimore, S. Kudo, D. L. Armstrong, A. K. Percy, L. Pozzo-Miller, Dendritic spine pathologies in hippocampal pyramidal neurons from Rett syndrome brain and after expression of Rett-associated MECP2 mutations. *Neurobiol Dis* 35, 219-233 (2009).
31. M. Phillips, L. Pozzo-Miller, Dendritic spine dysgenesis in autism related disorders. *Neurosci Lett* 601, 30-40 (2015).
32. P. Penzes, M. E. Cahill, K. A. Jones, J. E. VanLeeuwen, K. M. Woolfrey, Dendritic spine pathology in neuropsychiatric disorders. *Nat Neurosci* 14, 285-293 (2011).
33. E. Delpire, E. Days, L. M. Lewis, D. Mi, K. Kim, C. W. Lindsley, C. D. Weaver, Small-molecule screen identifies inhibitors of the neuronal K-Cl cotransporter KCC2. *Proc Natl Acad Sci U S A* 106, 5383-5388 (2009).
34. D. Zhang, S. M. Gopalakrishnan, G. Freiberg, C. S. Surowy, A thallium transport FLIPR-based assay for the identification of KCC2-positive modulators. *J Biomol Screen* 15, 177-184 (2010).
35. E. Delpire, C. D. Weaver, Challenges of Finding Novel Drugs Targeting the K-Cl Cotransporter. *ACS Chem Neurosci* 7, 1624-1627 (2016).
36. I. Chamma, Q. Chevy, J. C. Poncer, S. Levi, Role of the neuronal K-Cl co-transporter KCC2 in inhibitory and excitatory neurotransmission. *Front Cell Neurosci* 6, 5 (2012).
37. V. S. Dani, S. B. Nelson, Intact long-term potentiation but reduced connectivity between neocortical layer 5 pyramidal neurons in a mouse model of Rett syndrome. *J Neurosci* 29, 11263-11270 (2009).
38. E. T. K. Lisa M. Monteggia, Rett Syndrome and the Impact of MeCP2 Associated Transcriptional Mechanisms on Neurotransmission. *Biol Psychiatry*. February 1; 65(3): 204-210., (2009).
39. E. D. Nelson, E. T. Kavalali, L. M. Monteggia, MeCP2-dependent transcriptional repression regulates excitatory neurotransmission. *Curr Biol* 16, 710-716 (2006).
40. W. C. Szymczak A L, Wang Y, Vignali K M, Dilioglou S, Vanin E F, Vignali DA., Correction of multi-gene deficiency in vivo using a single 'self-cleaving' 2A peptide-based retroviral vector. *Nat Biotechnol*. May; 22(5):589-94, (2004).
41. K. W. Pratz, J. Cortes, G. J. Roboz, N. Rao, O. Arowojolu, A. Stine, Y. Shiotsu, A. Shudo, S. Akinaga, D. Small, J. E. Karp, M. Levis, A pharmacodynamic study of the FLT3 inhibitor KW-2449 yields insight into the basis for clinical response. *Blood* 113, 3938-3946 (2009).
42. M. P. Polychronopoulos P, Skaltsounis A L, Myrianthopoulos V, Mikros E, Tarricone A, Musacchio A, Roe S M, Pearl L, Leost M, Greengard P, Meijer L., Structural basis for the synthesis of indirubins as potent and selective inhibitors of glycogen synthase kinase-3 and cyclin-dependent kinases. *J Med Chem*. February 12;47(4):935-46., (2004).
43. P. J. Lein, C. D. Barnhart, I. N. Pessah, Acute hippocampal slice preparation and hippocampal slice cultures. *Methods Mol Biol* 758, 115-134 (2011).
44. J. Yamada, A. Okabe, H. Toyoda, W. Kilb, H. J. Luhmann, A. Fukuda, Cl-uptake promoting depolarizing GABA actions in immature rat neocortical neurones is mediated by NKCC1. *J Physiol* 557, 829-841 (2004).
45. A. Munoz, P. Mendez, J. DeFelipe, F. J. Alvarez-Leefmans, Cation-chloride cotransporters and GABAergic innervation in the human epileptic hippocampus. *Epilepsia* 48, 663-673 (2007).
46. T. P. Q. Chen G, van den Pol A N, Excitatory actions of GABA in developing rat hypothalamic neurones. *The Journal of Physiology* 10.1113/jphysiol.1996.sp021505, (1996).
47. N. M. F. R. G. GOGLIOTTI, B. J. STANSLEY, C. K. JONES, C. W. LINDSLEY, P. J. CONN, C. M., Total RNA-sequencing of Rett syndrome autopsy samples to facilitate preclinical target identification. *Society for Neuroscience Annual Conference* 2017 Session 450—Advances in Understanding Rett Syndrome Pathophysiology, (2017).
48. S. T. Duarte, J. Armstrong, A. Roche, C. Ortez, A. Perez, M. O'Callaghan Mdel, A. Pereira, F. Sanmarti, A. Ormazabal, R. Artuch, M. Pineda, A. Garcia-Cazorla, Abnormal expression of cerebrospinal fluid cation chloride cotransporters in patients with Rett syndrome. *PLOS One* 8, e68851 (2013).
49. N. Guida, G. Laudati, S. Anzilotti, A. Secondo, P. Montuori, G. Di Renzo, L. M. Canzoniero, L. Formisano, Resveratrol via sirtuin-1 downregulates RE1-silencing transcription factor (REST) expression preventing PCB-95-induced neuronal cell death. *Toxicol Appl Pharmacol* 288, 387-398 (2015).

50. I. Nagy, D. Friston, J. S. Valente, J. V. T. Perez, A. P. Andreou, Pharmacology of the Capsaicin Receptor, Transient Receptor Potential Vanilloid Type-1 Ion Channel. 39-76 (2014).
51. M. Yeo, K. Berglund, G. Augustine, W. Liedtke, Novel repression of Kcc2 transcription by REST-RE-1 controls developmental switch in neuronal chloride. *J Neurosci* 29, 14652-14662 (2009).
52. Banerjee A, Rikhye R V, B.-P. V, Tang X, Li C, Li K, Runyan C A, Fu Z, Jaenisch R, S. M, Jointly reduced inhibition and excitation underlies circuit-wide changes in cortical processing in Rett Syndrome. *Proc Natl Acad Sci U S A.*, (2016).
53. H. T. Chao, H. Y. Zoghbi, C. Rosenmund, MeCP2 controls excitatory synaptic strength by regulating glutamatergic synapse number. *Neuron* 56, 58-65 (2007).
54. M. C. Marchetto, C. Carromeu, A. Acab, D. Yu, G. W. Yeo, Y. Mu, G. Chen, F. H. Gage, A. R. Muotri, A model for neural development and treatment of Rett syndrome using human induced pluripotent stem cells. *Cell* 143, 527-539 (2010).
55. W. H. Li Y, Muffat J, Cheng A W, Orlando D A, Loven J, Kwok S M, Feldman D A, Bateup H S, Gao Q, Hockemeyer D, Mitalipova M, Lewis C A, Vander Heiden M G, Sur M, Young R A, Jaenisch R., Global Transcriptional and Translational Repression in Human-Embryonic-Stem-Cell-Derived Rett Syndrome Neurons. *Cell Stem Cell,* 446-458 (2013).
56. M. V. Nguyen, F. Du, C. A. Felice, X. Shan, A. Nigam, G. Mandel, J. K. Robinson, N. Ballas, MeCP2 is critical for maintaining mature neuronal networks and global brain anatomy during late stages of postnatal brain development and in the mature adult brain. *J Neurosci* 32, 10021-10034 (2012).
57. X. Tang, L. Zhou, A. M. Wagner, M. C. Marchetto, A. R. Muotri, F. H. Gage, G. Chen, Astroglial cells regulate the developmental timeline of human neurons differentiated from induced pluripotent stem cells. *Stem Cell Res* 11, 743-757 (2013).
58. K. A. Julu P O, Apartopoulos F, Al-Rawas S, Engerström I W, Engerström L, Jamal G A, Hansen S., Characterisation of breathing and associated central autonomic dysfunction in the Rett disorder. *Arch Dis Child.* July;85(1):29-37., (2001).
59. S. Li, C. Wang, M. Wang, W. Li, K. Matsumoto, Y. Tang, Antidepressant like effects of piperine in chronic mild stress treated mice and its possible mechanisms. *Life Sci* 80, 1373-1381 (2007).
60. B. Pragnya, J. S. Kameshwari, B. Veeresh, Ameliorating effect of piperine on behavioral abnormalities and oxidative markers in sodium valproate induced autism in BALB/C mice. *Behav Brain Res* 270, 86-94 (2014).
61. J. Castro, R. I. Garcia, S. Kwok, A. Banerjee, J. Petravicz, J. Woodson, N. Mellios, D. Tropea, M. Sur, Functional recovery with recombinant human IGF1 treatment in a mouse model of Rett Syndrome. *Proc Natl Acad Sci U S A* 111. 9941-9946 (2014).
62. K. Ikeda, H. Onimaru, J. Yamada, K. Inoue, S. Ueno, T. Onaka, H. Toyoda, A. Arata, T. O. Ishikawa, M. M. Taketo, A. Fukuda, K. Kawakami, Malfunction of respiratory-related neuronal activity in Na+, K+-ATPase alpha2 subunit-deficient mice is attributable to abnormal Cl-homeostasis in brainstem neurons. *J Neurosci* 24, 10693-10701 (2004).
63. H. L. K Ure, W Wang, A Ito-Ishida, Z Wu, L He, Restoration of Mecp2 expression in GABAergic neurons is sufficient to rescue multiple disease features in a mouse model of Rett syndrome. *eLife,* (2016).
64. M. Gagnon, M. J. Bergeron, G. Lavertu, A. Castonguay, S. Tripathy, R. P. Bonin, J. Perez-Sanchez, D. Boudreau, B. Wang, L. Dumas, I. Valade, K. Bachand, M. Jacob-Wagner, C. Tardif, I. Kianicka, P. Isenring, G. Attardo, J. A. Coull, Y. De Koninck, Chloride extrusion enhancers as novel therapeutics for neurological diseases. *Nat Med* 19, 1524-1528 (2013).
65. H. T. Chao, H. Chen, R. C. Samaco, M. Xue, M. Chahrour, J. Yoo, J. L. Neul. S. Gong, H. C. Lu, N. Heintz, M. Ekker, J. L. Rubenstein, J. L. Noebels, C. Rosenmund, H. Y. Zoghbi, Dysfunction in GABA signalling mediates autism-like stereotypies and Rett syndrome phenotypes. *Nature* 468, 263-269 (2010).
66. L. G. Guida N, Anzilotti S, Secondo A, Montuori P, Di Renzo G, Canzoniero L M, Formisano L., Resveratrol via sirtuin-1 downregulates RE1-silencing transcription factor (REST) expression preventing PCB-95-induced neuronal cell death. *Toxicol Appl Pharmacol.,* (2015).
67. J. A. Baur, D. A. Sinclair, Therapeutic potential of resveratrol: the in vivo evidence. *Nat Rev Drug Discov* 5, 493-506 (2006).
68. J. Gambini, M. Ingles, G. Olaso, R. Lopez-Grueso, V. Bonet-Costa, L. Gimeno-Mallench, C. Mas-Bargues, K. M. Abdelaziz, M. C. Gomez-Cabrera, J. Vina, C. Borras, Properties of Resveratrol: In Vitro and In Vivo Studies about Metabolism, Bioavailability, and Biological Effects in Animal Models and Humans. *Oxid Med Cell Longev* 2015, 837042 (2015).
69. P. C. S. Frame, The renaissance of GSK3. *Nature Reviews Molecular Cell Biology* 2, 769-776 (October 2001)|(2001).
70. H. Konig, M. Levis, Targeting FLT3 to treat leukemia. *Expert Opin Ther Targets* 19, 37-54 (2015).
71. A. T. Fathi, Y. B. Chen, The role of FLT3 inhibitors in the treatment of FLT3-mutated acute myeloid leukemia. *Eur J Haematol* 98, 330-336 (2017).
72. C. Y. Brazel, M. H. Ducceschi, B. Pytowski, S. W. Levison, The FLT3 tyrosine kinase receptor inhibits neural stem/progenitor cell proliferation and collaborates with NGF to promote neuronal survival. *Mol Cell Neurosci* 18, 381-393 (2001).
73. Y. Ben-Ari, NKCC1 Chloride Importer Antagonists Attenuate Many Neurological and Psychiatric Disorders. *Trends in Neurosciences* 40, p536-554 (2017).
74. R. Tyzio, R. Nardou, D. C. Ferrari, T. Tsintsadze, A. Shahrokhi, S. Eftekhari, I. Khalilov, V. Tsintsadze, C. Brouchoud, G. Chazal, E. Lemonnier, N. Lozovaya, N. Burnashev, Y. Ben-Ari, Oxytocin-mediated GABA inhibition during delivery attenuates autism pathogenesis in rodent offspring. *Science* 343, 675-679 (2014).
75. G. Deidda, M. Parrini, S. Naskar, I. F. Bozarth, A. Contestabile, L. Cancedda, Reversing excitatory GABAAR signaling restores synaptic plasticity and memory in a mouse model of Down syndrome. *Nat Med* 21, 318-326 (2015).
76. E. Lemonnier, C. Degrez, M. Phelep, R. Tyzio, F. Josse, M. Grandgeorge, N. Hadjikhani, Y. Ben-Ari, A randomised controlled trial of bumetanide in the treatment of autism in children. *Transl Psychiatry* 2, e202 (2012).
77. E. Lemonnier, G. Robin, C. Degrez, R. Tyzio, M. Grandgeorge, Y. Ben-Ari, Treating Fragile X syndrome with the diuretic bumetanide: a case report.*Acta Paediatr* 102, e288-290 (2013).

78. L. D. Hübner C A, Hermans-Borgmeyer I., Expression of the Na-K-2Cl-cotransporter NKCC1 during mouse development. *Mech Dev.* April;102(1-2):267-9., (2001).
79. S. C. Gore M E, Porta C, Bracarda S, Bjarnason G A, Oudard S, Lee SH , Haanen J, Castellano D, Vrdoljak E, Schöffski P, Mainwaring P, Hawkins R E, Crinò L, Kim T M, Carteni G, Eberhardt W E, Zhang K, Fly K, Matczak E, Lechuga M J, Hariharan S, Bukowski R., Final results from the large sunitinib global expanded-access trial in metastatic renal cell carcinoma. *Br J Cancer* June 30;113(1):12-9., (2015).
80. M. A. Eldar-Finkelman H, GSK-3 Inhibitors: Preclinical and Clinical Focus on CNS. *Front Mol Neurosci.* 2011 Oct. 31;4:32., (2011).
81. H. M. Panahi Y, Khalili N, Naimi E, Majeed M, Sahebkar A, Antioxidant and anti-inflammatory effects of curcuminoid-piperine combination in subjects with metabolic syndrome: A randomized controlled trial and an updated meta-analysis. *Clin Nutr.* December;34(6): 1101-8., (2015).
82. T. R. Turner R S, Craft S, van Dyck C H, Mintzer J. Reynolds B A, Brewer J B, Rissman R A, Raman R, Aisen P S; Alzheimer's Disease Cooperative Study., A randomized, double-blind, placebo-controlled trial of resveratrol for Alzheimer disease. *Neurology.* October 20;85(16):1383-91, (2015).
183. D. T. Lioy, S. K. Garg, C. E. Monaghan, J. Raber, K. D. Foust, B. K. Kaspar, P. G. Hirrlinger, F. Kirchhoff, J. M. Bissonnette, N. Ballas, G. Mandel, A role for glia in the progression of Rett's syndrome. *Nature* 475, 497-500 (2011).
84. E. Delpire, K. T. Kahle, The KCC3 cotransporter as a therapeutic target for peripheral neuropathy. *Expert Opin Ther Targets* 21, 113-116 (2017).
85. P. B. M Kobayashi, Reduced inhibition of dentate granule cells in a model of temporal lobe epilepsy. *Journal of Neuroscience*, (2003).
86. X. Jin, J. R. Huguenard, D. A. Prince, Impaired Cl-extrusion in layer V pyramidal neurons of chronically injured epileptogenic neocortex. *J Neurophysiol* 93, 2117-2126 (2005).
87. E. Palma, M. Amici, F. Sobrero, G. Spinelli, S. Di Angelantonio, D. Ragozzino, A. Mascia, C. Scoppetta, V. Esposito, R. Miledi, F. Eusebi, Anomalous levels of Cl-transporters in the hippocampal subiculum from temporal lobe epilepsy patients make GABA excitatory. *Proc Natl Acad Sci U S A* 103, 8465-8468 (2006).
88. R. Tao, C. Li, E. N. Newburn, T. Ye, B. K. Lipska, M. M. Herman, D. R. Weinberger, J. E. Kleinman, T. M. Hyde, Transcript-specific associations of SLC12A5 (KCC2) in human prefrontal cortex with development, schizophrenia, and affective disorders. *J Neurosci* 32, 5216-5222 (2012).
89. E. P. S. David P. Bonislawski, Akiva S. Cohen, Brain injury impairs dentate gyrus inhibitory efficacy. *Neurobiol Dis.*, (2006).
90. N. Jaenisch, O. W. Witte, C. Frahm, Downregulation of potassium chloride cotransporter KCC2 after transient focal cerebral ischemia. *Stroke* 41, e151-159 (2010).
91. M. A. Martin-Aragon Baudel, A. V. Poole, M. G. Darlison, Chloride co-transporters as possible therapeutic targets for stroke. *J Neurochem* 140, 195-209 (2017).
92. T. A. Rangroo Thrane V, Wang F, Cotrina M L, Smith N A, Chen M, Xu Q, Kang N, Fujita T, Nagelhus E A, Nedergaard M., Ammonia triggers neuronal disinhibition and seizures by impairing astrocyte potassium buffering. *Nat Med.* December; 19(12):1643-8, (2013).
93. Y. Li, H. Wang, J. Muffat, A. W. Cheng, D. A. Orlando, J. Loven, S. M. Kwok, D. A. Feldman, H. S. Bateup, Q. Gao, D. Hockemeyer, M. Mitalipova, C. A. Lewis, M. G. Vander Heiden, M. Sur, R. A. Young, R. Jaenisch, Global transcriptional and translational repression in human-embryonic-stem-cell-derived Rett syndrome neurons. *Cell Stem Cell* 13, 446-458 (2013).
94. G. M. Pelz O, Boutros M., web cellHTS2: a web-application for the analysis of high-throughput screening data. *BMC Bioinformatics* 2010 Apr. 12;11:185., (2010).
95. J. A. del Rio, E. Soriano, Regenerating cortical connections in a dish: the entorhino-hippocampal organotypic slice co-culture as tool for pharmacological screening of molecules promoting axon regeneration. *Nat Protoc* 5, 217-226 (2010).
96. C. G. Jiang M, High Ca2+-phosphate transfection efficiency in low-density neuronal cultures. *Nature Protocol* 1(2):, 695-700. (2006).

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method of treating a subject with epilepsy characterized by deficient expression or function of KCC2, the method comprising:
administering to the subject a therapeutically effective amount of a compound selected from the group consisting of Feline McDonough sarcoma-like tyrosine kinase 3 (FLT3) inhibitors, glycogen synthase kinase 3 (GSK3) inhibitors, GABA reuptake inhibitors, monoamine oxidase inhibitors (MAOI), norepinephrine reuptake inhibitors (NRI), dopamine antagonists, transient receptor potential cation channel subfamily V member 1 (TRPV1) activators, monoamine transporter activators, tropomyosin receptor kinase B (TrkB) agonists, ampakines, and pharmaceutically acceptable salts thereof.

2. The method of claim 1, wherein the compound is selected from the group consisting of (E)-(4-(2-(1H-indazol-3-yl)vinyl)phenyl)(piperazin-1-yl)methanone (KW-2449), 2Z,3E)-6'-bromo-3-(hydroxyimino)-[2,3'-biindolinylidene]-2'-one (KIN 001-043), N-(2-diethylaminoethyl)-5-[(Z)-(5-fluoro-2-oxo-1H-indol-3-ylidene)methyl]-2,4-dimethyl-1H-pyrrole-3-carboxamide (Sunitinib), 1-(2-(5-(2-(3-methyloxetan-3-yl)ethyl)-1H-benzo[d]imidazol-1-yl) quinolin-8-yl)piperidin-4-amine (Crenolanib), N'-[4-[(6,7-dimethoxy-4-quinolinyl)oxy]phenyl]-N-(4-fluorophenyl)-1,1-cyclopropanedicarboxamide (XL-184), 3-((6-(3-aminophenyl)-7H-pyrrolo[2,3-d]pyrimidin-4-yl)methyl) phenol (TWS-119), (2Z,3E)-3-(hydroxyimino)-[2,3'-biindolinylidene]-2'-one (Indirubin-monoxime), piperine, and pharmaceutically acceptable salts thereof.

3. A method of treating a subject with an autism spectrum disorder (ASD), Down syndrome, or Fragile-X syndrome, the method comprising:
administering to the subject a therapeutically effective amount of a compound selected from the group consisting of Feline McDonough sarcoma-like tyrosine kinase 3 (FLT3) inhibitors, glycogen synthase kinase 3 (GSK3) inhibitors, GABA reuptake inhibitors, monoamine oxidase inhibitors (MAOI), norepinephrine reuptake inhibitors (NRI), dopamine antagonists, transient receptor potential cation channel subfamily V member 1 (TRPV1) activators, monoamine transporter activators, tropomyosin receptor kinase B (TrkB) agonists, ampakines, and pharmaceutically acceptable salts thereof.

4. The method of claim 3, wherein the compound is selected from the group consisting of (E)-(4-(2-(1H-indazol-3-yl)vinyl)phenyl)(piperazin-1-yl)methanone (KW-2449), 2Z,3E)-6'-bromo-3-(hydroxyimino)-[2,3'-biindolinylidene]-2'-one (KIN 001-043), N-(2-diethylaminoethyl)-5-[(Z)-(5-fluoro-2-oxo-1H-indol-3-ylidene)methyl]-2,4-dimethyl-1H-pyrrole-3-carboxamide (Sunitinib), 1-(2-(5-(2-(3-methyloxetan-3-yl)ethyl)-1H-benzo[d]imidazol-1-yl) quinolin-8-yl)piperidin-4-amine (Crenolanib), N'-[4-[(6,7-dimethoxy-4-quinolinyl)oxy]phenyl]-N-(4-fluorophenyl)-1,1-cyclopropanedicarboxamide (XL-184), 3-((6-(3-aminophenyl)-7H-pyrrolo[2,3-d]pyrimidin-4-yl)methyl) phenol (TWS-119), (2Z,3E)-3-(hydroxyimino)-[2,3'-biindolinylidene]-2'-one (Indirubin-monoxime), piperine, and pharmaceutically acceptable salts thereof.

5. The method of claim 1, wherein the subject is a mammal.

6. The method of claim 1, wherein the subject is a human.

7. The method of claim 1, wherein the compound is administered in an amount sufficient to increase expression of neuronal KCC2.

8. The method of claim 7, wherein the compound is administered in an amount sufficient to increase function of neuronal KCC2.

9. The method of claim 1, wherein the compound is a FLT3 inhibitor or a pharmaceutically acceptable salt thereof.

10. The method of claim 9, wherein the compound is (E)-(4-(2-(1H-indazol-3-yl)vinyl)phenyl)(piperazin-1-yl)methanone (KW-2449), N-(2-diethylaminoethyl)-5-[(Z)-(5-fluoro-2-oxo-1H-indol-3-ylidene)methyl]-2,4-dimethyl-1H-pyrrole-3-carboxamide (Sunitinib), 1-(2-(5-(2-(3-methyloxetan-3-yl)ethyl)-1H-benzo[d]imidazol-1-yl)quinolin-8-yl)piperidin-4-amine (Crenolanib), N'-[4-[(6,7-dimethoxy-4-quinolinyl)oxy]phenyl]-N-(4-fluorophenyl)-1,1-cyclopropanedicarboxamide (XL-184), or a pharmaceutically acceptable salt thereof.

11. The method of claim 9, wherein the compound is (E)-(4-(2-(1H-indazol-3-yl)vinyl)phenyl)(piperazin-1-yl)methanone (KW-2449) or a pharmaceutically acceptable salt thereof.

12. The method of claim 3, wherein the subject is a mammal.

13. The method of claim 3, wherein the subject is a human.

14. The method of claim 3, wherein the compound is administered in an amount sufficient to increase expression of neuronal KCC2.

15. The method of claim 14, wherein the compound is administered in an amount sufficient to increase function of neuronal KCC2.

16. The method of claim 3, wherein the compound is a FLT3 inhibitor or a pharmaceutically acceptable salt thereof.

17. The method of claim 16, wherein the compound is (E)-(4-(2-(1H-indazol-3-yl)vinyl)phenyl)(piperazin-1-yl)methanone (KW-2449), N-(2-diethylaminoethyl)-5-[(Z)-(5-fluoro-2-oxo-1H-indol-3-ylidene)methyl]-2,4-dimethyl-1H-pyrrole-3-carboxamide (Sunitinib), 1-(2-(5-(2-(3-methyloxetan-3-yl)ethyl)-1H-benzo[d]imidazol-1-yl)quinolin-8-yl)piperidin-4-amine (Crenolanib), N'-[4-[(6,7-dimethoxy-4-quinolinyl)oxy]phenyl]-N-(4-fluorophenyl)-1,1-cyclopropanedicarboxamide (XL-184), or a pharmaceutically acceptable salt thereof.

18. The method of claim 16, wherein the compound is (E)-(4-(2-(1H-indazol-3-yl)vinyl)phenyl)(piperazin-1-yl)methanone (KW-2449) or a pharmaceutically acceptable salt thereof.

* * * * *

SEQUENCE LISTING

```
<160> NUMBER OF SEQ ID NOS: 8

<210> SEQ ID NO 1
<211> LENGTH: 126
<212> TYPE: DNA
<213> ORGANISM: Artificial Sequence
<220> FEATURE:
<223> OTHER INFORMATION: Synthetic Polynucleotide

<400> SEQUENCE: 1
ggcaaaccga ttccgaatcc gctgctgggc ctggattcca cctacccata cgatgttcca      60
gattacgctg ccactaactt ctccctgttg aaacaagcag gggatgtcga agagaatccc     120
gggcca                                                                126

<210> SEQ ID NO 2
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 2
ccgtgcctgc agaacatctt tggtgt                                           26

<210> SEQ ID NO 3
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 3
gccaccagca ggcacaacac cattgg                                           26

<210> SEQ ID NO 4
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 4
ttgcagtctt gccatcctct                                                  20

<210> SEQ ID NO 5
<211> LENGTH: 26
<212> TYPE: DNA
<213> ORGANISM: Artificial Sequence
<220> FEATURE:
<223> OTHER INFORMATION: Synthetic Polynucleotide
```

```
<400> SEQUENCE: 5
ctttcctgga acaggagact tgaggg                                        26

<210> SEQ ID NO 6
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 6
ggctggtaca tctccatcac ttttgag                                       27

<210> SEQ ID NO 7
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 7
ggcaccaagg atgtggtagt                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 8
accatctact cctgagaacc                                               20
```